(12) United States Patent
Takeyama et al.

(10) Patent No.: US 6,350,748 B1
(45) Date of Patent: Feb. 26, 2002

(54) SULFAMOYL COMPOUNDS AND AGRICULTURAL AND HORTICULTURAL FUNGICIDES

(75) Inventors: Toshiaki Takeyama; Toshimasa Hamada; Hiroaki Takahashi; Junichi Watanabe, all of Funabashi; Kazuhiro Yamagishi, Saitama-ken; Masanori Nishioka, Saitama-ken; Hiroyuki Suzuki, Saitama-ken, all of (JP)

(73) Assignee: Nissan Chemical Industries Ltd., Tokyo (JP)

( * ) Notice: Subject to any disclaimer, the term of this patent is extended or adjusted under 35 U.S.C. 154(b) by 0 days.

(21) Appl. No.: 09/529,817
(22) PCT Filed: Oct. 23, 1998
(86) PCT No.: PCT/JP98/04808
§ 371 Date: Jun. 2, 2000
§ 102(e) Date: Jun. 2, 2000
(87) PCT Pub. No.: WO99/21851
PCT Pub. Date: May 6, 1999

(30) Foreign Application Priority Data
Oct. 24, 1997 (JP) .............................................. 9-292399

(51) Int. Cl.[7] ..................... C07D 403/06; C07D 403/12; C07D 471/04; A01N 43/653; A01N 43/84
(52) U.S. Cl. ..................... 514/235.2; 544/112; 514/384; 514/323; 514/306; 546/201; 546/121; 548/263.2
(58) Field of Search ....................... 548/263.2; 514/384, 514/323, 235.2, 300; 546/201, 121; 544/112

(56) References Cited
FOREIGN PATENT DOCUMENTS

| JP | 63-255269 A | 10/1988 |
|----|-------------|---------|
| JP | 6-32785 A | 2/1994 |
| JP | 7-2803 A | 1/1995 |
| JP | 7-215971 A | 8/1995 |
| JP | WO 97/41113 | * 11/1997 |
| WO | WO 97/41113 A1 | 11/1997 |

* cited by examiner

Primary Examiner—Bruck Kifle
Assistant Examiner—Hong Liu
(74) Attorney, Agent, or Firm—Oliff & Berridge, PLC

(57) ABSTRACT

A sulfamoyl compound of the general formulae (1):

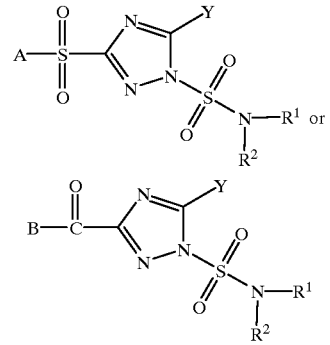

wherein
$R^1$ and $R^2$ are each independently $C_{1-4}$ alkyl, or $R^1$ and $R^2$ together are $C_{4-6}$ alkylene or $C_{4-6}$ alkyleneoxy,
Y is H, halogen, $C_{1-8}$ alkyl, $C_{1-8}$ alkoxy, $C_{1-8}$ alkylthio, $C_{1-8}$ haloalkyl, $C_{1-8}$ haloalkoxy or $C_{1-8}$ haloalkylthio,
A is a predetermined heterocyclic group,
B is a predetermined heterocyclic group which is identical with or different from A,
W is a chemical bond or O,
V is O or S,
D, E, F and G are each independently N, $CR^7$, $CR^8$, $CR^9$ or $CR^{10}$, and
$R^3$, $R^4$, $R^5$, $R^6$, $R^7$, $R^8$, $R^9$, $R^{10}$ and $R^{11}$ are each independently predetermined group such as H, or an unsubstituted or substituted aliphatic, aromatic or heterocyclic group. The sulfamoyl compound is useful as an agricultural and horticultural fungicide.

31 Claims, No Drawings

SULFAMOYL COMPOUNDS AND AGRICULTURAL AND HORTICULTURAL FUNGICIDES

TECHNICAL FIELD

The present invention relates to novel sulfamoyl compounds, and agricultural chemicals (insecticides, fungicides, herbicides, plant growth controlling agents and the like.), particularly agricultural and horticultural fungicides.

BACKGROUND ART

JP-A-3-170464, JP-A-6-32785, JP-A-7-2803 and JP-A-7-215971 describe that certain sulfamoyl compounds have bactericidal activities.

Even the compounds described in the above-described early publications are unsatisfactory in potency and residual effectiveness, thus developments of more useful agricultural and horticultural fungicide have been desired.

DISCLOSURE OF THE INVENTION

Under the circumstances, the present inventors have made extensive research with a view to developing excellent fungicide and, as a result, have found that novel sulfamoyl compounds have remarkable controlling activity as agricultural and horticultural fungicide, thus accomplishing the present invention.

That is, the present invention relates to [1] to [38].
[1] A sulfamoyl compound of the general formulae (1):

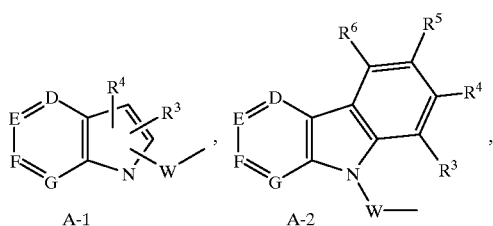

wherein
$R^1$ and $R^2$ are each independently $C_{1-4}$ alkyl, or $R^1$ and $R^2$ together are $C_{4-6}$ alkylene or $C_{4-6}$ alkyleneoxy,
Y is H, halogen, $C_{1-8}$ alkyl, $C_{1-8}$ alkoxy, $C_{1-8}$ alkylthio, $C_{1-8}$ haloalkyl, $C_{1-6}$ haloalkoxy or $C_{1-8}$ haloalkylthio,
A is

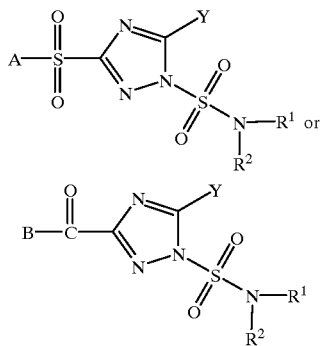

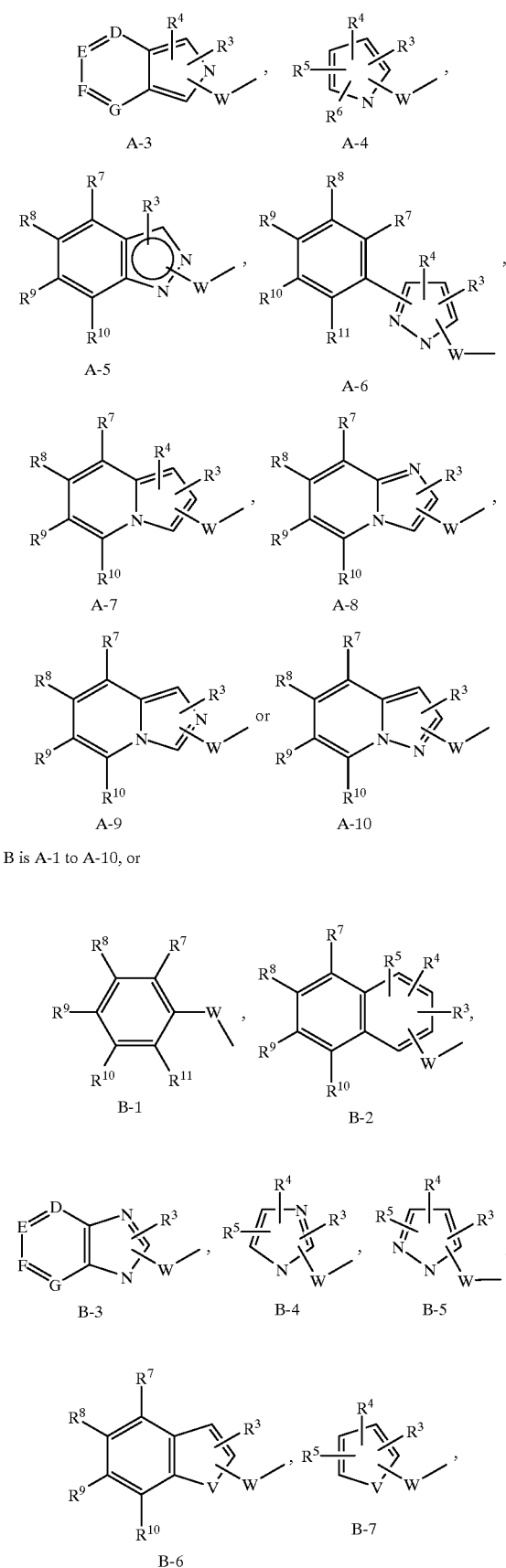

B is A-1 to A-10, or

-continued

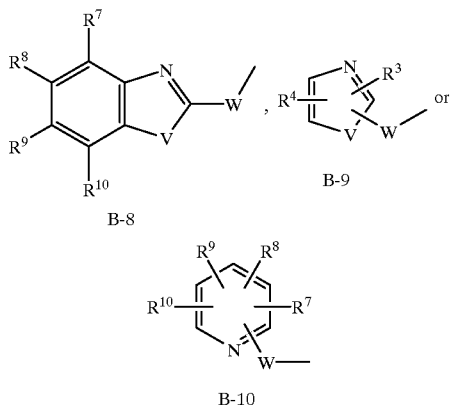

B-8
B-9
B-10

W is a chemical bond or O,
V is O or S,
D, E, F and G are each independently N, $CR^7$, $CR^8$, $CR^9$ or $CR^{10}$, and
$R^3$, $R^4$, $R^5$, $R^6$, $R^7$, $R^8$, $R^9$, $R^{10}$ and $R^{11}$ are each independently H, $C_{1-8}$ alkyl, $C_{3-8}$ cycloalkyl, $C_{2-8}$ alkenyl, $C_{5-8}$ cycloalkenyl, $C_{2-8}$ alkynyl, $C_{1-8}$ alkoxy, $C_{3-8}$ cycloalkyloxy, $C_{5-8}$ cycloalkenyloxy, $C_{2-8}$ alkenyloxy, $C_{2-8}$ alkynyloxy, $C_{1-8}$ alkylthio, $C_{3-8}$ cycloalkylthio, $C_{5-8}$ cycloalkenylthio, $C_{2-8}$ alkenylthio, $C_{2-8}$ alkynylthio, $C_{1-8}$ haloalkyl, $C_{1-8}$ haloalkoxy, $C_{1-8}$ haloalkylthio, $C_{2-8}$ haloalkenyl, $C_{2-8}$ haloalkenyloxy, $C_{2-8}$ haloalkenylthio, $C_{2-8}$ haloalkynyl, $C_{2-8}$ haloalkynyloxy, $C_{2-8}$ haloalkynylthio, phenyl which may be substituted (the kinds of substituent include halogen, $C_{1-8}$ alkyl, $C_{1-8}$ haloalkyl, $C_{1-8}$ alkoxy, $C_{1-8}$ haloalkoxy, $C_{1-8}$ alkylthio, $C_{1-8}$ haloalkylthio, $C_{1-6}$ alkylsulfoxy, $C_{1-6}$ alkylsulfonyl, CN, $NO_2$ and $C_{1-6}$ alkoxycarbonyl, the number of the substituents is 1 to 5, and the substituents may be identical or different), phenyl $C_{1-4}$ alkyl which may be substituted, benzylthio which may be substituted, benzyloxy which may be substituted, phenoxy $C_{1-4}$ alkyl which may be substituted, phenoxy which may be substituted, phenylthio $C_{1-4}$ alkyl which may be substituted, phenylthio which may be substituted, benzoyl which may be substituted, benzoyl $C_{1-4}$ alkyl which may be substituted, benzoyloxy which may be substituted, benzoyloxy $C_{1-4}$ alkyl which may be substituted, naphthyl which may be substituted, 5- or 6-membered heterocyclic ring which may be substituted, $C_{1-8}$ hydroxyalkyl, $C_{1-8}$ hydroxyhaloalkyl, $C_{1-6}$ alkoxy $C_{1-4}$ alkyl, $C_{1-6}$ haloalkoxy $C_{1-4}$ alkyl, $C_{1-6}$ haloalkylthio $C_{1-4}$ alkyl, $C_{1-10}$ dialkoxy $C_{1-4}$ alkyl, $C_{1-3}$ alkylenedioxy $C_{1-4}$ alkyl, $C_{1-6}$ alkylthio $C_{1-4}$ alkyl, $C_{1-10}$ dialkylthio $C_{1-4}$ alkyl, $C_{1-3}$ alkylenedithio $C_{1-4}$ alkyl, $C_{1-6}$ alkoxycarbonyl, $C_{1-6}$ haloalkoxycarbonyl, $C_{1-6}$ alkoxyoxalyl, CHO, $CO_2H$, $C_{1-6}$ alkoxycarbonyl $C_{1-4}$ alkyl, $C_{1-6}$ haloalkoxycarbonyl $C_{1-4}$ alkyl, $NH_2$, $C_{1-6}$ alkylamino, $C_{1-6}$ alkylcarbonylamino, $C_{1-6}$ alkylcarbonylamino $C_{1-4}$ alkyl, $C_{1-6}$ haloalkylcarbonylamino, $C_{1-6}$ haloalkylcarbonylamino $C_{1-4}$ alkyl, $C_{1-6}$ alkoxycarbonylamino, $C_{1-6}$ alkoxycarbonylamino $C_{1-4}$ alkyl, $C_{1-6}$ alkylsulfonylamino, $C_{1-6}$ alkylsulfonylamino $C_{1-4}$ alkyl, $C_{1-6}$ haloalkylsulfonylamino, $C_{1-6}$ haloalkylsulfonylamino $C_{1-4}$ alkyl, $C_{1-6}$ dialkylamino, $C_{1-6}$ dialkylamino $C_{1-4}$ alkyl, $C_{1-6}$ dialkylaminocarbonyl, $C_{1-6}$ dialkylaminocarbonyl $C_{1-4}$ alkyl, $C_{2-6}$ alkyleneimino, $C_{2-6}$ alkyleneimino $C_{1-4}$ alkyl, $C_{2-6}$ alkyleneiminocarbonyl, $C_{2-6}$ alkyleneiminocarbonyl $C_{1-4}$ alkyl, $C_{1-6}$ alkylcarbonyl, $C_{1-6}$ alkylcarbonyloxy, $C_{1-6}$ haloalkylcarbonyl, $C_{1-6}$ haloalkylcarbonyloxy, $C_{1-6}$ alkylcarbonyl $C_{1-4}$ alkyl, $C_{1-6}$ alkylcarbonyloxy $C_{1-4}$ alkyl, $C_{1-6}$ haloalkylcarbonyl $C_{1-4}$ alkyl, $C_{1-6}$ haloalkylcarbonyloxy $C_{1-4}$ alkyl, hydroxyimino $C_{1-4}$ alkyl, $C_{1-6}$ alkoxyimino $C_{1-4}$ alkyl, $C_{1-6}$ alkylcarbonyloxyimino $C_{1-4}$ alkyl, $C_{1-6}$ alkylsulfonyloxyimino $C_{1-4}$ alkyl, $C_{1-6}$ alkylsulfoxy, $C_{1-6}$ haloalkylsulfoxy, $C_{1-6}$ alkylsulfoxy $C_{1-4}$ alkyl, $C_{1-6}$ haloalkylsulfoxy $C_{1-4}$ alkyl, $C_{1-6}$ alkylsulfonyl, $C_{1-6}$ haloalkylsulfonyl, $C_{1-6}$ alkylsulfonyl $C_{1-4}$ alkyl, $C_{1-6}$ haloalkylsulfonyl $C_{1-4}$ alkyl, $C_{1-6}$ alkylsulfonyloxy, $C_{1-6}$ haloalkylsulfonyloxy, $C_{1-6}$ alkylsulfonyloxy $C_{1-4}$ alkyl, $C_{1-6}$ haloalkylsulfonyloxy $C_{1-4}$ alkyl, $C_{1-6}$ haloalkoxysulfonyl, $C_{1-6}$ haloalkoxysulfonyl $C_{1-4}$ alkyl, $C_{1-6}$ dialkylsulfamoyl, $C_{1-6}$ dialkylsulfamoyl $C_{1-4}$ alkyl, $C_{1-6}$ alkoxysulfonyl, $C_{1-6}$ alkoxysulfonyl $C_{1-4}$ alkyl, $C_{2-6}$ cyanoalkyl, CN, $C_{1-6}$ thiocarbamoyl, $C_{1-6}$ nitroalkyl, $NO_2$ or halogen, or two of $R^3$, $R^4$, $R^5$, $R^6$, $R^7$, $R^8$, $R^9$, $R^{10}$ and $R^{11}$ together are $C_{1-3}$ alkylenedioxy which may be substituted, or $C_{3-6}$ alkylene.

[2] A sulfamoyl compound described in [1] above, in which A is A-1.
[3] A sulfamoyl compound described in [1] above, in which A is A-2.
[4] A sulfamoyl compound described in [1] above, in which A is A-3.
[5] A sulfamoyl compound described in [1] above, in which A is A-4.
[6] A sulfamoyl compound described in [1] above, in which A is A-5 or A-6.
[7] A sulfamoyl compound described in [1] above, in which A is A-7 or A-8.
[8] A sulfamoyl compound described in [1] above, in which A is A-9 or A-10.
[9] A sulfamoyl compound described in [1] above, in which B is B-1.
[10] A sulfamoyl compound described in [1] above, in which B is B-2.
[11] A sulfamoyl compound described in [1] above, in which B is B-3 or B-4.
[12] A sulfamoyl compound described in [1] above, in which B is B-5.
[13] A sulfamoyl compound described in [1] above, in which B is B-6 or B-7.
[14] A sulfamoyl compound described in [1] above, in which B is B-8 or B-9.
[15] A sulfamoyl compound described in [1] above, in which B is B-10.
[16] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is $C_{1-8}$ alkylthio.
[17] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is $C_{1-8}$ alkyl.
[18] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is $C_{1-8}$ haloalkyl.
[19] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is halogen.
[20] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is H.

[21] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and $R^3$ is CN.

[22] A sulfamoyl compound described in [1] above, in which $R^1$ and $R^2$ are Me, Y is H, W is a chemical bond, A is A-2, D, E, F and G are $CR^7$, $CR^8$, $CR^9$ or $CR^{10}$, and any of $R^3$, $R^4$, $R^5$ and $R^6$ is H.

[23] A sulfamoyl compound described in [1] above, in which $R^1$ and $R^2$ are Me, Y is H, W is a chemical bond, A is A-4, and at least one of $R^3$, $R^4$, $R^5$ and $R^6$ is phenyl which may be substituted.

[24] A sulfamoyl compound described in [1] above, in which $R^1$ and $R^2$ are Me, Y is H, W is a chemical bond, and B is B-1.

[25] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is $C_{1-8}$ alkyl, and $R^4$ is halogen.

[26] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, and any of $R^3$ and $R^4$ is halogen.

[27] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is $C_{1-8}$ alkyl, and $R^4$ is H or $C_{1-8}$ alkyl.

[28] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is $C_{1-8}$ haloalkyl, and $R^4$ is H, halogen or $C_{1-8}$ alkyl.

[29] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is H or $C_{1-8}$ alkyl, and $R^4$ is $C_{1-6}$ alkoxycarbonyl.

[30] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is H, and $R^4$ is halogen.

[31] A sulfamoyl compound described in [1] above, in which $R^1$ and $R^2$ are Me, Y is H, W is a chemical bond, A is A-1, D, E, F and G are $CR^7$, $CR^8$, $CR^9$ or $CR^{10}$, $R^3$ is CN, and $R^4$ is H or $C_{1-8}$ alkyl.

[32] A sulfamoyl compound described in [1] above, in which $R^1$ and $R^2$ are Me, Y is H, W is a chemical bond, A is A-1, any of D, E, F and G is CH, $R^3$ is $C_{1-8}$ alkyl, and $R^4$ is halogen.

[33] A sulfamoyl compound described in [1] above, in which $R^1$ and $R^2$ are Me, Y is H, W is a chemical bond, A is A-1, any of D, E, F and G is CH, and any of $R^3$ and $R^4$ is halogen.

[34] A sulfamoyl compound described in [1] above, in which $R^1$ and $R^2$ are Me, Y is H, W is a chemical bond, A is A-1, any of D, E, F and G is CH, $R^3$ is $C_{1-8}$ haloalkyl, and $R^4$ is H or $C_{1-3}$ alkyl.

[35] A sulfamoyl compound described in [1] above, in which $R^1$ and $R^2$ are Me, Y is H, W is a chemical bond, A is A-1, any of D, E, F and G is CH, $R^3$ is Me or Et, and $R^4$ is Cl or Br.

[36] A sulfamoyl compound described in [1] above, in which $R^1$ and $R^2$ are Me, Y is H, W is a chemical bond, A is A-1, any of D, E, F and G is CH, $R^3$ is Cl or Br, and $R^4$ is Cl or Br.

[37] An agricultural chemical containing as the active ingredient at least one sulfamoyl compound described in [1] to [36] above.

[38] An agricultural chemical as described in [37] above, in which the agricultural chemical is an agricultural and horticultural fungicide.

In the compounds of the general formula (1), examples of $C_{1-4}$ alkyl for $R^1$ and $R^2$ are methyl, ethyl, n- or i-propyl, n-, i- or s-butyl and the like.

Examples of $C_{4-6}$ alkylene formed by $R^1$ and $R^2$ together are piperidine including the N to which $R^1$ and $R^2$ are bonded and the like.

Examples of $C_{4-6}$ alkyleneoxy formed by $R^1$ and $R^2$ together are morpholine including the N to which $R^1$ and $R^2$ are bonded and the like.

The definitions of substituents Y, $R^3$, $R^4$, $R^5$, $R^6$, $R^7$, $R^8$, $R^9$, $R^{10}$ and $R^{11}$ have following meanings.

Examples of $C_{1-8}$ alkyl are methyl, ethyl, n- or i-propyl, n- or i-butyl, n-pentyl and the like.

Examples of $C_{3-8}$ cycloalkyl are cyclopropyl, cyclobutyl, cyclopentyl, cyclohexyl and the like.

Examples of $C_{2-8}$ alkenyl are allyl, vinyl and the like.

Examples of $C_{5-8}$ cycloalkenyl are cyclopentenyl and the like.

Examples of $C_{2-8}$ alkynyl are propargyl and the like.

Examples of $C_{1-8}$ alkoxy are methoxy, ethoxy and the like.

Examples of $C_{3-8}$ cycloalkyloxy are cyclopropyloxy and the like.

Examples of $C_{3-8}$ cycloalkenyloxy are cyclopentenyl-3-oxy and the like.

Examples of $C_{2-8}$ alkenyloxy are allyloxy and the like.

Examples of $C_{2-8}$ alkynyloxy are propargyloxy and the like.

Examples of $C_{1-8}$ alkylthio are methylthio, ethylthio, n- or i-propylthio and the like.

Examples of $C_{3-8}$ cycloalkylthio are cyclopentylthio and the like.

Examples of $C_{3-8}$ cycloalkenylthio are cyclopentenyl-3-thio and the like.

Examples of $C_{2-8}$ alkenylthio are allylthio and the like.

Examples of $C_{2-8}$ alkynylthio are propargylthio and the like.

Examples of $C_{1-8}$ haloalkoxy are trifluoromethoxy and the like.

Examples of $C_{1-8}$ haloalkylthio are trifluoromethylthio and the like.

Examples of $C_{1-8}$ haloalkyl are chloromethyl, dichloromethyl, dichlorofluoromethyl, trifluoromethyl and the like.

Examples of $C_{2-8}$ haloalkenyl are 3-chloroallyl and the like.

Examples of $C_{2-8}$ haloalkenyloxy are 3-chloroallyloxy and the like.

Examples of $C_{2-8}$ haloalkenylthio are 3-chloroallylthio and the like.

Examples of $C_{2-8}$ haloalkynyl are iodopropargyl and the like.

Examples of $C_{2-8}$ haloalkynyloxy are iodopropargyloxy and the like.

Examples of $C_{2-8}$ haloalkynylthio are iodopropargylthio and the like.

Examples of $C_{1-8}$ hydroxyalkyl are hydroxymethyl, 1-hydroxyethyl and the like.

Examples of $C_{1-8}$ hydroxyhaloalkyl are 2,2,2-trifluoro-1-hydroxyethyl and the like.

Examples of $C_{1-6}$ alkoxy $C_{1-4}$ alkyl are methoxymethyl, methoxyethyl and the like.

Examples of $C_{1-6}$ haloalkoxy $C_{1-4}$ alkyl are trifluoroethoxymethyl and the like.

Examples of $C_{1-6}$ alkylthio $C_{1-4}$ alkyl are methylthiomethyl, ethylthiomethyl, methylthioethyl and the like.

Examples of $C_{1-6}$ haloalkylthio $C_{1-4}$ alkyl are trifluoroethylthiomethyl and the like.

Examples of $C_{1-10}$ dialkoxy $C_{1-4}$ alkyl are dimethoxymethyl, diethoxymethyl and the like.

Examples of $C_{1-10}$ dialkylthio $C_{1-4}$ alkyl are dimethylthiomethyl, diethylthiomethyl and the like.

Examples of $C_{1-3}$ alkylenedioxy $C_{1-4}$ alkyl are ethylenedioxymethyl and the like.

Examples of $C_{1-3}$ alkylenedithio $C_{1-4}$ alkyl are ethylenedithiomethyl and the like.

Examples of phenoxy $C_{1-4}$ alkyl which may be substituted are phenoxymethyl and the like.

Examples of phenoxy which may be substituted are phenoxy and the like.

Examples of phenylthio $C_{1-4}$ alkyl which may be substituted are phenylthiomethyl and the like.

Examples of phenylthio which may be substituted are phenylthio and the like.

Examples of phenyl $C_{1-4}$ alkyl which may be substituted are benzyl, phenethyl and the like.

Examples of benzylthio which may be substituted are benzylthio and the like.

Examples of benzyloxy which may be substituted are benzyloxy and the like.

Examples of phenyl which may be substituted are phenyl and the like.

Examples of benzoyl which may be substituted are benzoyl and the like.

Examples of benzoyl $C_{1-4}$ alkyl which may be substituted are benzoylmethyl and the like.

Examples of benzoyloxy which may be substituted are benzoyloxy and the like.

Examples of benzoyloxy $C_{1-4}$ alkyl which may be substituted are benzoyloxymethyl and the like.

Examples of naphthyl which may be substituted are naphthyl and the like.

Examples of 5- or 6-memberedheterocyclic ring are pyridine, thiophene, furan, thiazole and the like.

Examples of $C_{1-6}$ alkoxycarbonyl are methoxycarbonyl and the like.

Examples of $C_{1-6}$ alkoxycarbonyl $C_{1-4}$ alkyl are methoxycarbonylmethyl and the like.

Examples of $C_{1-6}$ haloalkoxycarbonyl are fluoroethoxycarbonyl and the like.

Examples of $C_{1-6}$ haloalkoxycarbonyl $C_{1-4}$ alkyl are fluoroethoxycarbonylmethyl and the like.

Examples of $C_{1-6}$ alkoxyoxalyl are methoxyoxalyl, ethoxyoxalyl and the like.

Examples of $C_{1-6}$ dialkylamino are dimethylamino and the like.

Examples of $C_{1-6}$ alkylamino are methylamino and the like.

Examples of $C_{1-6}$ dialkylamino $C_{1-4}$ alkyl are dimethylaminomethyl and the like.

Examples of $C_{2-6}$ alkyleneimino are pyrrolidino, piperidino and the like.

Examples of $C_{2-6}$ alkyleneiminocarbonyl are pyrrolidinocarbonyl, piperidinocarbonyl and the like.

Examples of $C_{2-6}$ alkyleneimino $C_{1-4}$ alkyl are pyrrolidinomethyl, piperidinomethyl and the like.

Examples of $C_{2-6}$ alkyleneiminocarbonyl $C_{1-4}$ alkyl are pyrrolidinocarbonylmethyl, piperidinocarbonylmethyl and the like.

Examples of $C_{1-6}$ alkylcarbonylamino are acethylamino and the like.

Examples of $C_{1-6}$ alkoxycarbonylamino are methoxycarbonylamino and the like.

Examples of $C_{1-6}$ haloalkylcarbonylamino are trifluoroacethylamino and the like.

Examples of $C_{1-6}$ alkylsulfonylamino are methanesulfonylamino and the like.

Examples of $C_{1-6}$ haloalkylsulfonylamino are chloromethylsulfonylamino and the like.

Examples of $C_{1-6}$ alkylcarbonylamino $C_{1-4}$ alkyl are acetylaminomethyl and the like.

Examples of $C_{1-6}$ alkoxycarbonylamino $C_{1-4}$ alkyl are methoxycarbonylaminomethyl and the like.

Examples of $C_{1-6}$ haloalkylcarbonylamino $C_{1-4}$ alkyl are trifluoroacetylaminomethyl and the like.

Examples of $C_{1-6}$ alkylsulfonylamino $C_{1-4}$ alkyl are methanesulfonylaminomethyl and the like.

Examples of $C_{1-6}$ haloalkylsulfonylamino $C_{1-4}$ alkyl are chloromethylsulfonylaminomethyl and the like.

Examples of $C_{1-6}$ dialkylaminocarbonyl are dimethylaminocarbonyl and the like.

Examples of $C_{1-6}$ dialkylaminocarbonyl $C_{1-4}$ alkyl are dimethylaminocarbonylmethyl and the like.

Examples of $C_{1-6}$ alkylcarbonyl are acetyl and the like.

Examples of $C_{1-6}$ haloalkylcarbonyl are trifluoroacetyl and the like.

Examples of $C_{1-6}$ alkylcarbonyloxy are acetyloxy and the like.

Examples of $C_{1-6}$ haloalkylcarbonyloxy are trifluoroacetyloxy and the like.

Examples of $C_{1-6}$ alkylcarbonyl $C_{1-4}$ alkyl are acetylmethyl and the like.

Examples of $C_{1-6}$ haloalkylcarbonyl $C_{1-4}$ alkyl are trifluoroacetylmethyl and the like.

Examples of $C_{1-6}$ alkylcarbonyloxy $C_{1-4}$ alkyl are acetyloxymethyl and the like.

Examples of $C_{1-6}$ haloalkylcarbonyloxy $C_{1-4}$ alkyl are trifluoroacetyloxymethyl and the like.

Examples of hydroxyimino $C_{1-4}$ alkyl are hydroxyiminomethyl and the like.

Examples of alkoxyimino $C_{1-4}$ alkyl are methoxyiminomethyl and the like.

Examples of $C_{1-6}$ alkylcarbonyloxyimino $C_{1-4}$ alkyl are acetyloxyiminomethyl and the like.

Examples of $C_{1-6}$ alkylsulfonyloxyimino $C_{1-4}$ alkyl are methanesulfonyloxyiminomethyl and the like.

Examples of $C_{1-6}$ alkylsulfoxy are methylsulfoxy and the like.

Examples of $C_{1-6}$ alkylsulfoxy $C_{1-4}$ alkyl are methylsulfoxymethyl, ethylsulfoxymethyl, methylsulfoxyethyl and the like.

Examples of $C_{1-6}$ alkylsulfonyl are methanesulfonyl and the like.

Examples of $C_{1-6}$ alkylsulfonyloxy are methanesulfonyloxy and the like.

Examples of $C_{1-6}$ alkylsulfonyl $C_{1-4}$ alkyl are methylsulfonylmethyl, ethylsulfonylmethyl, methylsulfonylethyl and the like.

Examples of $C_{1-6}$ alkylsulfonyloxy $C_{1-4}$ alkyl are methylsulfonyloxymethyl and the like.

Examples of $C_{1-6}$ haloalkylsulfoxy are chloromethylsulfoxy and the like.

Examples of $C_{1-6}$ haloalkylsulfoxy $C_{1-4}$ alkyl are chloromethylsulfoxymethyl and the like.

Examples of $C_{1-6}$ haloalkylsulfonyl are trifluoromethylsulfonyl and the like.

Examples of $C_{1-6}$ haloalkylsulfonyloxy are trifluoromethylsulfonyloxy and the like.

Examples of $C_{1-6}$ haloalkylsulfonyl $C_{1-4}$ alkyl are trifluoromethylsulfonylmethyl and the like.

Examples of $C_{1-6}$ haloalkylsulfonyloxy $C_{1-4}$ alkyl are trifluoromethylsulfonyloxymethyl and the like.

Examples of $C_{1-6}$ dialkylsulfamoyl are dimethylsulfamoyl and the like.

Examples of $C_{1-6}$ dialkylsulfamoyl $C_{1-4}$ alkyl are dimethylsulfamoylmethyl and the like.

Examples of $C_{1-6}$ alkoxysulfonyl are methoxysulfonyl and the like.

Examples of $C_{1-6}$ alkoxysulfonyl $C_{1-4}$ alkyl are methoxysulfonylmethyl and the like.

Examples of $C_{1-6}$ haloalkoxysulfonyl are fluoroethoxysulfonyl and the like.

Examples of $C_{1-6}$ haloalkoxysulfonyl $C_{1-4}$ alkyl are fluoroethoxysulfonylmethyl and the like.

Examples of $C_{1-6}$ nitroalkyl are nitromethyl and the like.

Examples of $C_{2-6}$ are cyanomethyl and the like.

Examples of $C_{1-6}$ thiocarbamoyl are $CSNH_2$ and the like.

Examples of halogen are F, Cl, Br and I.

Examples of $C_{1-3}$ alkylenedioxy which may be substituted with halogen are diflouromethylenedioxy, tetrafluoroethylenedioxy and the like.

Next, the compounds of the invention of the formula (1) are shown in Tables 1 to 11. However, the present invention should not be construed as being limited thereto.

In the Tables, Me denotes methyl, Et denotes ethyl, Pr denotes propyl, Bu denotes butyl, n- denotes normal, i- denotes iso, s- denotes secondary, t- denotes tertiary, Ph denotes phenyl, Bn denotes benzyl, and Ac denotes acetyl.

TABLE 1

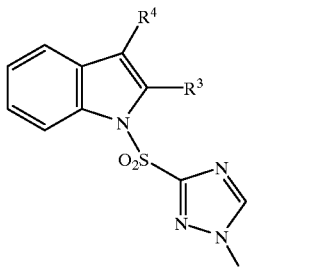

(a)

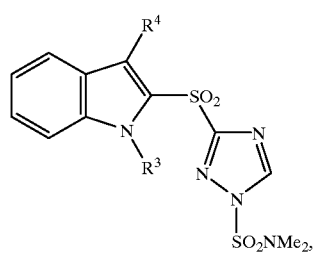

(b)

TABLE 1-continued

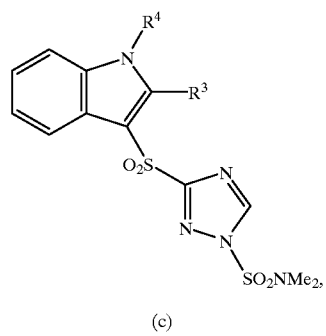

(c)

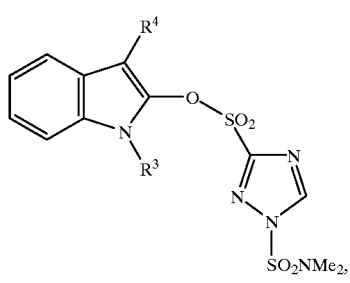

(d)

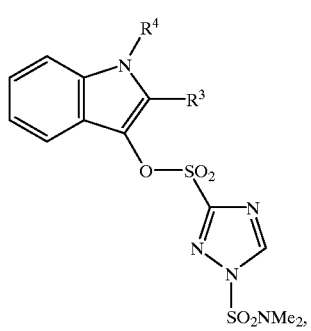

(e)

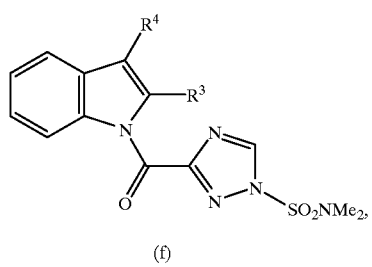

(f)

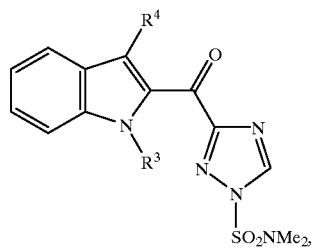

(g)

TABLE 1-continued

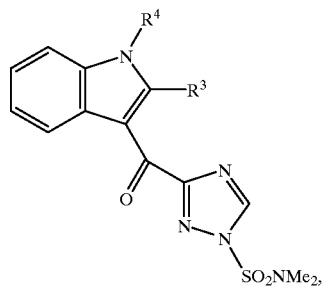

(h)

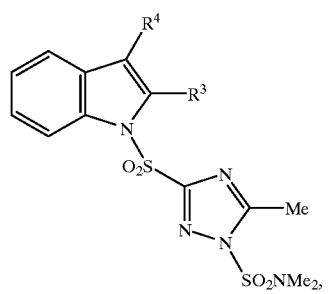

(i)

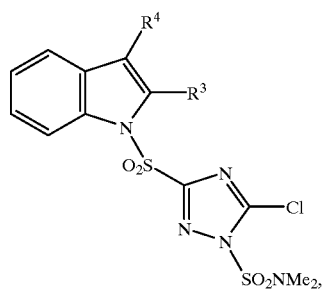

(j)

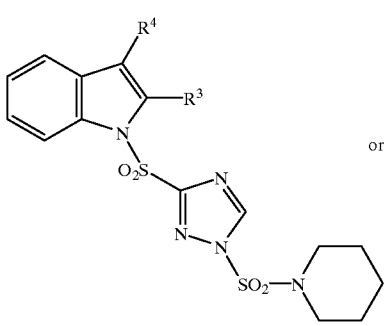

(k)

TABLE 1-continued

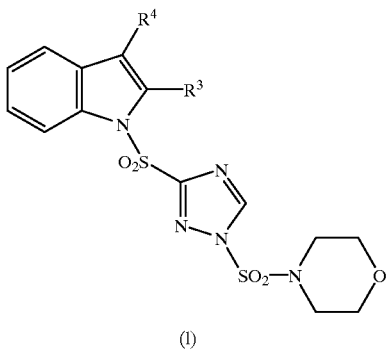

(l)

| Compound No. | R³ | R⁴ |
|---|---|---|
| 1-1 | H | H |
| 1-2 | Me | H |
| 1-3 | Et | H |
| 1-4 | n-Pr | H |
| 1-5 | i-Pr | H |
| 1-6 | n-Bu | H |
| 1-7 | Ph | H |
| 1-8 | Bn | H |
| 1-9 | F | H |
| 1-10 | Cl | H |
| 1-11 | Br | H |
| 1-12 | I | H |
| 1-13 | SMe | H |
| 1-14 | SEt | H |
| 1-15 | $CH_2OMe$ | H |
| 1-16 | $CClF_2$ | H |
| 1-17 | $CHF_2$ | H |
| 1-18 | CHFCl | H |
| 1-19 | $CH_2Cl$ | H |
| 1-20 | $CF_3$ | H |
| 1-21 | CN | H |
| 1-22 | CHO | H |
| 1-23 | $C_2F_5$ | H |
| 1-24 | CH=NOMe | H |
| 1-25 | $CO_2Me$ | H |
| 1-26 | $CO_2Et$ | H |
| 1-27 | $CONMe_2$ | H |
| 1-28 | COMe | H |
| 1-29 | COPh | H |
| 1-30 | $CH_2CO_2Me$ | H |
| 1-31 | $NO_2$ | H |
| 1-32 | H | Cl |
| 1-33 | Me | Cl |
| 1-34 | Et | Cl |
| 1-35 | n-Pr | Cl |
| 1-36 | i-Pr | Cl |
| 1-37 | n-Bu | Cl |
| 1-38 | Ph | Cl |
| 1-39 | Bn | Cl |
| 1-40 | F | Cl |
| 1-41 | Cl | Cl |
| 1-42 | Br | Cl |
| 1-43 | I | Cl |
| 1-44 | SMe | Cl |
| 1-45 | SEt | Cl |
| 1-46 | $CH_2OMe$ | Cl |
| 1-47 | $CHF_2$ | Cl |
| 1-48 | CHFCl | Cl |
| 1-49 | $CH_2Cl$ | Cl |
| 1-50 | $CF_3$ | Cl |
| 1-51 | CN | Cl |
| 1-52 | CHO | Cl |
| 1-53 | $C_2F_5$ | Cl |
| 1-54 | CH=NOMe | Cl |
| 1-55 | $CO_2Me$ | Cl |
| 1-56 | $CO_2Et$ | Cl |
| 1-57 | $CONMe_2$ | Cl |
| 1-58 | COMe | Cl |
| 1-59 | $CClF_2$ | Cl |

TABLE 1-continued

| | | |
|---|---|---|
| 1-60 | CH$_2$CO$_2$Me | Cl |
| 1-61 | NO$_2$ | Cl |
| 1-62 | H | Br |
| 1-63 | Me | Br |
| 1-64 | Et | Br |
| 1-65 | n-Pr | Br |
| 1-66 | i-Pr | Br |
| 1-67 | n-Bu | Br |
| 1-68 | Ph | Br |
| 1-69 | Bn | Br |
| 1-70 | F | Br |
| 1-71 | Cl | Br |
| 1-72 | Br | Br |
| 1-73 | I | Br |
| 1-74 | SMe | Br |
| 1-75 | SEt | Br |
| 1-76 | CH$_2$OMe | Br |
| 1-77 | CHF$_2$ | Br |
| 1-78 | CHFCl | Br |
| 1-79 | CH$_2$Cl | Br |
| 1-80 | CF$_3$ | Br |
| 1-81 | CN | Br |
| 1-82 | CHO | Br |
| 1-83 | C$_2$F$_5$ | Br |
| 1-84 | CH=NOMe | Br |
| 1-85 | CO$_2$Me | Br |
| 1-86 | CO$_2$Et | Br |
| 1-87 | CONMe$_2$ | Br |
| 1-88 | COMe | Br |
| 1-89 | CClF$_2$ | Br |
| 1-90 | CH$_2$CO$_2$Me | Br |
| 1-91 | NO$_2$ | Br |
| 1-92 | H | I |
| 1-93 | Me | I |
| 1-94 | Et | I |
| 1-95 | n-Pr | I |
| 1-96 | n-Bu | I |
| 1-97 | Ph | I |
| 1-98 | F | I |
| 1-99 | Cl | I |
| 1-100 | Br | I |
| 1-101 | I | I |
| 1-102 | SMe | I |
| 1-103 | CF$_3$ | I |
| 1-104 | CN | I |
| 1-105 | H | F |
| 1-106 | Me | F |
| 1-107 | Et | F |
| 1-108 | n-Pr | F |
| 1-109 | n-Bu | F |
| 1-110 | Ph | F |
| 1-111 | F | F |
| 1-112 | Cl | F |
| 1-113 | Br | F |
| 1-114 | CO$_2$Et | F |
| 1-115 | SMe | F |
| 1-116 | CF$_3$ | F |
| 1-117 | CN | F |
| 1-118 | H | Me |
| 1-119 | Me | Me |
| 1-120 | Et | Me |
| 1-121 | n-Pr | Me |
| 1-122 | CF$_2$Cl | Me |
| 1-123 | CHF$_2$ | Me |
| 1-124 | F | Me |
| 1-125 | Cl | Me |
| 1-126 | Br | Me |
| 1-127 | I | Me |
| 1-128 | SMe | Me |
| 1-129 | CF$_3$ | Me |
| 1-130 | CN | Me |
| 1-131 | CHO | Me |
| 1-132 | CH=NOH | Me |
| 1-133 | CH=NOMe | Me |
| 1-134 | CH=NOAc | Me |
| 1-135 | H | Et |
| 1-136 | Me | Et |
| 1-137 | Et | Et |
| 1-138 | n-Pr | Et |
| 1-139 | F | Et |
| 1-140 | Cl | Et |
| 1-141 | Br | Et |
| 1-142 | CHF$_2$ | Et |
| 1-143 | CClF$_2$ | Et |
| 1-144 | CF$_3$ | Et |
| 1-145 | CN | Et |
| 1-146 | CHO | Et |
| 1-147 | —(CH$_2$)$_3$— | |
| 1-148 | —(CH$_2$)$_4$— | |
| 1-149 | —(CH$_2$)$_5$— | |
| 1-150 | —(CH$_2$)$_6$— | |
| 1-151 | H | Ph |
| 1-152 | Me | Ph |
| 1-153 | Et | Ph |
| 1-154 | n-Pr | Ph |
| 1-155 | F | Ph |
| 1-156 | Cl | Ph |
| 1-157 | Br | Ph |
| 1-158 | I | Ph |
| 1-159 | SMe | Ph |
| 1-160 | CF$_3$ | Ph |
| 1-161 | CN | Ph |
| 1-162 | CHO | Ph |
| 1-163 | H | Bn |
| 1-164 | Me | Bn |
| 1-165 | Et | Bn |
| 1-166 | n-Pr | Bn |
| 1-167 | F | Bn |
| 1-168 | Cl | Bn |
| 1-169 | Br | Bn |
| 1-170 | I | Bn |
| 1-171 | SMe | Bn |
| 1-172 | CF$_3$ | Bn |
| 1-173 | CN | Bn |
| 1-174 | H | CF$_3$ |
| 1-175 | Me | CF$_3$ |
| 1-176 | Et | CF$_3$ |
| 1-177 | n-Pr | CF$_3$ |
| 1-178 | n-Bu | CF$_3$ |
| 1-179 | Ph | CF$_3$ |
| 1-180 | F | CF$_3$ |
| 1-181 | Cl | CF$_3$ |
| 1-182 | Br | CF$_3$ |
| 1-183 | I | CF$_3$ |
| 1-184 | SMe | CF$_3$ |
| 1-185 | CF$_3$ | CF$_3$ |
| 1-186 | CN | CF$_3$ |
| 1-187 | H | CHO |
| 1-188 | Me | CHO |
| 1-189 | Et | CHO |
| 1-190 | n-Pr | CHO |
| 1-191 | n-Bu | CHO |
| 1-192 | F | CHO |
| 1-193 | Cl | CHO |
| 1-194 | Br | CHO |
| 1-195 | I | CHO |
| 1-196 | SMe | CHO |
| 1-197 | CF$_3$ | CHO |
| 1-198 | CN | CHO |
| 1-199 | H | CH=NOH |
| 1-200 | Me | CH=NOH |
| 1-201 | Et | CH=NOH |
| 1-202 | n-Pr | CH=NOH |
| 1-203 | F | CH=NOH |
| 1-204 | Cl | CH=NOH |
| 1-205 | Br | CH=NOH |
| 1-206 | I | CH=NOH |
| 1-207 | SMe | CH=NOH |
| 1-208 | CF$_3$ | CH=NOH |
| 1-209 | CN | CH=NOH |
| 1-210 | H | CH=NOMe |
| 1-211 | Me | CH=NOMe |
| 1-212 | Et | CH=NOMe |
| 1-213 | n-Pr | CH=NOMe |
| 1-214 | F | CH=NOMe |
| 1-215 | Cl | CH=NOMe |
| 1-216 | Br | CH=NOMe |
| 1-217 | I | CH=NOMe |

TABLE 1-continued

| | | |
|---|---|---|
| 1-218 | SMe | CH=NOMe |
| 1-219 | CF$_3$ | CH=NOMe |
| 1-220 | CN | CH=NOMe |
| 1-221 | H | CH=NOAc |
| 1-222 | Me | CH=NOAc |
| 1-223 | Et | CH=NOAc |
| 1-224 | n-Pr | CH=NOAc |
| 1-225 | F | CH=NOAc |
| 1-226 | Cl | CH=NOAc |
| 1-227 | Br | CH=NOAc |
| 1-228 | I | CH=NOAc |
| 1-229 | SMe | CH=NOAc |
| 1-230 | CF$_3$ | CH=NOAc |
| 1-231 | CN | CH=NOAc |
| 1-232 | H | COMe |
| 1-233 | Me | COMe |
| 1-234 | Et | COMe |
| 1-235 | n-Pr | COMe |
| 1-236 | n-Bu | COMe |
| 1-237 | F | COMe |
| 1-238 | Cl | COMe |
| 1-239 | Br | COMe |
| 1-240 | I | COMe |
| 1-241 | SMe | COMe |
| 1-242 | CF$_3$ | COMe |
| 1-243 | CN | COMe |
| 1-244 | H | COEt |
| 1-245 | Me | COEt |
| 1-246 | Et | COEt |
| 1-247 | n-Pr | COEt |
| 1-248 | n-Bu | COEt |
| 1-249 | Ph | COEt |
| 1-250 | F | COEt |
| 1-251 | Cl | COEt |
| 1-252 | Br | COEt |
| 1-253 | I | COEt |
| 1-254 | SMe | COEt |
| 1-255 | CF$_3$ | COEt |
| 1-256 | CN | COEt |
| 1-257 | H | COPh |
| 1-258 | Me | COPh |
| 1-259 | Et | COPh |
| 1-260 | n-Pr | COPh |
| 1-261 | F | COPh |
| 1-262 | Cl | COPh |
| 1-263 | Br | COPh |
| 1-264 | I | COPh |
| 1-265 | H | COCF$_3$ |
| 1-266 | Me | COCF$_3$ |
| 1-267 | Et | COCF$_3$ |
| 1-268 | n-Pr | COCF$_3$ |
| 1-269 | F | COCF$_3$ |
| 1-270 | Cl | COCF$_3$ |
| 1-271 | Br | COCF$_3$ |
| 1-272 | I | COCF$_3$ |
| 1-273 | SMe | COCF$_3$ |
| 1-274 | CF$_3$ | COCF$_3$ |
| 1-275 | CN | COCF$_3$ |
| 1-276 | H | CO$_2$Me |
| 1-277 | Me | CO$_2$Me |
| 1-278 | Et | CO$_2$Me |
| 1-279 | n-Pr | CO$_2$Me |
| 1-280 | n-Bu | CO$_2$Me |
| 1-281 | Ph | CO$_2$Me |
| 1-282 | F | CO$_2$Me |
| 1-283 | Cl | CO$_2$Me |
| 1-284 | Br | CO$_2$Me |
| 1-285 | I | CO$_2$Me |
| 1-286 | SMe | CO$_2$Me |
| 1-287 | CF$_3$ | CO$_2$Me |
| 1-288 | CN | CO$_2$Me |
| 1-289 | H | CO$_2$Et |
| 1-290 | Me | CO$_2$Et |
| 1-291 | Et | CO$_2$Et |
| 1-292 | F | CO$_2$Et |
| 1-293 | Cl | CO$_2$Et |
| 1-294 | Br | CO$_2$Et |
| 1-295 | SMe | CO$_2$Et |
| 1-296 | CF$_3$ | CO$_2$Et |
| 1-297 | CN | CO$_2$Et |
| 1-298 | H | CO$_2$n-Pr |
| 1-299 | Me | CO$_2$n-Pr |
| 1-300 | Et | CO$_2$n-Pr |
| 1-301 | F | CO$_2$n-Pr |
| 1-302 | Cl | CO$_2$n-Pr |
| 1-303 | Br | CO$_2$n-Pr |
| 1-304 | SMe | CO$_2$n-Pr |
| 1-305 | CF$_3$ | CO$_2$n-Pr |
| 1-306 | CN | CO$_2$n-Pr |
| 1-307 | H | CO$_2$I-Pr |
| 1-309 | Et | CO$_2$I-Pr |
| 1-310 | F | CO$_2$I-Pr |
| 1-311 | Cl | CO$_2$I-Pr |
| 1-312 | Br | CO$_2$I-Pr |
| 1-313 | SMe | CO$_2$I-Pr |
| 1-314 | CF$_3$ | CO$_2$I-Pr |
| 1-315 | CN | CO$_2$I-Pr |
| 1-316 | H | CO$_2$n-Bu |
| 1-317 | Me | CO$_2$n-Bu |
| 1-318 | Et | CO$_2$n-Bu |
| 1-319 | F | CO$_2$n-Bu |
| 1-320 | Cl | CO$_2$n-Bu |
| 1-321 | Br | CO$_2$n-Bu |
| 1-322 | SMe | CO$_2$n-Bu |
| 1-323 | CF$_3$ | CO$_2$n-Bu |
| 1-324 | CN | CO$_2$n-Bu |
| 1-325 | H | CO$_2$I-Bu |
| 1-326 | Me | CO$_2$I-Bu |
| 1-327 | Et | CO$_2$I-Bu |
| 1-328 | F | CO$_2$I-Bu |
| 1-329 | Cl | CO$_2$I-Bu |
| 1-330 | Br | CO$_2$I-Bu |
| 1-331 | SMe | CO$_2$I-Bu |
| 1-332 | CF$_3$ | CO$_2$I-Bu |
| 1-333 | CN | CO$_2$I-Bu |
| 1-334 | H | CO$_2$s-Bu |
| 1-335 | Me | CO$_2$s-Bu |
| 1-336 | Et | CO$_2$s-Bu |
| 1-337 | F | CO$_2$s-Bu |
| 1-338 | Cl | CO$_2$s-Bu |
| 1-339 | Br | CO$_2$s-Bu |
| 1-340 | SMe | CO$_2$s-Bu |
| 1-341 | CF$_3$ | CO$_2$s-Bu |
| 1-342 | CN | CO$_2$s-Bu |
| 1-343 | H | CO$_2$t-Bu |
| 1-344 | Me | CO$_2$t-Bu |
| 1-345 | Et | CO$_2$t-Bu |
| 1-346 | F | CO$_2$t-Bu |
| 1-347 | Cl | CO$_2$t-Bu |
| 1-348 | Br | CO$_2$t-Bu |
| 1-349 | SMe | CO$_2$t-Bu |
| 1-350 | CF$_3$ | CO$_2$t-Bu |
| 1-351 | CN | CO$_2$t-Bu |
| 1-352 | H | CO$_2$Ph |
| 1-353 | Me | CO$_2$Ph |
| 1-354 | Et | CO$_2$Ph |
| 1-355 | F | CO$_2$Ph |
| 1-356 | Cl | CO$_2$Ph |
| 1-357 | Br | CO$_2$Ph |
| 1-358 | SMe | CO$_2$Ph |
| 1-359 | CF$_3$ | CO$_2$Ph |
| 1-360 | CN | CO$_2$Ph |
| 1-361 | H | COCO$_2$Me |
| 1-362 | Me | COCO$_2$Me |
| 1-363 | F | COCO$_2$Me |
| 1-364 | Cl | COCO$_2$Me |
| 1-365 | Br | COCO$_2$Me |
| 1-366 | SMe | COCO$_2$Me |
| 1-367 | CF$_3$ | COCO$_2$Me |
| 1-368 | CN | COCO$_2$Me |
| 1-369 | H | COCO$_2$Et |
| 1-370 | Me | COCO$_2$Et |
| 1-371 | F | COCO$_2$Et |
| 1-372 | Cl | COCO$_2$Et |
| 1-373 | Br | COCO$_2$Et |
| 1-374 | SMe | COCO$_2$Et |
| 1-375 | CF$_3$ | COCO$_2$Et |
| 1-376 | CN | COCO$_2$Et |

TABLE 1-continued

| | | |
|---|---|---|
| 1-377 | H | SMe |
| 1-378 | Me | SMe |
| 1-379 | Et | SMe |
| 1-380 | n-Pr | SMe |
| 1-381 | F | SMe |
| 1-382 | Cl | SMe |
| 1-383 | Br | SMe |
| 1-384 | I | SMe |
| 1-385 | SMe | SMe |
| 1-386 | $CF_3$ | SMe |
| 1-387 | CN | SMe |
| 1-388 | H | SOMe |
| 1-389 | Me | SOMe |
| 1-390 | Et | SOMe |
| 1-391 | Cl | SOMe |
| 1-392 | Br | SOMe |
| 1-393 | $CF_3$ | SOMe |
| 1-394 | CN | SOMe |
| 1-395 | H | $SO_2Me$ |
| 1-396 | Me | $SO_2Me$ |
| 1-397 | Et | $SO_2Me$ |
| 1-398 | Cl | $SO_2Me$ |
| 1-399 | Br | $SO_2Me$ |
| 1-400 | $CF_3$ | $SO_2Me$ |
| 1-401 | CN | $SO_2Me$ |
| 1-402 | H | SPh |
| 1-403 | Me | SPh |
| 1-404 | Et | SPh |
| 1-405 | n-Pr | SPh |
| 1-406 | F | SPh |
| 1-407 | Cl | SPh |
| 1-408 | Br | SPh |
| 1-409 | I | SPh |
| 1-410 | SMe | SPh |
| 1-411 | $CF_3$ | SPh |
| 1-412 | CN | SPh |
| 1-413 | H | SOPh |
| 1-414 | Me | SOPh |
| 1-415 | Et | SOPh |
| 1-416 | Cl | SOPh |
| 1-417 | Br | SOPh |
| 1-418 | $CF_3$ | SOPh |
| 1-419 | CN | SOPh |
| 1-420 | H | $SO_2Ph$ |
| 1-421 | Me | $SO_2Ph$ |
| 1-422 | Et | $SO_2Ph$ |
| 1-423 | Cl | $SO_2Ph$ |
| 1-424 | Br | $SO_2Ph$ |
| 1-425 | $CF_3$ | $SO_2Ph$ |
| 1-426 | CN | $SO_2Ph$ |
| 1-427 | H | $NO_2$ |
| 1-428 | Me | $NO_2$ |
| 1-429 | Et | $NO_2$ |
| 1-430 | Cl | $NO_2$ |
| 1-431 | Br | $NO_2$ |
| 1-432 | SMe | $NO_2$ |
| 1-433 | $CF_3$ | $NO_2$ |
| 1-434 | CN | $NO_2$ |
| 1-435 | H | CN |
| 1-436 | Me | CN |
| 1-437 | Et | CN |
| 1-438 | n-Pr | CN |
| 1-439 | F | CN |
| 1-440 | Cl | CN |
| 1-441 | Br | CN |
| 1-442 | SMe | CN |
| 1-443 | $CF_3$ | CN |
| 1-444 | CN | CN |
| 1-445 | H | $CH_2CN$ |
| 1-446 | Me | $CH_2CN$ |
| 1-447 | Et | $CH_2CN$ |
| 1-448 | n-Pr | $CH_2CN$ |
| 1-449 | Cl | $CH_2CN$ |
| 1-450 | Br | $CH_2CN$ |
| 1-451 | SMe | $CH_2CN$ |
| 1-452 | $CF_3$ | $CH_2CN$ |
| 1-453 | CN | $CH_2CN$ |
| 1-454 | H | OMe |
| 1-455 | Me | OMe |

TABLE 1-continued

| | | |
|---|---|---|
| 1-456 | Et | OMe |
| 1-457 | Cl | OMe |
| 1-458 | Br | OMe |
| 1-459 | SMe | OMe |
| 1-460 | $CF_3$ | OMe |
| 1-461 | CN | OMe |
| 1-462 | H | $CH_2NMe_2$ |
| 1-463 | Me | $CH_2NMe_2$ |
| 1-464 | Et | $CH_2NMe_2$ |
| 1-465 | Cl | $CH_2NMe_2$ |
| 1-466 | Br | $CH_2NMe_2$ |
| 1-467 | SMe | $CH_2NMe_2$ |
| 1-468 | $CF_3$ | $CH_2NMe_2$ |
| 1-469 | CN | $CH_2NMe_2$ |
| 1-470 | H | OCOMe |
| 1-471 | Me | OCOMe |
| 1-472 | Et | OCOMe |
| 1-473 | Cl | OCOMe |
| 1-474 | Br | OCOMe |
| 1-475 | SMe | OCOMe |
| 1-476 | $CF_3$ | OCOMe |
| 1-477 | CN | OCOMe |
| 1-478 | H | $CH(OMe)_2$ |
| 1-479 | Me | $CH(OMe)_2$ |
| 1-480 | Et | $CH(OMe)_2$ |
| 1-481 | n-Pr | $CH(OMe)_2$ |
| 1-482 | Cl | $CH(OMe)_2$ |
| 1-483 | Br | $CH(OMe)_2$ |
| 1-484 | SMe | $CH(OMe)_2$ |
| 1-485 | $CF_3$ | $CH(OMe)_2$ |
| 1-486 | CN | $CH(OMe)_2$ |
| 1-487 | H | $CH(SMe)_2$ |
| 1-488 | Me | $CH(SMe)_2$ |
| 1-489 | Et | $CH(SMe)_2$ |
| 1-490 | n-Pr | $CH(SMe)_2$ |
| 1-491 | Cl | $CH(SMe)_2$ |
| 1-492 | Br | $CH(SMe)_2$ |
| 1-493 | SMe | $CH(SMe)_2$ |
| 1-494 | $CF_3$ | $CH(SMe)_2$ |
| 1-495 | CN | $CH(SMe)_2$ |
| 1-496 | H | $CH_2Cl$ |
| 1-497 | Me | $CH_2Cl$ |
| 1-498 | Et | $CH_2Cl$ |
| 1-499 | n-Pr | $CH_2Cl$ |
| 1-500 | F | $CH_2Cl$ |
| 1-501 | Cl | $CH_2Cl$ |
| 1-502 | Br | $CH_2Cl$ |
| 1-503 | I | $CH_2Cl$ |
| 1-504 | SMe | $CH_2Cl$ |
| 1-505 | $CF_3$ | $CH_2Cl$ |
| 1-506 | CN | $CH_2Cl$ |
| 1-507 | H | $CH_2OH$ |
| 1-508 | Me | $CH_2OH$ |
| 1-509 | Et | $CH_2OH$ |
| 1-510 | n-Pr | $CH_2OH$ |
| 1-511 | F | $CH_2OH$ |
| 1-512 | Cl | $CH_2OH$ |
| 1-513 | Br | $CH_2OH$ |
| 1-514 | SMe | $CH_2OH$ |
| 1-515 | $CF_3$ | $CH_2OH$ |
| 1-516 | CN | $CH_2OH$ |
| 1-517 | H | CH(OH)Me |
| 1-518 | Me | CH(OH)Me |
| 1-519 | Et | CH(OH)Me |
| 1-520 | n-Pr | CH(OH)Me |
| 1-521 | F | CH(OH)Me |
| 1-522 | Cl | CH(OH)Me |
| 1-523 | Br | CH(OH)Me |
| 1-524 | SMe | CH(OH)Me |
| 1-525 | $CF_3$ | CH(OH)Me |
| 1-526 | CN | CH(OH)Me |
| 1-527 | H | CH(OH)Et |
| 1-528 | Me | CH(OH)Et |
| 1-529 | Et | CH(OH)Et |
| 1-530 | n-Pr | CH(OH)Et |
| 1-531 | F | CH(OH)Et |
| 1-532 | Cl | CH(OH)Et |
| 1-533 | Br | CH(OH)Et |
| 1-534 | SMe | CH(OH)Et |

TABLE 1-continued

| | | |
|---|---|---|
| 1-535 | CF₃ | CH(OH)Et |
| 1-536 | CN | CH(OH)Et |
| 1-537 | H | CH(OH)CF₃ |
| 1-538 | Me | CH(OH)CF₃ |
| 1-539 | Et | CH(OH)CF₃ |
| 1-540 | n-Pr | CH(OH)CF₃ |
| 1-541 | F | CH(OH)CF₃ |
| 1-542 | Cl | CH(OH)CF₃ |
| 1-543 | Br | CH(OH)CF₃ |
| 1-544 | SMe | CH(OH)CF₃ |
| 1-545 | CF₃ | CH(OH)CF₃ |
| 1-546 | CN | CH(OH)CF₃ |
| 1-547 | H | CH₂OMe |
| 1-548 | Me | CH₂OMe |
| 1-549 | Et | CH₂OMe |
| 1-550 | n-Pr | CH₂OMe |
| 1-551 | F | CH₂OMe |
| 1-552 | Cl | CH₂OMe |
| 1-553 | Br | CH₂OMe |
| 1-554 | SMe | CH₂OMe |
| 1-555 | CF₃ | CH₂OMe |
| 1-556 | CN | CH₂OMe |
| 1-557 | H | CONMe₂ |
| 1-558 | Me | CONMe₂ |
| 1-559 | Et | CONMe₂ |
| 1-560 | n-Pr | CONMe₂ |
| 1-561 | F | CONMe₂ |
| 1-562 | Cl | CONMe₂ |
| 1-563 | Br | CONMe₂ |
| 1-564 | SMe | CONMe₂ |
| 1-565 | CF₃ | CONMe₂ |
| 1-566 | CN | CONMe₂ |
| 1-567 | H | CO(4-CF₃Ph) |
| 1-568 | Me | CO(4-CF₃Ph) |
| 1-569 | Et | CO(4-CF₃Ph) |
| 1-570 | Cl | CO(4-CF₃Ph) |
| 1-571 | Br | CO(4-CF₃Ph) |

TABLE 2

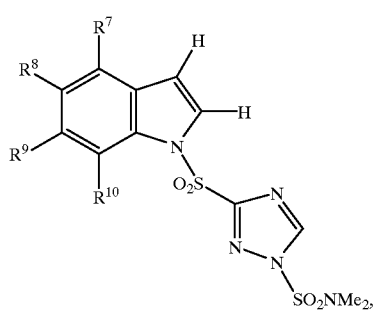
(a)

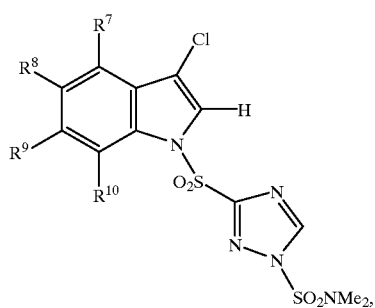
(b)

TABLE 2-continued

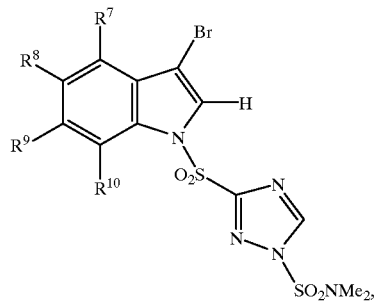
(c)

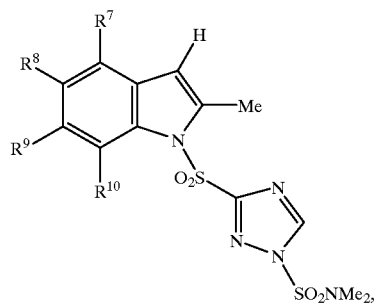
(d)

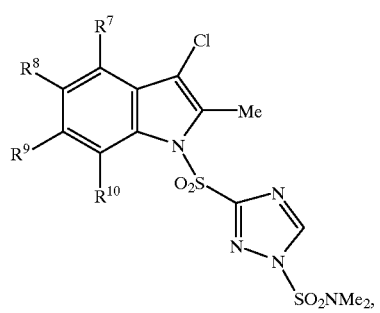
(e)

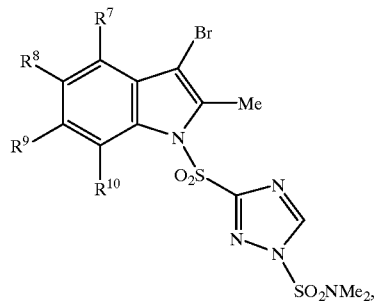
(f)

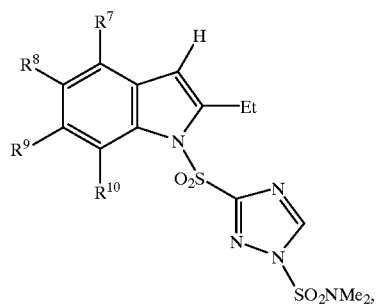
(g)

TABLE 2-continued
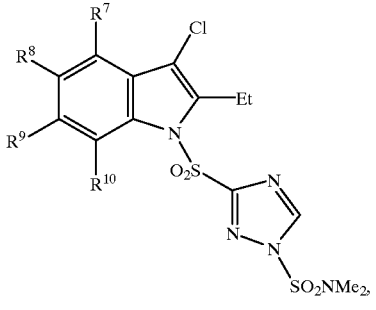 (h)
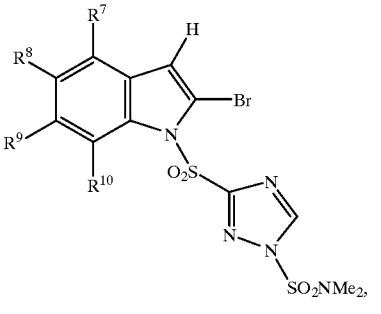 (i)
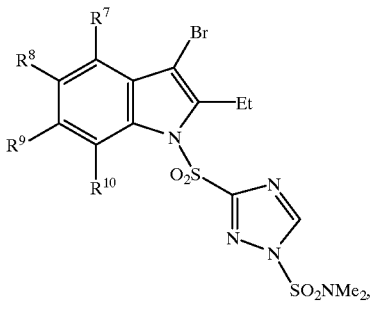 (j)
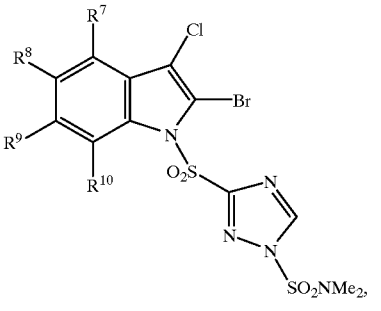 (k)
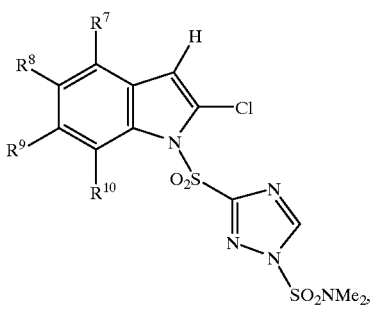 (l)
TABLE 2-continued
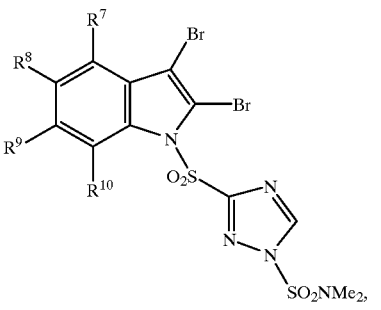 (m)
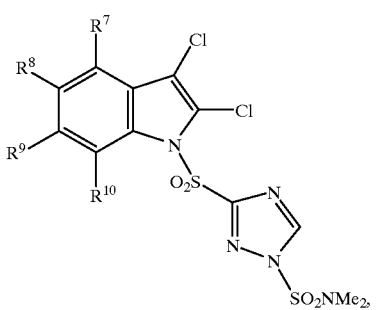 (n)
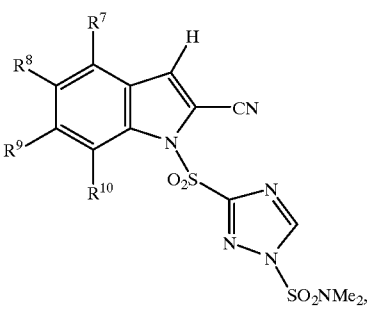 (o)
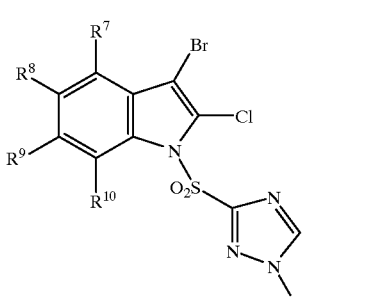 (p)
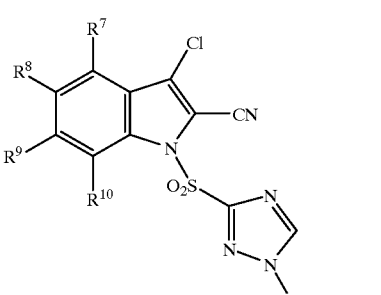 (q)

TABLE 2-continued

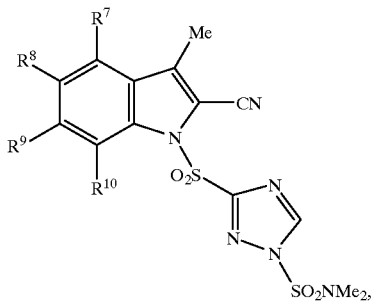
(r)

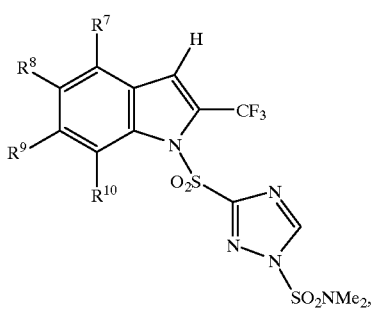
(s)

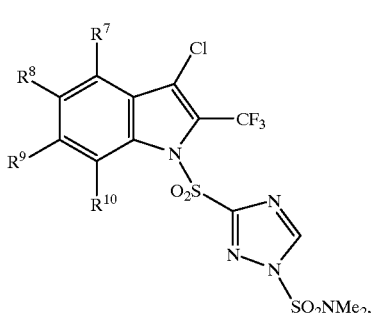
(t)

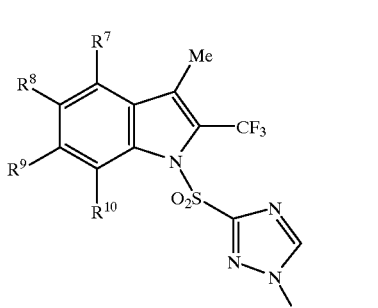
(u)

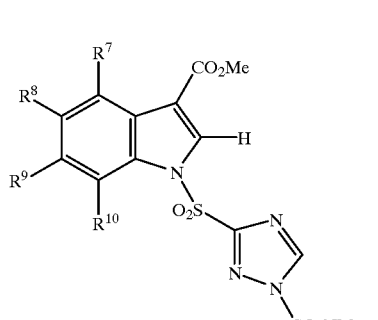
(v)

TABLE 2-continued

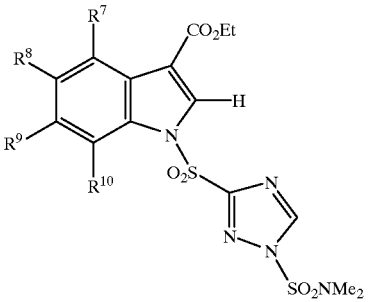
(w)

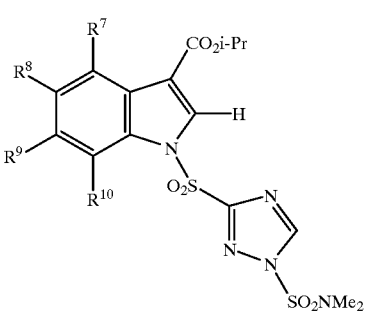
(x)

| Compound No. | $R^7$ | $R^8$ | $R^9$ | $R^{10}$ |
|---|---|---|---|---|
| 2-1 | F | H | H | H |
| 2-2 | H | F | H | H |
| 2-3 | H | H | F | H |
| 2-4 | H | H | H | F |
| 2-5 | Cl | H | H | H |
| 2-6 | H | Cl | H | H |
| 2-7 | H | H | Cl | H |
| 2-8 | H | H | H | Cl |
| 2-9 | Br | H | H | H |
| 2-10 | H | Br | H | H |
| 2-11 | H | H | Br | H |
| 2-12 | H | H | H | Br |
| 2-13 | I | H | H | H |
| 2-14 | H | I | H | H |
| 2-15 | H | H | I | H |
| 2-16 | H | H | H | I |
| 2-17 | Me | H | H | H |
| 2-18 | H | Me | H | H |
| 2-19 | H | H | Me | H |
| 2-20 | H | H | H | Me |
| 2-21 | Et | H | H | H |
| 2-22 | H | Et | H | H |
| 2-23 | H | H | Et | H |
| 2-24 | H | H | H | Et |
| 2-25 | MeO | H | H | H |
| 2-26 | H | MeO | H | H |
| 2-27 | H | H | MeO | H |
| 2-28 | H | H | H | MeO |
| 2-29 | $NO_2$ | H | H | H |
| 2-30 | H | $NO_2$ | H | H |
| 2-31 | H | H | $NO_2$ | H |
| 2-32 | H | H | H | $NO_2$ |
| 2-33 | CN | H | H | H |
| 2-34 | H | CN | H | H |
| 2-35 | H | H | CN | H |
| 2-36 | H | H | H | CN |
| 2-37 | $CF_3$ | H | H | H |
| 2-38 | H | $CF_3$ | H | H |
| 2-39 | H | H | $CF_3$ | H |
| 2-40 | H | H | H | $CF_3$ |
| 2-41 | $CO_2Me$ | H | H | H |
| 2-42 | H | $CO_2Me$ | H | H |
| 2-43 | H | H | $CO_2Me$ | H |
| 2-44 | H | H | H | $CO_2Me$ |

TABLE 3
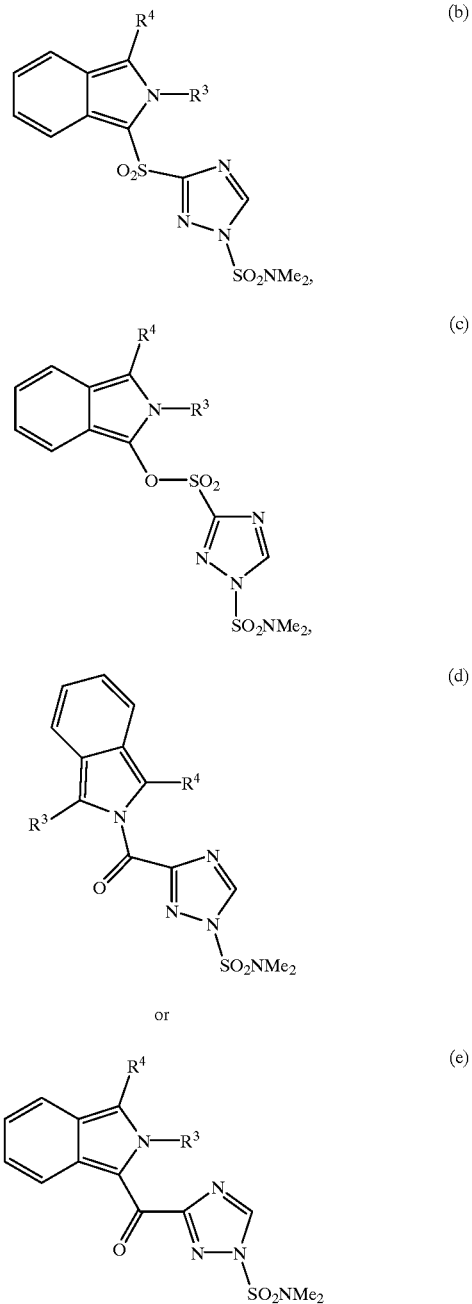
| Compound No. | R⁷ | R⁸ | R⁹ | R¹⁰ |
|---|---|---|---|---|
| 3-1 | H | H | H | H |
| 3-2 | F | H | H | H |
| 3-3 | H | F | H | H |
| 3-4 | H | H | F | H |
| 3-5 | H | H | H | F |
| 3-6 | Cl | H | H | H |
| 3-7 | H | Cl | H | H |
| 3-8 | H | H | Cl | H |
| 3-9 | H | H | H | Cl |
| 3-10 | Br | H | H | H |
| 3-11 | H | Br | H | H |
| 3-12 | H | H | Br | H |
| 3-13 | H | H | H | Br |
| 3-14 | Me | H | H | H |
| 3-15 | H | Me | H | H |
| 3-16 | H | H | Me | H |
| 3-17 | H | H | H | Me |
| 3-18 | CF₃ | H | H | H |
| 3-19 | H | CF₃ | H | H |
| 3-20 | H | H | CF₃ | H |
| 3-21 | H | H | H | CF₃ |
TABLE 4
| Compound No. | R³ | R⁴ |
|---|---|---|
| 4-1 | H | H |
| 4-2 | H | Me |
| 4-3 | H | Et |
| 4-4 | H | Cl |
| 4-5 | H | Br |
| 4-6 | H | CF₃ |
| 4-7 | Me | H |
| 4-8 | Me | Me |
| 4-9 | Me | Et |
| 4-10 | Me | Cl |
| 4-11 | Me | Br |
| 4-12 | Me | CF₃ |
| 4-13 | Et | H |
| 4-14 | Et | Me |

TABLE 4-continued
| | | |
|---|---|---|
| 4-15 | Et | Et |
| 4-16 | Et | Cl |
| 4-17 | Et | Br |
| 4-18 | Et | CF$_3$ |
| 4-19 | Cl | H |
| 4-20 | Cl | Me |
| 4-21 | Cl | Et |
| 4-22 | Cl | Cl |
| 4-23 | Cl | Br |
| 4-24 | Cl | CF$_3$ |
| 4-25 | Br | H |
| 4-26 | Br | Me |
| 4-27 | Br | Et |
| 4-28 | Br | Br |
| 4-29 | Br | CF$_3$ |
TABLE 5
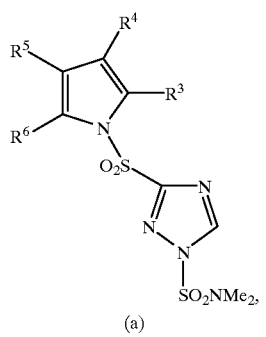
(a)
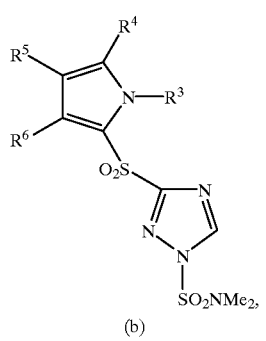
(b)
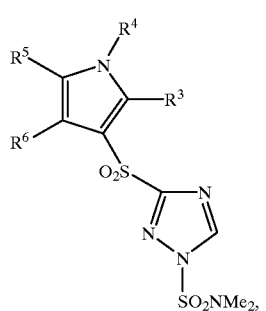
(c)
TABLE 5-continued
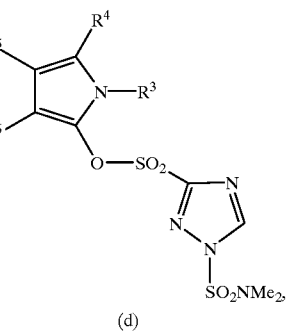
(d)
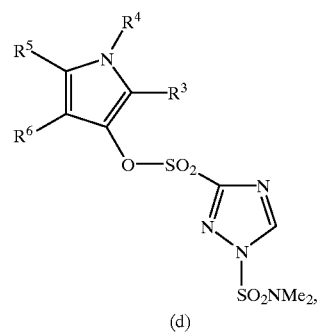
(d)
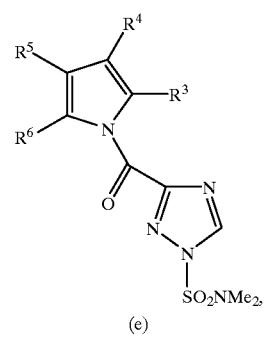
(e)
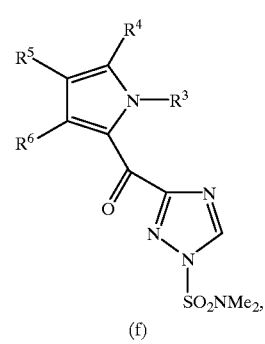
(f)

TABLE 5-continued

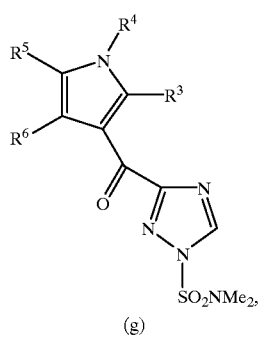

(g)

or

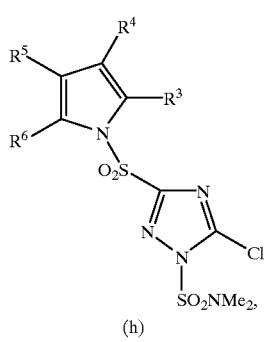

(h)

| Compound No. | R³ | R⁴ | R⁵ | R⁶ |
|---|---|---|---|---|
| 5-1 | H | Ph | H | H |
| 5-2 | Cl | Ph | H | H |
| 5-3 | H | Ph | Cl | H |
| 5-4 | H | Ph | H | Cl |
| 5-5 | Cl | Ph | Cl | H |
| 5-6 | Cl | Ph | H | Cl |
| 5-7 | H | Ph | Cl | Cl |
| 5-8 | Cl | Ph | Cl | Cl |
| 5-9 | Br | Ph | Cl | H |
| 5-10 | Cl | Ph | Br | H |
| 5-11 | Br | Ph | H | Cl |
| 5-12 | Cl | Ph | H | Br |
| 5-13 | H | Ph | Br | Cl |
| 5-14 | H | Ph | Cl | Br |
| 5-15 | Br | Ph | Cl | Cl |
| 5-16 | Cl | Ph | Br | Cl |
| 5-17 | Cl | Ph | Cl | Br |
| 5-18 | Br | Ph | Br | Cl |
| 5-19 | Br | Ph | Cl | Br |
| 5-20 | Cl | Ph | Br | Br |
| 5-21 | Me | Ph | H | H |
| 5-22 | H | Ph | Me | H |
| 5-23 | H | Ph | H | Me |
| 5-24 | Me | Ph | Cl | H |
| 5-25 | Me | Ph | H | Cl |
| 5-26 | Me | Ph | Cl | Cl |
| 5-27 | Me | Ph | Br | Cl |
| 5-28 | Me | Ph | Cl | Br |
| 5-29 | Cl | Ph | Me | H |
| 5-30 | H | Ph | Me | Cl |
| 5-31 | Cl | Ph | Me | Cl |
| 5-32 | Br | Ph | Me | Cl |
| 5-33 | Cl | Ph | Me | Br |
| 5-34 | Cl | Ph | H | Me |
| 5-35 | H | Ph | Cl | Me |
| 5-36 | Cl | Ph | Cl | Me |
| 5-37 | Br | Ph | Cl | Me |
| 5-38 | Cl | Ph | Br | Me |
| 5-39 | Br | Ph | H | H |
| 5-40 | H | Ph | Br | H |
| 5-41 | H | Ph | H | Br |
| 5-42 | Br | Ph | Br | H |
| 5-43 | Br | Ph | H | Br |
| 5-44 | H | Ph | Br | Br |
| 5-45 | Br | Ph | Br | Br |
| 5-46 | Me | Ph | Br | H |
| 5-47 | Me | Ph | H | Br |
| 5-48 | Me | Ph | Br | Br |
| 5-49 | Br | Ph | Me | H |
| 5-50 | H | Ph | Me | Br |
| 5-51 | Br | Ph | Me | Br |
| 5-52 | Br | Ph | H | Me |
| 5-53 | H | Ph | Br | Me |
| 5-54 | Br | Ph | Br | Me |
| 5-55 | Me | Ph | Me | H |
| 5-56 | Me | Ph | Me | Cl |
| 5-57 | Me | Ph | Me | Br |
| 5-58 | H | Ph | Me | Me |
| 5-59 | Cl | Ph | Me | Me |
| 5-60 | Br | Ph | Me | Me |
| 5-61 | Me | Ph | H | Me |
| 5-62 | Me | Ph | Cl | Me |
| 5-63 | Me | Ph | Br | Me |
| 5-64 | CO₂Me | Ph | Me | H |
| 5-65 | Me | Ph | CO₂Me | H |
| 5-66 | CO₂Me | Ph | Me | Cl |
| 5-67 | Me | Ph | CO₂Me | Cl |
| 5-68 | CO₂Me | Ph | Me | Br |
| 5-69 | Me | Ph | CO₂Me | Br |
| 5-70 | Ac | Ph | Me | H |
| 5-71 | Me | Ph | Ac | H |
| 5-72 | Ac | Ph | Me | Cl |
| 5-73 | Me | Ph | Ac | Cl |
| 5-74 | Ac | Ph | Me | Br |
| 5-75 | Me | Ph | Ac | Br |
| 5-76 | CN | Ph | Me | H |
| 5-77 | Me | Ph | CN | H |
| 5-78 | CN | Ph | Me | Cl |
| 5-79 | Me | Ph | CN | Cl |
| 5-80 | CN | Ph | Me | Br |
| 5-81 | Me | Ph | CN | Br |
| 5-82 | H | Ph | CO₂Me | Me |
| 5-83 | H | Ph | Me | CO₂Me |
| 5-84 | Cl | Ph | CO₂Me | Me |
| 5-85 | Cl | Ph | Me | CO₂Me |
| 5-86 | Br | Ph | CO₂Me | Me |
| 5-87 | Br | Ph | Me | CO₂Me |
| 5-88 | H | Ph | Ac | Me |
| 5-89 | H | Ph | Me | Ac |
| 5-90 | Cl | Ph | Ac | Me |
| 5-91 | Cl | Ph | Me | Ac |
| 5-92 | Br | Ph | Ac | Me |
| 5-93 | Br | Ph | Me | Ac |
| 5-94 | H | Ph | CN | Me |
| 5-95 | H | Ph | Me | CN |
| 5-96 | Cl | Ph | CN | Me |
| 5-97 | Cl | Ph | Me | CN |
| 5-98 | Br | Ph | CN | Me |
| 5-99 | Br | Ph | Me | CN |
| 5-100 | CO₂Me | Ph | H | Me |
| 5-101 | Me | Ph | H | CO₂Me |
| 5-102 | CO₂Me | Ph | Cl | Me |
| 5-103 | Me | Ph | Cl | CO₂Me |
| 5-104 | CO₂Me | Ph | Br | Me |
| 5-105 | Me | Ph | Br | CO₂Me |
| 5-106 | Ac | Ph | H | Me |
| 5-107 | Me | Ph | H | Ac |
| 5-108 | Ac | Ph | Cl | Me |
| 5-109 | Me | Ph | Cl | Ac |
| 5-110 | Ac | Ph | Br | Me |
| 5-111 | Me | Ph | Br | Ac |
| 5-112 | CN | Ph | H | Me |
| 5-113 | Me | Ph | H | CN |
| 5-114 | CN | Ph | Cl | Me |
| 5-115 | Me | Ph | Cl | CN |
| 5-116 | CN | Ph | Br | Me |
| 5-117 | Me | Ph | Br | CN |
| 5-118 | Et | Ph | H | H |
| 5-119 | H | Ph | Et | H |
| 5-120 | H | Ph | H | Et |

TABLE 5-continued

| | | | | |
|---|---|---|---|---|
| 5-121 | Et | Ph | Cl | H |
| 5-122 | Et | Ph | H | Cl |
| 5-123 | Et | Ph | Cl | Cl |
| 5-124 | Et | Ph | Br | Cl |
| 5-125 | Et | Ph | Cl | Br |
| 5-126 | Cl | Ph | Et | H |
| 5-127 | H | Ph | Et | Cl |
| 5-128 | Cl | Ph | Et | Cl |
| 5-129 | Br | Ph | Et | Cl |
| 5-130 | Cl | Ph | Et | Br |
| 5-131 | Cl | Ph | H | Et |
| 5-132 | H | Ph | Cl | Et |
| 5-133 | Cl | Ph | Cl | Et |
| 5-134 | Br | Ph | Cl | Et |
| 5-135 | Cl | Ph | Br | Et |
| 5-136 | Et | Ph | Br | H |
| 5-137 | Et | Ph | H | Br |
| 5-138 | Et | Ph | Br | Br |
| 5-139 | Br | Ph | Et | H |
| 5-140 | H | Ph | Et | Br |
| 5-141 | Br | Ph | Et | Br |
| 5-142 | Br | Ph | H | Et |
| 5-143 | H | Ph | Br | Et |
| 5-144 | Br | Ph | Br | Et |
| 5-145 | CN | Ph | H | H |
| 5-146 | H | Ph | CN | H |
| 5-147 | H | Ph | H | CN |
| 5-148 | CN | Ph | Cl | H |
| 5-149 | CN | Ph | H | Cl |
| 5-150 | CN | Ph | Cl | Cl |
| 5-151 | CN | Ph | Br | Cl |
| 5-152 | CN | Ph | Cl | Br |
| 5-153 | Cl | Ph | CN | H |
| 5-154 | H | Ph | CN | Cl |
| 5-155 | Cl | Ph | CN | Cl |
| 5-156 | Br | Ph | CN | Cl |
| 5-157 | Cl | Ph | CN | Br |
| 5-158 | Cl | Ph | H | CN |
| 5-159 | H | Ph | Cl | CN |
| 5-160 | Br | Ph | H | CN |
| 5-161 | H | Ph | Br | CN |
| 5-162 | CN | Ph | Br | H |
| 5-163 | CN | Ph | H | Br |
| 5-164 | CN | Ph | Br | Br |
| 5-165 | Br | Ph | CN | H |
| 5-166 | H | Ph | CN | Br |
| 5-167 | Br | Ph | CN | Br |
| 5-168 | Cl | Ph | Cl | CN |
| 5-169 | Cl | Ph | Br | CN |
| 5-170 | Br | Ph | Cl | CN |
| 5-171 | Br | Ph | Br | CN |
| 5-172 | $CF_3$ | Ph | H | H |
| 5-173 | H | Ph | $CF_3$ | H |
| 5-174 | H | Ph | H | $CF_3$ |
| 5-175 | $CF_3$ | Ph | Cl | H |
| 5-176 | $CF_3$ | Ph | H | Cl |
| 5-177 | $CF_3$ | Ph | Cl | Cl |
| 5-178 | $CF_3$ | Ph | Br | Cl |
| 5-179 | $CF_3$ | Ph | Cl | Br |
| 5-180 | Cl | Ph | $CF_3$ | H |
| 5-181 | H | Ph | $CF_3$ | Cl |
| 5-182 | Cl | Ph | $CF_3$ | Cl |
| 5-183 | Br | Ph | $CF_3$ | Cl |
| 5-184 | Cl | Ph | $CF_3$ | Br |
| 5-185 | Cl | Ph | H | $CF_3$ |
| 5-186 | H | Ph | Cl | $CF_3$ |
| 5-187 | Cl | Ph | Cl | $CF_3$ |
| 5-188 | Br | Ph | Cl | $CF_3$ |
| 5-189 | Cl | Ph | Br | $CF_3$ |
| 5-190 | $CF_3$ | Ph | Br | H |
| 5-191 | $CF_3$ | Ph | H | Br |
| 5-192 | $CF_3$ | Ph | Br | Br |
| 5-193 | Br | Ph | $CF_3$ | H |
| 5-194 | H | Ph | $CF_3$ | Br |
| 5-195 | Br | Ph | $CF_3$ | Br |
| 5-196 | Br | Ph | H | $CF_3$ |
| 5-197 | H | Ph | Br | $CF_3$ |
| 5-198 | Br | Ph | Br | $CF_3$ |
| 5-199 | $NO_2$ | Ph | H | H |
| 5-200 | H | Ph | $NO_2$ | H |
| 5-201 | H | Ph | H | $NO_2$ |
| 5-202 | $NO_2$ | Ph | Cl | H |
| 5-203 | $NO_2$ | Ph | H | Cl |
| 5-204 | $NO_2$ | Ph | Cl | Cl |
| 5-205 | $NO_2$ | Ph | Br | Cl |
| 5-206 | $NO_2$ | Ph | Cl | Br |
| 5-207 | Cl | Ph | $NO_2$ | H |
| 5-208 | H | Ph | $NO_2$ | Cl |
| 5-209 | Cl | Ph | $NO_2$ | Cl |
| 5-210 | Br | Ph | $NO_2$ | Cl |
| 5-211 | Cl | Ph | $NO_2$ | Br |
| 5-212 | Cl | Ph | H | $NO_2$ |
| 5-213 | H | Ph | Cl | $NO_2$ |
| 5-214 | Cl | Ph | Cl | $NO_2$ |
| 5-215 | Br | Ph | Cl | $NO_2$ |
| 5-216 | Cl | Ph | Br | $NO_2$ |
| 5-217 | $NO_2$ | Ph | Br | H |
| 5-218 | $NO_2$ | Ph | H | Br |
| 5-219 | $NO_2$ | Ph | Br | Br |
| 5-220 | Br | Ph | $NO_2$ | H |
| 5-221 | H | Ph | $NO_2$ | Br |
| 5-222 | Br | Ph | $NO_2$ | Br |
| 5-223 | Br | Ph | H | $NO_2$ |
| 5-224 | H | Ph | Br | $NO_2$ |
| 5-225 | Br | Ph | Br | $NO_2$ |
| 5-226 | $CO_2Me$ | Ph | H | H |
| 5-227 | H | Ph | $CO_2Me$ | H |
| 5-228 | H | Ph | H | $CO_2Me$ |
| 5-229 | $CO_2Me$ | Ph | Cl | H |
| 5-230 | $CO_2Me$ | Ph | H | Cl |
| 5-231 | $CO_2Me$ | Ph | Cl | Cl |
| 5-232 | $CO_2Me$ | Ph | Br | Cl |
| 5-233 | $CO_2Me$ | Ph | Cl | Br |
| 5-234 | Cl | Ph | $CO_2Me$ | H |
| 5-235 | H | Ph | $CO_2Me$ | Cl |
| 5-236 | Cl | Ph | $CO_2Me$ | Cl |
| 5-237 | Br | Ph | $CO_2Me$ | Cl |
| 5-238 | Cl | Ph | $CO_2Me$ | Br |
| 5-239 | Cl | Ph | H | $CO_2Me$ |
| 5-240 | H | Ph | Cl | $CO_2Me$ |
| 5-241 | Cl | Ph | Cl | $CO_2Me$ |
| 5-242 | Br | Ph | Cl | $CO_2Me$ |
| 5-243 | Cl | Ph | Br | $CO_2Me$ |
| 5-244 | $CO_2Me$ | Ph | Br | H |
| 5-245 | $CO_2Me$ | Ph | H | Br |
| 5-246 | $CO_2Me$ | Ph | Br | Br |
| 5-247 | Br | Ph | $CO_2Me$ | H |
| 5-248 | H | Ph | $CO_2Me$ | Br |
| 5-249 | Br | Ph | $CO_2Me$ | Br |
| 5-250 | Br | Ph | H | $CO_2Me$ |
| 5-251 | H | Ph | Br | $CO_2Me$ |
| 5-252 | Br | Ph | Br | $CO_2Me$ |
| 5-253 | Ac | Ph | H | H |
| 5-254 | H | Ph | Ac | H |
| 5-255 | H | Ph | H | Ac |
| 5-256 | Ac | Ph | Cl | H |
| 5-257 | Ac | Ph | H | Cl |
| 5-258 | Ac | Ph | Cl | Cl |
| 5-259 | Ac | Ph | Br | Cl |
| 5-260 | Ac | Ph | Cl | Br |
| 5-261 | Cl | Ph | Ac | H |
| 5-262 | H | Ph | Ac | Cl |
| 5-263 | Cl | Ph | Ac | Cl |
| 5-264 | Br | Ph | Ac | Cl |
| 5-265 | Cl | Ph | Ac | Br |
| 5-266 | Cl | Ph | H | Ac |
| 5-267 | H | Ph | Cl | Ac |
| 5-268 | Cl | Ph | Cl | Ac |
| 5-269 | Br | Ph | Cl | Ac |
| 5-270 | Cl | Ph | Br | Ac |
| 5-271 | Ac | Ph | Br | H |
| 5-272 | Ac | Ph | H | Br |
| 5-273 | Ac | Ph | Br | Br |
| 5-274 | Br | Ph | Ac | H |
| 5-275 | H | Ph | Ac | Br |
| 5-276 | Br | Ph | Ac | Br |
| 5-277 | Br | Ph | H | Ac |
| 5-278 | H | Ph | Br | Ac |

TABLE 5-continued

| | | | | |
|---|---|---|---|---|
| 5-279 | Br | Ph | Br | Ac |
| 5-280 | Ph | H | H | H |
| 5-281 | Ph | Cl | H | H |
| 5-282 | Ph | H | Cl | H |
| 5-283 | Ph | H | H | Cl |
| 5-284 | Ph | Cl | Cl | H |
| 5-285 | Ph | Br | Cl | H |
| 5-286 | Ph | Cl | Br | H |
| 5-287 | Ph | Cl | H | Cl |
| 5-288 | Ph | Br | H | Cl |
| 5-289 | Ph | Cl | H | Br |
| 5-290 | Ph | H | Cl | Cl |
| 5-291 | Ph | H | Br | Cl |
| 5-292 | Ph | H | Cl | Br |
| 5-293 | Ph | Cl | Cl | Cl |
| 5-294 | Ph | Br | Cl | Cl |
| 5-295 | Ph | Cl | Br | Cl |
| 5-296 | Ph | Cl | Cl | Br |
| 5-297 | Ph | Br | Br | Cl |
| 5-298 | Ph | Br | Cl | Br |
| 5-299 | Ph | Cl | Br | Br |
| 5-300 | Ph | Me | H | H |
| 5-301 | Ph | H | Me | H |
| 5-302 | Ph | H | H | Me |
| 5-303 | Ph | Me | Cl | H |
| 5-304 | Ph | Me | H | Cl |
| 5-305 | Ph | Me | Cl | Cl |
| 5-306 | Ph | Me | Br | Cl |
| 5-307 | Ph | Me | Cl | Br |
| 5-308 | Ph | Cl | Me | H |
| 5-309 | Ph | H | Me | Cl |
| 5-310 | Ph | Cl | Me | Cl |
| 5-311 | Ph | Cl | Me | Br |
| 5-312 | Ph | Cl | H | Me |
| 5-313 | Ph | H | Cl | Me |
| 5-314 | Ph | Cl | Cl | Me |
| 5-315 | Ph | Br | H | H |
| 5-316 | Ph | H | Br | H |
| 5-317 | Ph | H | H | Br |
| 5-318 | Ph | Br | Br | H |
| 5-319 | Ph | Br | H | Br |
| 5-320 | Ph | H | Br | Br |
| 5-321 | Ph | Br | Br | Br |
| 5-322 | Ph | Me | Br | H |
| 5-323 | Ph | Me | H | Br |
| 5-324 | Ph | Me | Br | Br |
| 5-325 | Ph | Br | Me | H |
| 5-326 | Ph | H | Me | Br |
| 5-327 | Ph | Br | Me | Br |
| 5-328 | Ph | Br | Me | Cl |
| 5-329 | Ph | Br | H | Me |
| 5-330 | Ph | H | Br | Me |
| 5-331 | Ph | Br | Br | Me |
| 5-332 | Ph | CN | H | H |
| 5-333 | Ph | H | CN | H |
| 5-334 | Ph | H | H | CN |
| 5-335 | Ph | CN | Cl | H |
| 5-336 | Ph | CN | H | Cl |
| 5-337 | Ph | CN | Cl | Cl |
| 5-338 | Ph | CN | Br | Cl |
| 5-339 | Ph | CN | Cl | Br |
| 5-340 | Ph | Cl | CN | H |
| 5-341 | Ph | H | CN | Cl |
| 5-342 | Ph | Cl | CN | Cl |
| 5-343 | Ph | Br | CN | Cl |
| 5-344 | Ph | Cl | CN | Br |
| 5-345 | Ph | Cl | H | CN |
| 5-346 | Ph | H | Cl | CN |
| 5-347 | Ph | Cl | Cl | CN |
| 5-348 | Ph | Br | Cl | CN |
| 5-349 | Ph | Cl | Br | CN |
| 5-350 | Ph | CN | Br | H |
| 5-351 | Ph | CN | H | Br |
| 5-352 | Ph | CN | Br | Br |
| 5-353 | Ph | Br | CN | H |
| 5-354 | Ph | H | CN | Br |
| 5-355 | Ph | Br | CN | Br |
| 5-356 | Ph | Br | H | CN |
| 5-357 | Ph | H | Br | CN |
| 5-358 | Ph | Br | Br | CN |
| 5-359 | Ph | $CF_3$ | H | H |
| 5-360 | Ph | H | $CF_3$ | H |
| 5-361 | Ph | H | H | $CF_3$ |
| 5-362 | Ph | $CF_3$ | Cl | H |
| 5-363 | Ph | $CF_3$ | H | Cl |
| 5-364 | Ph | $CF_3$ | Cl | Cl |
| 5-365 | Ph | $CF_3$ | Br | Cl |
| 5-366 | Ph | $CF_3$ | Cl | Br |
| 5-367 | Ph | Cl | $CF_3$ | H |
| 5-368 | Ph | H | $CF_3$ | Cl |
| 5-369 | Ph | Cl | $CF_3$ | Cl |
| 5-370 | Ph | Br | $CF_3$ | Cl |
| 5-371 | Ph | Cl | $CF_3$ | Br |
| 5-372 | Ph | Cl | H | $CF_3$ |
| 5-373 | Ph | H | Cl | $CF_3$ |
| 5-374 | Ph | Cl | Cl | $CF_3$ |
| 5-375 | Ph | Br | Cl | $CF_3$ |
| 5-376 | Ph | Cl | Br | $CF_3$ |
| 5-377 | Ph | $CF_3$ | Br | H |
| 5-378 | Ph | $CF_3$ | H | Br |
| 5-379 | Ph | $CF_3$ | Br | Br |
| 5-380 | Ph | Br | $CF_3$ | H |
| 5-381 | Ph | H | $CF_3$ | Br |
| 5-382 | Ph | Br | $CF_3$ | Br |
| 5-383 | Ph | Br | H | $CF_3$ |
| 5-384 | Ph | H | Br | $CF_3$ |
| 5-385 | Ph | Br | Br | $CF_3$ |
| 5-386 | Ph | $NO_2$ | H | H |
| 5-387 | Ph | H | $NO_2$ | H |
| 5-388 | Ph | H | H | $NO_2$ |
| 5-389 | Ph | $NO_2$ | Cl | H |
| 5-390 | Ph | $NO_2$ | H | Cl |
| 5-391 | Ph | $NO_2$ | Cl | Cl |
| 5-392 | Ph | $NO_2$ | Br | Cl |
| 5-393 | Ph | $NO_2$ | Cl | Br |
| 5-394 | Ph | Cl | $NO_2$ | H |
| 5-395 | Ph | H | $NO_2$ | Cl |
| 5-396 | Ph | Cl | $NO_2$ | Cl |
| 5-397 | Ph | Br | $NO_2$ | Cl |
| 5-398 | Ph | Cl | $NO_2$ | Br |
| 5-399 | Ph | $NO_2$ | Br | H |
| 5-400 | Ph | $NO_2$ | H | Br |
| 5-401 | Ph | $NO_2$ | Br | Br |
| 5-402 | Ph | Br | $NO_2$ | H |
| 5-403 | Ph | H | $NO_2$ | Br |
| 5-404 | Ph | Br | $NO_2$ | Br |
| 5-405 | Ph | $CO_2Me$ | H | H |
| 5-406 | Ph | H | $CO_2Me$ | H |
| 5-407 | Ph | H | H | $CO_2Me$ |
| 5-408 | Ph | $CO_2Me$ | Cl | H |
| 5-409 | Ph | $CO_2Me$ | H | Cl |
| 5-410 | Ph | $CO_2Me$ | Cl | Cl |
| 5-411 | Ph | $CO_2Me$ | Br | Cl |
| 5-412 | Ph | $CO_2Me$ | Cl | Br |
| 5-413 | Ph | Cl | $CO_2Me$ | H |
| 5-414 | Ph | H | $CO_2Me$ | Cl |
| 5-415 | Ph | Cl | $CO_2Me$ | Cl |
| 5-416 | Ph | Br | $CO_2Me$ | Cl |
| 5-417 | Ph | Cl | $CO_2Me$ | Br |
| 5-418 | Ph | Cl | H | $CO_2Me$ |
| 5-419 | Ph | H | Cl | $CO_2Me$ |
| 5-420 | Ph | Cl | Cl | $CO_2Me$ |
| 5-421 | Ph | Br | Cl | $CO_2Me$ |
| 5-422 | Ph | Cl | Br | $CO_2Me$ |
| 5-423 | Ph | Cl | Br | Me |
| 5-424 | Ph | Br | Cl | Me |
| 5-425 | Ph | $CO_2Me$ | Br | H |
| 5-426 | Ph | $CO_2Me$ | H | Br |
| 5-427 | Ph | $CO_2Me$ | Br | Br |
| 5-428 | Ph | Br | $CO_2Me$ | H |
| 5-429 | Ph | H | $CO_2Me$ | Br |
| 5-430 | Ph | Br | $CO_2Me$ | Br |
| 5-431 | Ph | Br | H | $CO_2Me$ |
| 5-432 | Ph | H | Br | $CO_2Me$ |
| 5-433 | Ph | Br | Br | $CO_2Me$ |
| 5-434 | Ph | $CO_2Et$ | Cl | H |
| 5-435 | Ph | $CO_2Et$ | H | Cl |
| 5-436 | Ph | $CO_2Et$ | Cl | Cl |

TABLE 5-continued

| | | | | |
|---|---|---|---|---|
| 5-437 | Ph | CO₂Et | Br | Cl |
| 5-438 | Ph | CO₂Et | Cl | Br |
| 5-439 | Ph | CO₂Et | Br | Br |
| 5-440 | Ph | Cl | CO₂Et | H |
| 5-441 | Ph | H | CO₂Et | Cl |
| 5-442 | Ph | Cl | CO₂Et | Cl |
| 5-443 | Ph | Br | CO₂Et | Cl |
| 5-444 | Ph | Cl | CO₂Et | Br |
| 5-445 | Ph | Br | CO₂Et | Br |
| 5-446 | Ph | H | H | CO₂Et |
| 5-447 | Ph | Cl | H | CO₂Et |
| 5-448 | Ph | H | Cl | CO₂Et |
| 5-449 | Ph | Cl | Cl | CO₂Et |
| 5-450 | Ph | Cl | Br | CO₂Et |
| 5-451 | Ph | Br | Cl | CO₂Et |
| 5-452 | Ph | Br | Br | CO₂Et |
| 5-453 | Ph | H | H | Ac |
| 5-454 | Ph | Cl | H | Ac |
| 5-455 | Ph | H | Cl | Ac |
| 5-456 | Ph | Cl | Cl | Ac |
| 5-457 | Ph | H | H | Et |
| 5-458 | Ph | Cl | H | Et |
| 5-459 | Ph | H | Cl | Et |
| 5-460 | Ph | Cl | Cl | Et |
| 5-461 | Ph | H | H | Ph |
| 5-462 | Ph | Cl | H | Ph |
| 5-463 | Ph | H | Cl | Ph |
| 5-464 | Ph | Cl | Cl | Ph |
| 5-465 | Ph | Ph | H | H |
| 5-466 | H | Ph | Ph | H |
| 5-467 | H | Ph | H | Ph |
| 5-468 | Ph | Ph | Cl | H |
| 5-469 | Ph | Ph | H | Cl |
| 5-470 | Ph | Ph | Cl | Cl |
| 5-471 | Ph | Ph | Br | Cl |
| 5-472 | Ph | Ph | Cl | Br |
| 5-473 | Ph | Ph | Br | H |
| 5-474 | Ph | Ph | H | Br |
| 5-475 | Ph | Ph | Br | Br |
| 5-476 | Cl | Ph | Ph | H |
| 5-477 | Cl | Ph | Ph | Cl |
| 5-478 | Br | Ph | Ph | H |
| 5-479 | Br | Ph | Ph | Cl |
| 5-480 | Br | Ph | Ph | Br |
| 5-481 | Cl | Ph | H | Ph |
| 5-482 | H | Ph | Cl | Ph |
| 5-483 | Br | Ph | H | Ph |
| 5-484 | H | Ph | Br | Ph |
| 5-485 | Cl | Ph | Cl | Ph |
| 5-486 | Br | Ph | Cl | Ph |
| 5-487 | Cl | Ph | Br | Ph |
| 5-488 | Br | Ph | Br | Ph |
| 5-489 | CO₂Et | Ph | H | H |
| 5-490 | H | Ph | CO₂Et | H |
| 5-491 | H | Ph | H | CO₂Et |
| 5-492 | CO₂Et | Ph | Cl | H |
| 5-493 | CO₂Et | Ph | H | Cl |
| 5-494 | CO₂Et | Ph | Cl | Cl |
| 5-495 | Cl | Ph | CO₂Et | H |
| 5-496 | H | Ph | CO₂Et | Cl |
| 5-497 | Cl | Ph | CO₂Et | Cl |
| 5-498 | Cl | Ph | H | CO₂Et |
| 5-499 | H | Ph | Cl | CO₂Et |
| 5-500 | Cl | Ph | Cl | CO₂Et |
| 5-501 | CO₂Et | Ph | Br | H |
| 5-502 | CO₂Et | Ph | H | Br |
| 5-503 | CO₂Et | Ph | Cl | Br |
| 5-504 | CO₂Et | Ph | Br | Cl |
| 5-505 | CO₂Et | Ph | Br | Br |
| 5-506 | Br | Ph | CO₂Et | H |
| 5-507 | H | Ph | CO₂Et | Br |
| 5-508 | Br | Ph | CO₂Et | Br |
| 5-509 | Cl | Ph | CO₂Et | Br |
| 5-510 | Br | Ph | CO₂Et | Cl |
| 5-511 | Br | Ph | H | CO₂Et |
| 5-512 | H | Ph | Br | CO₂Et |
| 5-513 | Br | Ph | Br | CO₂Et |
| 5-514 | Cl | Ph | Br | CO₂Et |
| 5-515 | Br | Ph | Cl | CO₂Et |

TABLE 5-continued

| | | | | |
|---|---|---|---|---|
| 5-516 | H | Ph | CO₂Et | Me |
| 5-517 | Cl | Ph | CO₂Et | Me |
| 5-518 | Br | Ph | CO₂Et | Me |
| 5-519 | Me | Ph | CO₂Et | H |
| 5-520 | Me | Ph | CO₂Et | Cl |
| 5-521 | Me | Ph | CO₂Et | Br |
| 5-522 | Ph | H | H | NO₂ |
| 5-523 | Ph | Cl | H | NO₂ |
| 5-524 | Ph | H | Cl | NO₂ |
| 5-525 | Ph | Cl | Cl | NO₂ |

TABLE 6

(a)

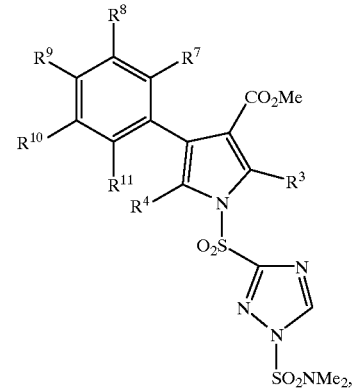

(b)

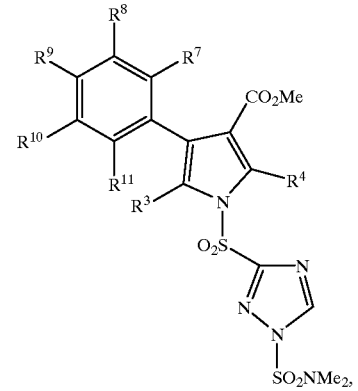

(c)

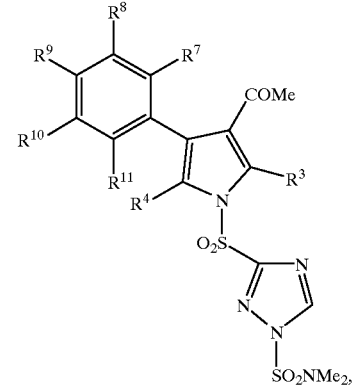

TABLE 6-continued
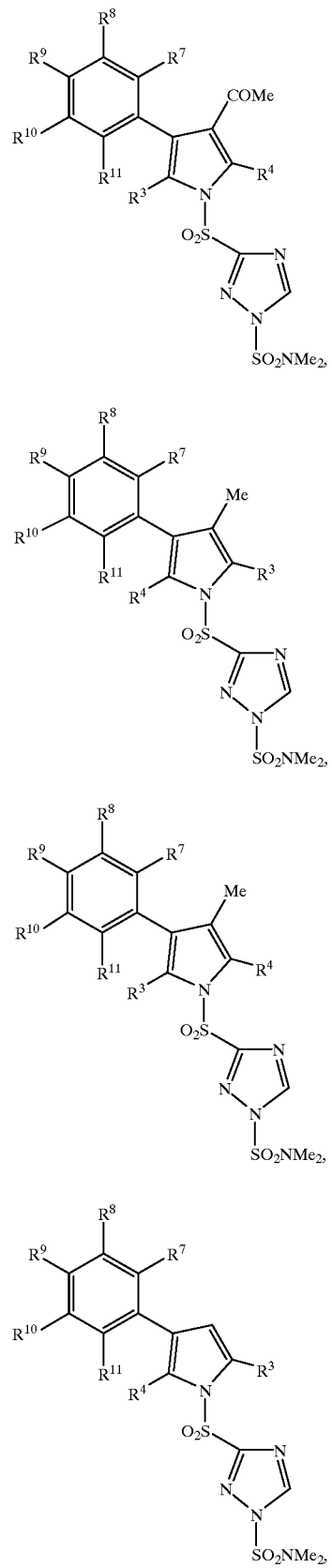
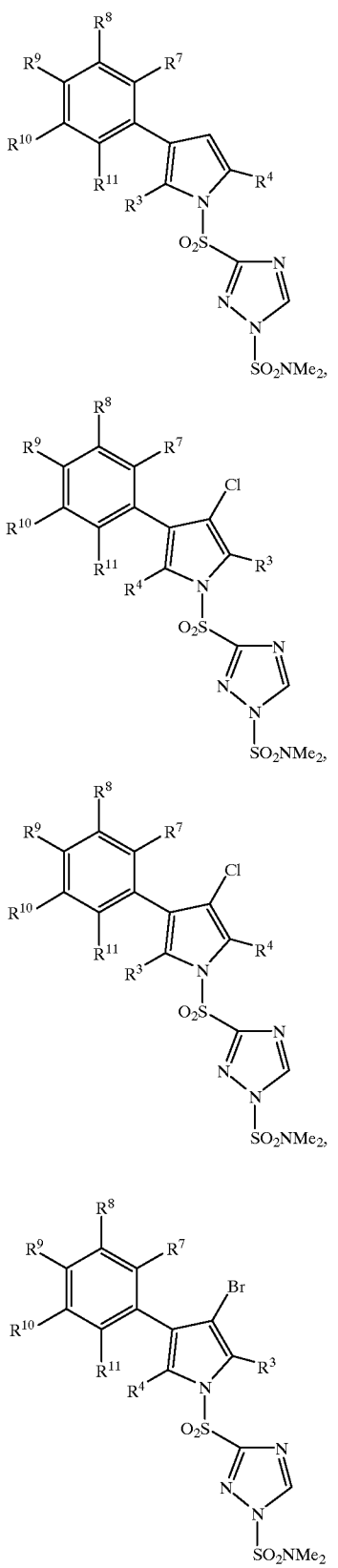

TABLE 6-continued (l)

[Structure: pyrrole with R³ at 2-position, R⁴ at 5-position, Br at 4-position, N-SO₂-triazole-SO₂NMe₂ at 1-position, and phenyl with R⁷, R⁸, R⁹, R¹⁰, R¹¹ substituents at 3-position]

| Compound No. | R³ | R⁴ | R⁷ | R⁸ | R⁹ | R¹⁰ | R¹¹ |
|---|---|---|---|---|---|---|---|
| 6-1 | H | H | Me | H | H | H | H |
| 6-2 | H | H | H | Me | H | H | H |
| 6-3 | H | H | H | H | Me | H | H |
| 6-4 | H | H | Cl | H | H | H | H |
| 6-5 | H | H | H | Cl | H | H | H |
| 6-6 | H | H | H | H | Cl | H | H |
| 6-7 | H | H | Br | H | H | H | H |
| 6-8 | H | H | H | Br | H | H | H |
| 6-9 | H | H | H | H | Br | H | H |
| 6-10 | H | H | CF₃ | H | H | H | H |
| 6-11 | H | H | H | CF₃ | H | H | H |
| 6-12 | H | H | H | H | CF₃ | H | H |
| 6-13 | H | Cl | Me | H | H | H | H |
| 6-14 | H | Cl | H | Me | H | H | H |
| 6-15 | H | Cl | H | H | Me | H | H |
| 6-16 | H | Cl | Cl | H | H | H | H |
| 6-17 | H | Cl | H | Cl | H | H | H |
| 6-18 | H | Cl | H | H | Cl | H | H |
| 6-19 | H | Cl | Br | H | H | H | H |
| 6-20 | H | Cl | H | Br | H | H | H |
| 6-21 | H | Cl | H | H | Br | H | H |
| 6-22 | H | Cl | CF₃ | H | H | H | H |
| 6-23 | H | Cl | H | CF₃ | H | H | H |
| 6-24 | H | Cl | H | H | CF₃ | H | H |
| 6-25 | H | Br | Me | H | H | H | H |
| 6-26 | H | Br | H | Me | H | H | H |
| 6-27 | H | Br | H | H | Me | H | H |
| 6-28 | H | Br | Cl | H | H | H | H |
| 6-29 | H | Br | H | Cl | H | H | H |
| 6-30 | H | Br | H | H | Cl | H | H |
| 6-31 | H | Br | Br | H | H | H | H |
| 6-32 | H | Br | H | Br | H | H | H |
| 6-33 | H | Br | H | H | Br | H | H |
| 6-34 | H | Br | CF₃ | H | H | H | H |
| 6-35 | H | Br | H | CF₃ | H | H | H |
| 6-36 | H | Br | H | H | CF₃ | H | H |
| 6-37 | H | Me | Me | H | H | H | H |
| 6-38 | H | Me | H | Me | H | H | H |
| 6-39 | H | Me | H | H | Me | H | H |
| 6-40 | H | Me | Cl | H | H | H | H |
| 6-41 | H | Me | H | Cl | H | H | H |
| 6-42 | H | Me | H | H | Cl | H | H |
| 6-43 | H | Me | Br | H | H | H | H |
| 6-44 | H | Me | H | Br | H | H | H |
| 6-45 | H | Me | H | H | Br | H | H |
| 6-46 | H | Me | CF₃ | H | H | H | H |
| 6-47 | H | Me | H | CF₃ | H | H | H |
| 6-48 | H | Me | H | H | CF₃ | H | H |
| 6-49 | Me | Cl | Me | H | H | H | H |
| 6-50 | Me | Cl | H | Me | H | H | H |
| 6-51 | Me | Cl | H | H | Me | H | H |
| 6-52 | Me | Cl | Cl | H | H | H | H |
| 6-53 | Me | Cl | H | Cl | H | H | H |
| 6-54 | Me | Cl | H | H | Cl | H | H |
| 6-55 | Me | Cl | Br | H | H | H | H |
| 6-56 | Me | Cl | H | Br | H | H | H |
| 6-57 | Me | Cl | H | H | Br | H | H |
| 6-58 | Me | Cl | CF₃ | H | H | H | H |
| 6-59 | Me | Cl | H | CF₃ | H | H | H |
| 6-60 | Me | Cl | H | H | CF₃ | H | H |
| 6-61 | Me | Br | Me | H | H | H | H |
| 6-62 | Me | Br | H | Me | H | H | H |
| 6-63 | Me | Br | H | H | Me | H | H |
| 6-64 | Me | Br | Cl | H | H | H | H |
| 6-65 | Me | Br | H | Cl | H | H | H |
| 6-66 | Me | Br | H | H | Cl | H | H |
| 6-67 | Me | Br | Br | H | H | H | H |
| 6-68 | Me | Br | H | Br | H | H | H |
| 6-69 | Me | Br | H | H | Br | H | H |
| 6-70 | Me | Br | CF₃ | H | H | H | H |
| 6-71 | Me | Br | H | CF₃ | H | H | H |
| 6-72 | Me | Br | H | H | CF₃ | H | H |
| 6-73 | Cl | Cl | Me | H | H | H | H |
| 6-74 | Cl | Cl | H | Me | H | H | H |
| 6-75 | Cl | Cl | H | H | Me | H | H |
| 6-76 | Cl | Cl | Cl | H | H | H | H |
| 6-77 | Cl | Cl | H | Cl | H | H | H |
| 6-78 | Cl | Cl | H | H | Cl | H | H |
| 6-79 | Cl | Cl | Br | H | H | H | H |
| 6-80 | Cl | Cl | H | Br | H | H | H |
| 6-81 | Cl | Cl | H | H | Br | H | H |
| 6-82 | Cl | Cl | CF₃ | H | H | H | H |
| 6-83 | Cl | Cl | H | CF₃ | H | H | H |
| 6-84 | Cl | Cl | H | H | CF₃ | H | H |
| 6-85 | Cl | Br | Me | H | H | H | H |
| 6-86 | Cl | Br | H | Me | H | H | H |
| 6-87 | Cl | Br | H | H | Me | H | H |
| 6-88 | Cl | Br | Cl | H | H | H | H |
| 6-89 | Cl | Br | H | Cl | H | H | H |
| 6-90 | Cl | Br | H | H | Cl | H | H |
| 6-91 | Cl | Br | Br | H | H | H | H |
| 6-92 | Cl | Br | H | Br | H | H | H |
| 6-93 | Cl | Br | H | H | Br | H | H |
| 6-94 | Cl | Br | CF₃ | H | H | H | H |
| 6-95 | Cl | Br | H | CF₃ | H | H | H |
| 6-96 | Cl | Br | H | H | CF₃ | H | H |
| 6-97 | Br | Br | Me | H | H | H | H |
| 6-98 | Br | Br | H | Me | H | H | H |
| 6-99 | Br | Br | H | H | Me | H | H |
| 6-100 | Br | Br | Cl | H | H | H | H |
| 6-101 | Br | Br | H | Cl | H | H | H |
| 6-102 | Br | Br | H | H | Cl | H | H |
| 6-103 | Br | Br | Br | H | H | H | H |
| 6-104 | Br | Br | H | Br | H | H | H |
| 6-105 | Br | Br | H | H | Br | H | H |
| 6-106 | Br | Br | CF₃ | H | H | H | H |
| 6-107 | Br | Br | H | CF₃ | H | H | H |
| 6-108 | Br | Br | H | H | CF₃ | H | H |
| 6-109 | Me | Me | Me | H | H | H | H |
| 6-110 | Me | Me | H | Me | H | H | H |
| 6-111 | Me | Me | H | H | Me | H | H |
| 6-112 | Me | Me | Cl | H | H | H | H |
| 6-113 | Me | Me | H | Cl | H | H | H |
| 6-114 | Me | Me | H | H | Cl | H | H |
| 6-115 | Me | Me | Br | H | H | H | H |
| 6-116 | Me | Me | H | Br | H | H | H |
| 6-117 | Me | Me | H | H | Br | H | H |
| 6-118 | Me | Me | CF₃ | H | H | H | H |
| 6-119 | Me | Me | H | CF₃ | H | H | H |
| 6-120 | Me | Me | H | H | CF₃ | H | H |
| 6-121 | H | H | Me | Cl | H | H | H |
| 6-122 | H | H | Me | H | Cl | H | H |
| 6-123 | H | H | Me | H | H | Cl | H |
| 6-124 | H | H | Me | H | H | H | Cl |
| 6-125 | H | H | Cl | Me | H | H | H |
| 6-126 | H | H | H | Me | Cl | H | H |
| 6-127 | H | H | H | Me | H | Cl | H |
| 6-128 | H | H | H | Me | H | H | Cl |
| 6-129 | H | H | Cl | H | Me | H | H |
| 6-130 | H | H | H | Cl | Me | H | H |
| 6-131 | H | H | Cl | Cl | H | H | H |
| 6-132 | H | H | Cl | H | Cl | H | H |
| 6-133 | H | H | Cl | H | H | Cl | H |
| 6-134 | H | H | Cl | H | H | H | Cl |
| 6-135 | H | H | H | Cl | Cl | H | H |
| 6-136 | H | H | H | Cl | H | Cl | H |

TABLE 6-continued

| | | | | | | | |
|---|---|---|---|---|---|---|---|
| 6-137 | H | H | CF$_3$ | Cl | H | H | H |
| 6-138 | H | H | CF$_3$ | H | Cl | H | H |
| 6-139 | H | H | CF$_3$ | H | H | Cl | H |
| 6-140 | H | H | CF$_3$ | H | H | H | Cl |
| 6-141 | H | H | Cl | CF$_3$ | H | H | H |
| 6-142 | H | H | H | CF$_3$ | Cl | H | H |
| 6-143 | H | H | H | CF$_3$ | H | Cl | H |
| 6-144 | H | H | H | CF$_3$ | H | H | Cl |
| 6-145 | H | H | Cl | H | CF$_3$ | H | H |
| 6-146 | H | H | H | Cl | CF$_3$ | H | H |
| 6-147 | H | Cl | Me | Cl | H | H | H |
| 6-148 | H | Cl | Me | H | Cl | H | H |
| 6-149 | H | Cl | Me | H | H | Cl | H |
| 6-150 | H | Cl | Me | H | H | H | Cl |
| 6-151 | H | Cl | Cl | Me | H | H | H |
| 6-152 | H | Cl | H | Me | Cl | H | H |
| 6-153 | H | Cl | H | Me | H | Cl | H |
| 6-154 | H | Cl | H | Me | H | H | Cl |
| 6-155 | H | Cl | Cl | H | Me | H | H |
| 6-156 | H | Cl | H | Cl | Me | H | H |
| 6-157 | H | Cl | Cl | Cl | H | H | H |
| 6-158 | H | Cl | Cl | H | Cl | H | H |
| 6-159 | H | Cl | Cl | H | H | Cl | H |
| 6-160 | H | Cl | Cl | H | H | H | Cl |
| 6-161 | H | Cl | H | Cl | Cl | H | H |
| 6-162 | H | Cl | H | Cl | H | Cl | H |
| 6-163 | H | Br | Me | Cl | H | H | H |
| 6-164 | H | Br | Me | H | Cl | H | H |
| 6-165 | H | Br | Me | H | H | Cl | H |
| 6-166 | H | Br | Me | H | H | H | Cl |
| 6-167 | H | Br | Cl | Me | H | H | H |
| 6-168 | H | Br | H | Me | Cl | H | H |
| 6-169 | H | Br | H | Me | H | Cl | H |
| 6-170 | H | Br | H | Me | H | H | Cl |
| 6-171 | H | Br | Cl | H | Me | H | H |
| 6-172 | H | Br | H | Cl | Me | H | H |
| 6-173 | H | Br | Cl | Cl | H | H | H |
| 6-174 | H | Br | Cl | H | Cl | H | H |
| 6-175 | H | Br | Cl | H | H | Cl | H |
| 6-176 | H | Br | Cl | H | H | H | Cl |
| 6-177 | H | Br | H | Cl | Cl | H | H |
| 6-178 | H | Br | H | Cl | H | Cl | H |
| 6-179 | H | Me | Me | Cl | H | H | H |
| 6-180 | H | Me | Me | H | Cl | H | H |
| 6-181 | H | Me | Me | H | H | Cl | H |
| 6-182 | H | Me | Me | H | H | H | Cl |
| 6-183 | H | Me | Cl | Me | H | H | H |
| 6-184 | H | Me | H | Me | Cl | H | H |
| 6-185 | H | Me | H | Me | H | Cl | H |
| 6-186 | H | Me | H | Me | H | H | Cl |
| 6-187 | H | Me | Cl | H | Me | H | H |
| 6-188 | H | Me | H | Cl | Me | H | H |
| 6-189 | H | Me | Cl | Cl | H | H | H |
| 6-190 | H | Me | Cl | H | Cl | H | H |
| 6-191 | H | Me | Cl | H | H | Cl | H |
| 6-192 | H | Me | Cl | H | H | H | Cl |
| 6-193 | H | Me | H | Cl | Cl | H | H |
| 6-194 | H | Me | H | Cl | H | Cl | H |
| 6-195 | Cl | Me | Me | Cl | H | H | H |
| 6-196 | Cl | Me | Me | H | Cl | H | H |
| 6-197 | Cl | Me | Me | H | H | Cl | H |
| 6-198 | Cl | Me | Me | H | H | H | Cl |
| 6-199 | Cl | Me | Cl | Me | H | H | H |
| 6-200 | Cl | Me | H | Me | Cl | H | H |
| 6-201 | Cl | Me | H | Me | H | Cl | H |
| 6-202 | Cl | Me | H | Me | H | H | Cl |
| 6-203 | Cl | Me | Cl | H | Me | H | H |
| 6-204 | Cl | Me | H | Cl | Me | H | H |
| 6-205 | Cl | Me | Cl | Cl | H | H | H |
| 6-206 | Cl | Me | Cl | H | Cl | H | H |
| 6-207 | Cl | Me | Cl | H | H | Cl | H |
| 6-208 | Cl | Me | Cl | H | H | H | Cl |
| 6-209 | Cl | Me | H | Cl | Cl | H | H |
| 6-210 | Cl | Me | H | Cl | H | Cl | H |
| 6-211 | Br | Me | Me | Cl | H | H | H |
| 6-212 | Br | Me | Me | H | Cl | H | H |
| 6-213 | Br | Me | Me | H | H | Cl | H |
| 6-214 | Br | Me | Me | H | H | H | Cl |
| 6-215 | Br | Me | Cl | Me | H | H | H |
| 6-216 | Br | Me | H | Me | Cl | H | H |
| 6-217 | Br | Me | H | Me | H | Cl | H |
| 6-218 | Br | Me | H | Me | H | H | Cl |
| 6-219 | Br | Me | Cl | H | Me | H | H |
| 6-220 | Br | Me | H | Cl | Me | H | H |
| 6-221 | Br | Me | Cl | Cl | H | H | H |
| 6-222 | Br | Me | Cl | H | Cl | H | H |
| 6-223 | Br | Me | Cl | H | H | Cl | H |
| 6-224 | Br | Me | Cl | H | H | H | Cl |
| 6-225 | Br | Me | W | Cl | Cl | H | H |
| 6-226 | Br | Me | H | Cl | H | Cl | H |

TABLE 7

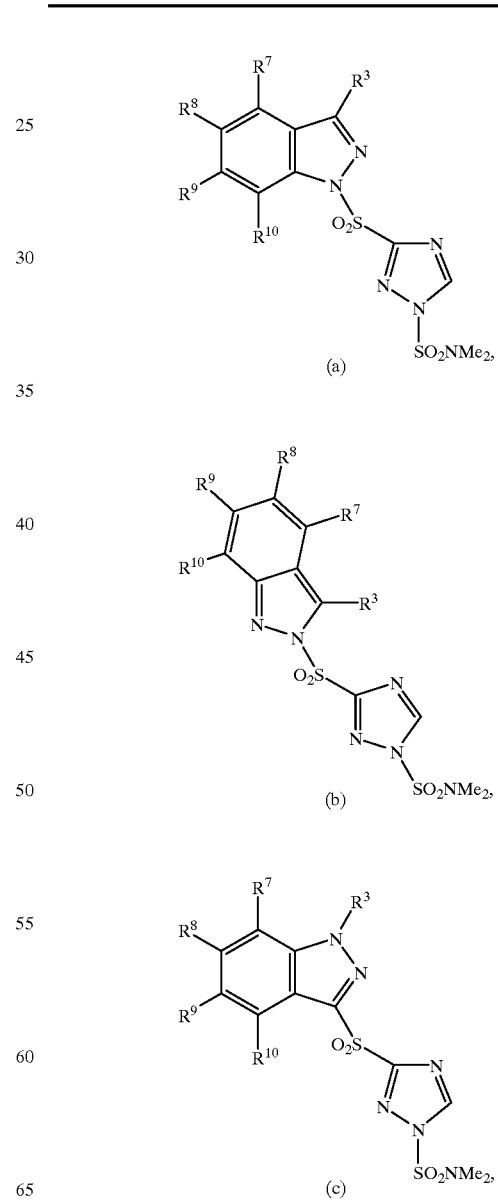

TABLE 7-continued
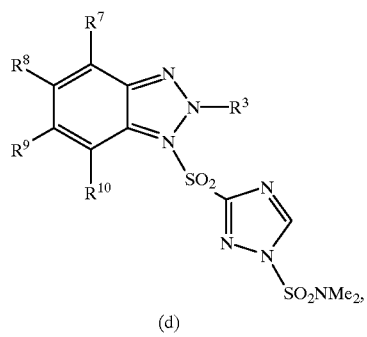
(d)
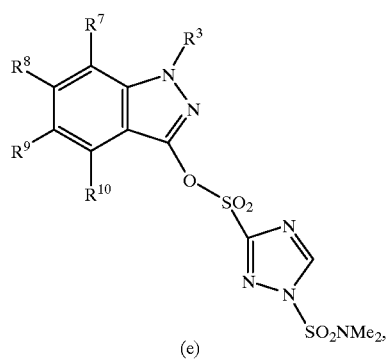
(e)
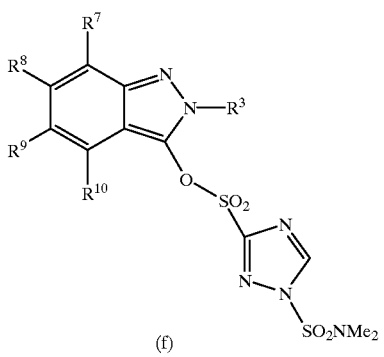
(f)
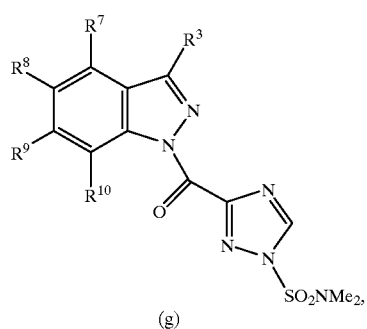
(g)
TABLE 7-continued
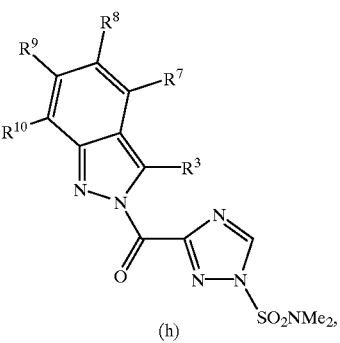
(h)
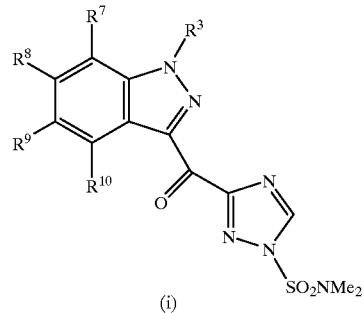
(i)
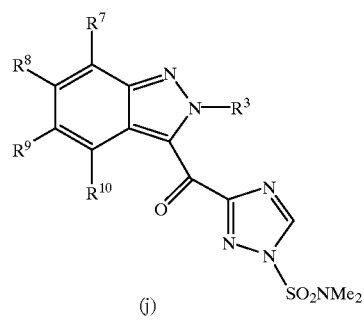
(j)
| Compound No. | $R^3$ | $R^7$ | $R^8$ | $R^9$ | $R^{10}$ |
|---|---|---|---|---|---|
| 7-1 | H | H | H | H | H |
| 7-2 | Me | H | H | H | H |
| 7-3 | Et | H | H | H | H |
| 7-4 | Ph | H | H | H | H |
| 7-5 | Cl | H | H | H | H |
| 7-6 | Br | H | H | H | H |
| 7-7 | $CF_3$ | H | H | H | H |
| 7-8 | H | Cl | H | H | H |
| 7-9 | H | H | Cl | H | H |
| 7-10 | H | H | H | Cl | H |
| 7-11 | H | H | H | H | Cl |
| 7-12 | H | Br | H | H | H |
| 7-13 | H | H | Br | H | H |
| 7-14 | H | H | H | Br | H |
| 7-15 | H | H | H | H | Br |

TABLE 8
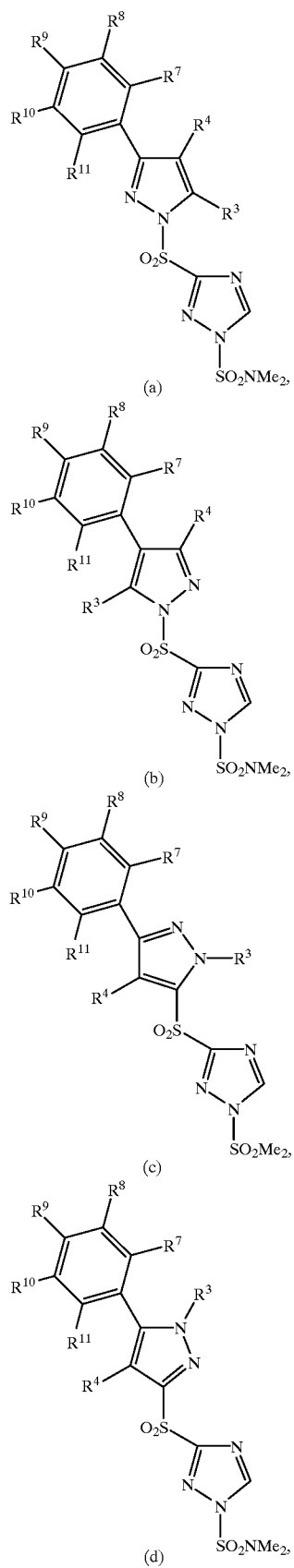
(a)
(b)
(c)
(d)
TABLE 8-continued
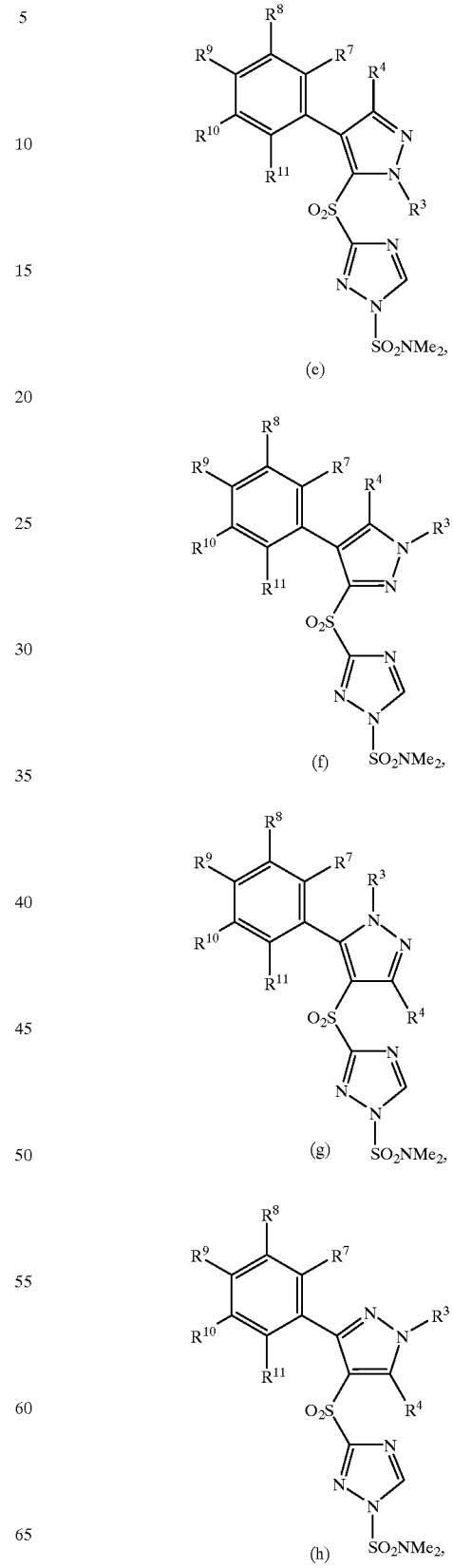
(e)
(f)
(g)
(h)

TABLE 8-continued

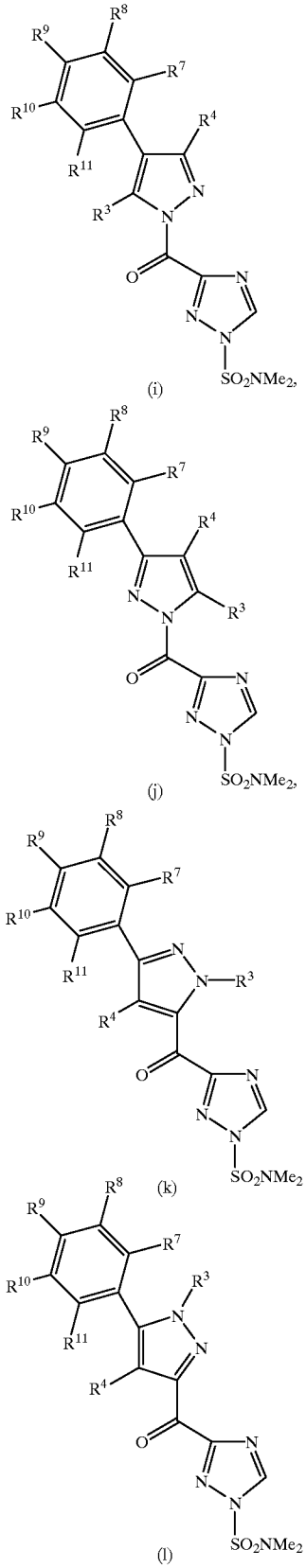

(i), (j), (k), (l)

| Compound No. | R³ | R⁴ | R⁷ | R⁸ | R⁹ | R¹⁰ | R¹¹ |
|---|---|---|---|---|---|---|---|
| 8-1 | H | H | H | H | H | H | H |
| 8-2 | H | Cl | H | H | H | H | H |
| 8-3 | H | Br | H | H | H | H | H |
| 8-4 | H | NO₂ | H | H | H | H | H |
| 8-5 | H | CO₂Me | H | H | H | H | H |
| 8-6 | H | CN | H | H | H | H | H |
| 8-7 | H | Me | H | H | H | H | H |
| 8-8 | H | Et | H | H | H | H | H |
| 8-9 | H | Ph | H | H | H | H | H |
| 8-10 | Me | H | H | H | H | H | H |
| 8-11 | Me | Cl | H | H | H | H | H |
| 8-12 | Me | Br | H | H | H | H | H |
| 8-13 | Me | NO₂ | H | H | H | H | H |
| 8-14 | Me | CO₂Me | H | H | H | H | H |
| 8-15 | Me | CN | H | H | H | H | H |
| 8-16 | Me | Me | H | H | H | H | H |
| 8-17 | Me | Et | H | H | H | H | H |
| 8-18 | Me | Ph | H | H | H | H | H |
| 8-19 | Et | H | H | H | H | H | H |
| 8-20 | Et | Cl | H | H | H | H | H |
| 8-21 | Et | Br | H | H | H | H | H |
| 8-22 | Et | NO₂ | H | H | H | H | H |
| 8-23 | Et | CO₂Me | H | H | H | H | H |
| 8-24 | Et | CN | H | H | H | H | H |
| 8-25 | Et | Me | H | H | H | H | H |
| 8-26 | Et | Et | H | H | H | H | H |
| 8-27 | Et | Ph | H | H | H | H | H |
| 8-28 | n-Pr | H | H | H | H | H | H |
| 8-29 | n-Pr | Cl | H | H | H | H | H |
| 8-30 | n-Pr | Br | H | H | H | H | H |
| 8-31 | n-Pr | NO₂ | H | H | H | H | H |
| 8-32 | n-Pr | CO₂Me | H | H | H | H | fl |
| 8-33 | n-Pr | CN | H | H | H | H | H |
| 8-34 | n-Pr | Me | H | H | H | H | H |
| 8-35 | n-Pr | Et | H | H | H | H | H |
| 8-36 | n-Pr | Ph | H | H | H | H | H |
| 8-37 | Cl | H | H | H | H | H | H |
| 8-38 | Cl | Cl | H | H | H | H | H |
| 8-39 | Cl | Br | H | H | H | H | H |
| 8-40 | Cl | NO₂ | H | H | H | H | H |
| 8-41 | Cl | CO₂Me | H | H | H | H | H |
| 8-42 | Cl | CN | H | H | H | H | H |
| 8-43 | Cl | Me | H | H | H | H | H |
| 8-44 | Cl | Et | H | H | H | H | H |
| 8-45 | Cl | Ph | H | H | H | H | H |
| 8-46 | Br | H | H | H | H | H | H |
| 8-47 | Br | Cl | H | H | H | H | H |
| 8-48 | Br | Br | H | H | H | H | H |
| 8-49 | Br | NO₂ | H | H | H | H | H |
| 8-50 | Br | CO₂Me | H | H | H | H | H |
| 8-51 | Br | CN | H | H | H | H | H |
| 8-52 | Br | Me | H | H | H | H | H |
| 8-53 | Br | Et | H | H | H | H | H |
| 8-54 | Br | Ph | H | H | H | H | H |
| 8-55 | CF₃ | H | H | H | H | H | H |
| 8-56 | CF₃ | Cl | H | H | H | H | H |
| 8-57 | CF₃ | Br | H | H | H | H | H |
| 8-58 | CF₃ | NO₂ | H | H | H | H | H |
| 8-59 | CF₃ | CO₂Me | H | H | H | H | H |
| 8-60 | CF₃ | CN | H | H | H | H | H |
| 8-61 | CF₃ | Me | H | H | H | H | H |
| 8-62 | CF₃ | Et | H | H | H | H | H |
| 8-63 | CF₃ | Ph | H | H | H | H | H |
| 8-64 | Ph | H | H | H | H | H | H |
| 8-65 | Ph | Cl | H | H | H | H | H |
| 8-66 | Ph | Br | H | H | H | H | H |
| 8-67 | Ph | NO₂ | H | H | H | H | H |
| 8-68 | Ph | CO₂Me | H | H | H | H | H |
| 8-69 | Ph | CN | H | H | H | H | H |
| 8-70 | Ph | Me | H | H | H | H | H |
| 8-71 | Ph | Et | H | H | H | H | H |
| 8-72 | Ph | Ph | H | H | H | H | H |
| 8-73 | Me | Cl | Me | H | H | H | H |
| 8-74 | Me | Cl | H | Me | H | H | H |
| 8-75 | Me | Cl | H | H | Me | H | H |
| 8-76 | Me | Cl | Cl | H | H | H | H |
| 8-77 | Me | Cl | H | Cl | H | H | H |

TABLE 8-continued
| | | | | | | | |
|---|---|---|---|---|---|---|---|
| 8-78 | Me | Cl | H | H | Cl | H | H |
| 8-79 | Me | Cl | Br | H | H | H | H |
| 8-80 | Me | Cl | H | Br | H | H | H |
| 8-81 | Me | Cl | H | H | Br | H | H |
| 8-82 | Me | Cl | $CF_3$ | H | H | H | H |
| 8-83 | Me | Cl | H | $CF_3$ | H | H | H |
| 8-84 | Me | Cl | H | H | $CF_3$ | H | H |
| 8-85 | Me | Br | Me | H | H | H | H |
| 8-86 | Me | Br | H | Me | H | H | H |
| 8-87 | Me | Br | H | H | Me | H | H |
| 8-88 | Me | Br | Cl | H | H | H | H |
| 8-89 | Me | Br | H | Cl | H | H | H |
| 8-90 | Me | Br | H | H | Cl | H | H |
| 8-91 | Me | Br | Br | H | H | H | H |
| 8-92 | Me | Br | H | Br | H | H | H |
| 8-93 | Me | Br | H | H | Br | H | H |
| 8-94 | Me | Br | $CF_3$ | H | H | H | H |
| 8-95 | Me | Br | H | $CF_3$ | H | H | H |
| 8-96 | Me | Br | H | H | $CF_3$ | H | H |
TABLE 9
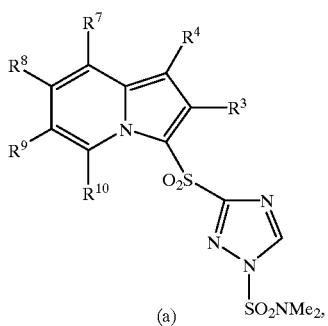
(a)
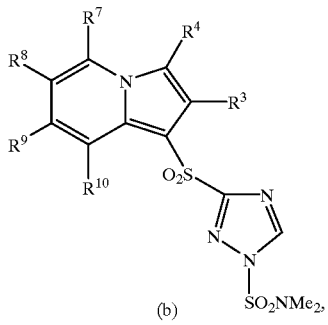
(b)
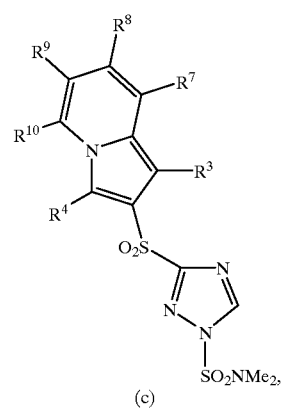
(c)
TABLE 9-continued
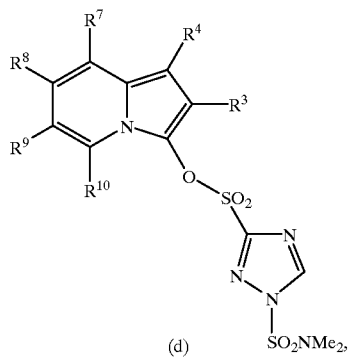
(d)
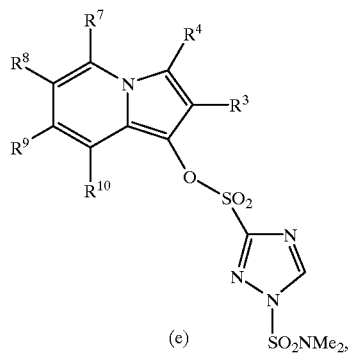
(e)
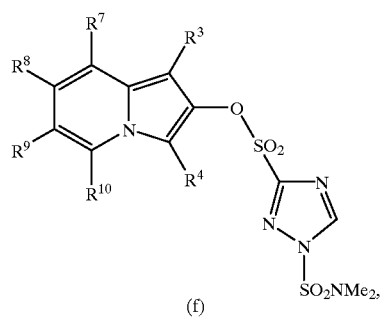
(f)
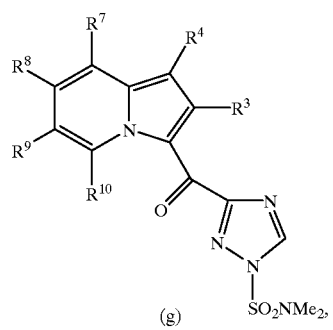
(g)

TABLE 9-continued

Structure (h): indolizine with R7, R8, R9, R10 on benzene ring, R3, R4 on pyrrole ring, connected via C(=O) to 1,2,4-triazole bearing SO2NMe2

Structure (i): alternate indolizine isomer connected via C(=O) to 1,2,4-triazole bearing SO2NMe2

| Compound No. | R$^3$ | R$^4$ | R$^7$ | R$^8$ | R$^9$ | R$^{10}$ |
|---|---|---|---|---|---|---|
| 9-1 | H | H | H | H | H | H |
| 9-2 | H | Cl | H | H | H | H |
| 9-3 | H | Br | H | H | H | H |
| 9-4 | H | NO$_2$ | H | H | H | H |
| 9-5 | H | CN | H | H | H | H |
| 9-6 | H | CF$_3$ | H | H | H | H |
| 9-7 | H | Me | H | H | H | H |
| 9-8 | H | Et | H | H | H | H |
| 9-9 | H | SMe | H | H | H | H |
| 9-10 | H | CO$_2$Me | H | H | H | H |
| 9-11 | Me | H | H | H | H | H |
| 9-12 | Me | Cl | H | H | H | H |
| 9-13 | Me | Br | H | H | H | H |
| 9-14 | Me | NO$_2$ | H | H | H | H |
| 9-15 | Me | CN | H | H | H | H |
| 9-16 | Me | CF$_3$ | H | H | H | H |
| 9-17 | Me | Me | H | H | H | H |
| 9-18 | Me | Et | H | H | H | H |
| 9-19 | Me | SMe | H | H | H | H |
| 9-20 | Me | CO$_2$Me | H | H | H | H |
| 9-21 | Et | H | H | H | H | H |
| 9-22 | Et | Cl | H | H | H | H |
| 9-23 | Et | Br | H | H | H | H |
| 9-24 | Et | NO$_2$ | H | H | H | H |
| 9-25 | Et | CN | H | H | H | H |
| 9-26 | Et | CF$_3$ | H | H | H | H |
| 9-27 | Et | Me | H | H | H | H |
| 9-28 | Et | Et | H | H | H | H |
| 9-29 | Et | SMe | H | H | H | H |
| 9-30 | Et | CO$_2$Me | H | H | H | H |
| 9-31 | Cl | H | H | H | H | H |
| 9-32 | Cl | Me | H | H | H | H |
| 9-33 | Cl | Et | H | H | H | H |
| 9-34 | Cl | CN | H | H | H | H |
| 9-35 | Cl | CF$_3$ | H | H | H | H |
| 9-36 | Cl | Cl | W | H | H | H |
| 9-37 | Cl | Br | H | H | H | H |
| 9-38 | Cl | NO$_2$ | W | H | H | H |
| 9-39 | Cl | SMe | H | H | H | H |
| 9-40 | Cl | CO$_2$Me | H | H | H | H |
| 9-41 | Br | H | H | H | H | H |
| 9-42 | Br | Me | H | H | H | H |
| 9-43 | Br | Et | H | H | H | H |
| 9-44 | Br | CN | H | H | H | H |
| 9-45 | Br | CF$_3$ | H | H | H | H |
| 9-46 | Br | Cl | H | H | H | H |
| 9-47 | Br | Br | H | H | H | H |
| 9-48 | Br | NO$_2$ | H | H | H | H |
| 9-49 | Br | SMe | H | H | H | H |
| 9-50 | Br | CO$_2$Me | H | H | H | H |
| 9-51 | CF$_3$ | H | H | H | H | H |
| 9-52 | CF$_3$ | Me | H | H | H | H |
| 9-53 | CF$_3$ | Et | H | H | H | H |
| 9-54 | CF$_3$ | CN | H | H | H | H |
| 9-55 | CF$_3$ | CF$_3$ | H | H | H | H |
| 9-56 | CF$_3$ | Cl | H | H | H | H |
| 9-57 | CF$_3$ | Br | H | H | H | H |
| 9-58 | CF$_3$ | NO$_2$ | H | H | H | H |
| 9-59 | CF$_3$ | SMe | H | H | H | H |
| 9-60 | CF$_3$ | CO$_2$Me | H | H | H | H |
| 9-61 | SMe | H | H | H | H | H |
| 9-62 | SMe | Cl | H | H | H | H |
| 9-63 | SMe | Br | H | H | H | H |
| 9-64 | SMe | NO$_2$ | H | H | H | H |
| 9-65 | SMe | CN | H | H | H | H |
| 9-66 | SMe | CF$_3$ | H | H | H | H |
| 9-67 | SMe | Me | H | H | H | H |
| 9-68 | SMe | Et | H | H | H | H |
| 9-69 | SMe | SMe | H | H | H | H |
| 9-70 | SMe | CO$_2$Me | H | H | H | H |
| 9-71 | CN | H | H | H | H | H |
| 9-72 | CN | Me | H | H | H | H |
| 9-73 | CN | Et | H | H | H | H |
| 9-74 | CN | CN | H | H | H | H |
| 9-75 | CN | CF$_3$ | H | H | H | H |
| 9-76 | CN | Cl | H | H | H | H |
| 9-77 | CN | Br | H | H | H | H |
| 9-78 | CN | NO$_2$ | H | H | H | H |
| 9-79 | CN | SMe | H | H | H | H |
| 9-80 | CN | CO$_2$Me | H | H | H | H |
| 9-81 | Me | H | Me | H | H | H |
| 9-82 | Me | H | H | Me | H | H |
| 9-83 | Me | H | H | H | Me | H |
| 9-84 | Me | H | H | H | H | Me |
| 9-85 | Me | H | F | H | H | H |
| 9-86 | Me | H | H | F | H | H |
| 9-87 | Me | H | H | H | F | H |
| 9-88 | Me | H | H | H | H | F |
| 9-89 | Me | H | Cl | H | H | H |
| 9-90 | Me | H | H | Cl | H | H |
| 9-91 | Me | H | H | H | Cl | H |
| 9-92 | Me | H | H | H | H | Cl |
| 9-93 | Me | H | Br | H | H | H |
| 9-94 | Me | H | H | Br | H | H |
| 9-95 | Me | H | H | H | Br | H |
| 9-96 | Me | H | H | H | H | Br |
| 9-97 | Me | Cl | Me | H | H | H |
| 9-98 | Me | Cl | H | Me | H | H |
| 9-99 | Me | Cl | H | H | Me | H |
| 9-100 | Me | Cl | H | H | H | Me |
| 9-101 | Me | Cl | F | H | H | H |
| 9-102 | Me | Cl | H | F | H | H |
| 9-103 | Me | Cl | H | H | F | H |
| 9-104 | Me | Cl | H | H | H | F |
| 9-105 | Me | Cl | Cl | H | H | H |
| 9-106 | Me | Cl | H | Cl | H | H |
| 9-107 | Me | Cl | H | H | Cl | H |
| 9-108 | Me | Cl | H | H | W | Cl |
| 9-109 | Me | Cl | Br | H | H | H |
| 9-110 | Me | Cl | H | Br | H | H |
| 9-111 | Me | Cl | H | H | Br | H |
| 9-112 | Me | Cl | H | H | H | Br |
| 9-113 | Me | Br | Me | H | H | H |
| 9-114 | Me | Br | H | Me | H | H |
| 9-115 | Me | Br | H | H | Me | H |
| 9-116 | Me | Br | H | H | H | Me |
| 9-117 | Me | Br | F | H | H | H |
| 9-118 | Me | Br | H | F | H | H |
| 9-119 | Me | Br | H | H | F | H |
| 9-120 | Me | Br | H | H | H | F |

TABLE 9-continued
| | | | | | | |
|---|---|---|---|---|---|---|
| 9-121 | Me | Br | Cl | H | H | H |
| 9-122 | Me | Br | H | Cl | H | H |
| 9-123 | Me | Br | H | H | Cl | H |
| 9-124 | Me | Br | H | H | H | Cl |
| 9-125 | Me | Br | Br | H | H | H |
| 9-126 | Me | Br | H | Br | H | H |
| 9-127 | Me | Br | H | H | Br | H |
| 9-128 | Me | Br | H | H | H | Br |
TABLE 10
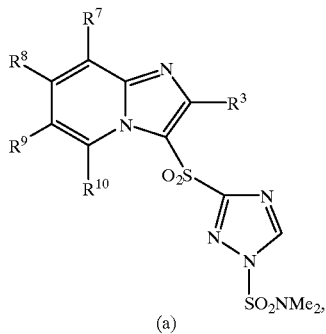
(a)
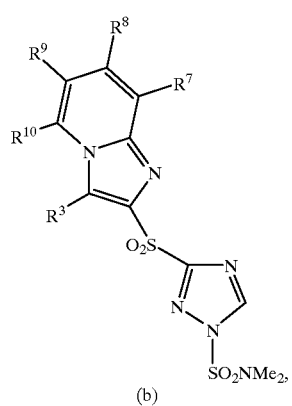
(b)
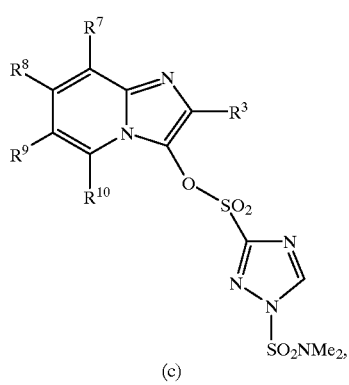
(c)
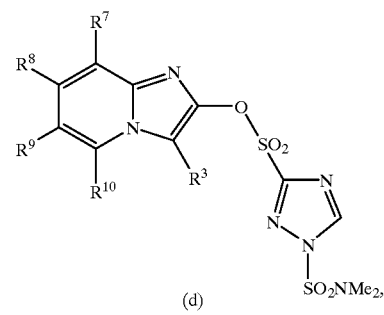
(d)
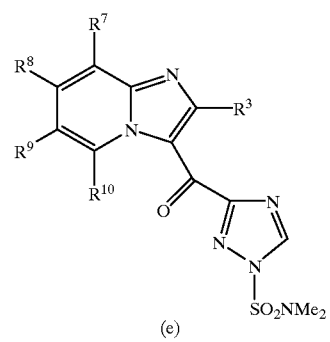
(e)
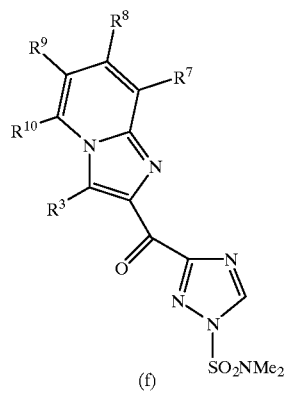
(f)
TABLE 10-continued
| Compound No. | R³ | R⁷ | R⁸ | R⁹ | R¹⁰ |
|---|---|---|---|---|---|
| 10-1 | H | H | H | H | H |
| 10-2 | Me | H | H | H | H |
| 10-3 | Et | H | H | H | H |
| 10-4 | n-Pr | H | H | H | H |
| 10-5 | Cl | H | H | H | H |
| 10-6 | Br | H | H | H | H |
| 10-7 | Sme | H | H | H | H |
| 10-8 | CF₃ | H | H | H | H |
| 10-9 | CN | H | H | H | H |
| 10-10 | H | Me | H | H | H |
| 10-11 | H | H | Me | H | H |
| 10-12 | H | H | H | Me | H |
| 10-13 | H | H | H | H | Me |
| 10-14 | H | F | H | H | H |
| 10-15 | H | H | F | H | H |
| 10-16 | H | H | H | F | H |
| 10-17 | H | H | H | H | F |
| 10-18 | H | Cl | H | H | H |
| 10-19 | H | H | Cl | H | H |
| 10-20 | H | H | H | Cl | H |
| 10-21 | H | H | H | H | Cl |
| 10-22 | H | Br | H | H | H |
| 10-23 | H | H | Br | H | H |
| 10-24 | H | H | H | Br | H |

TABLE 10-continued

| | | | | | |
|---|---|---|---|---|---|
| 10-25 | H | H | H | H | Br |
| 10-26 | Me | Me | H | H | H |
| 10-27 | Me | H | Me | H | H |
| 10-28 | Me | H | H | Me | H |
| 10-29 | Me | H | H | H | Me |
| 10-30 | Me | F | H | H | H |
| 10-31 | Me | H | F | H | H |
| 10-32 | Me | H | H | F | H |
| 10-33 | Me | H | H | H | F |
| 10-34 | Me | Cl | H | H | H |
| 10-35 | Me | H | Cl | H | H |
| 10-36 | Me | H | H | Cl | H |
| 10-37 | Me | H | H | H | Cl |
| 10-38 | Me | Br | H | H | H |
| 10-39 | Me | H | Br | H | H |
| 10-40 | Me | H | H | Br | H |
| 10-41 | Me | H | H | H | Br |
| 10-42 | Et | Me | H | H | H |
| 10-43 | Et | H | Me | H | H |
| 10-44 | Et | H | H | Me | H |
| 10-45 | Et | H | H | H | Me |
| 10-46 | Et | F | H | H | H |
| 10-47 | Et | H | F | H | H |
| 10-48 | Et | H | H | F | H |
| 10-49 | Et | H | H | H | F |
| 10-50 | Et | Cl | H | H | H |
| 10-51 | Et | H | Cl | H | H |
| 10-52 | Et | H | H | Cl | H |
| 10-53 | Et | H | H | H | Cl |
| 10-54 | Et | Br | H | H | H |
| 10-55 | Et | H | Br | H | H |
| 10-56 | Et | H | H | Br | H |
| 10-57 | Et | H | H | H | Br |
| 10-58 | Cl | Me | H | H | H |
| 10-59 | Cl | H | Me | H | H |
| 10-60 | Cl | H | H | Me | H |
| 10-61 | Cl | H | H | H | Me |
| 10-62 | Cl | F | H | H | H |
| 10-63 | Cl | H | F | H | H |
| 10-64 | Cl | H | H | F | H |
| 10-65 | Cl | H | H | H | F |
| 10-66 | Cl | Cl | H | H | H |
| 10-67 | Cl | H | Cl | H | H |
| 10-68 | Cl | H | H | Cl | H |
| 10-69 | Cl | H | H | H | Cl |
| 10-70 | Cl | Br | H | H | H |
| 10-71 | Cl | H | Br | H | H |
| 10-72 | Cl | H | H | Br | H |
| 10-73 | Cl | H | H | H | Br |
| 10-74 | Br | Me | H | H | H |
| 10-75 | Br | H | Me | H | H |
| 10-76 | Br | H | H | Me | H |
| 10-77 | Br | H | H | H | Me |
| 10-78 | Br | F | H | H | H |
| 10-79 | Br | H | F | H | H |
| 10-80 | Br | H | H | F | H |
| 10-81 | Br | H | H | H | F |
| 10-82 | Br | Cl | H | H | H |
| 10-83 | Br | H | Cl | H | H |
| 10-84 | Br | H | H | Cl | H |
| 10-85 | Br | H | H | H | Cl |
| 10-86 | Br | Br | H | H | H |
| 10-87 | Br | H | Br | H | H |
| 10-88 | Br | H | H | Br | H |
| 10-89 | Br | H | H | H | Br |

TABLE 11

(a) and (b) structures with $R^7$, $R^8$, $R^9$, $R^{10}$, $R^{11}$ substituents and $SO_2NMe_2$ group.

| Compound No. | $R^7$ | $R^8$ | $R^9$ | $R^{10}$ | $R^{11}$ |
|---|---|---|---|---|---|
| 11-1 | H | H | H | H | H |
| 11-2 | Me | H | H | H | H |
| 11-3 | H | Me | H | H | H |
| 11-4 | H | H | Me | H | H |
| 11-5 | Et | H | H | H | H |
| 11-6 | H | Et | H | H | H |
| 11-7 | H | H | Et | H | H |
| 11-8 | F | H | H | H | H |
| 11-9 | H | F | H | H | H |
| 11-10 | H | H | F | H | H |
| 11-11 | Cl | H | H | H | H |
| 11-12 | H | Cl | H | H | H |
| 11-13 | H | H | Cl | H | H |
| 11-14 | Br | H | H | H | H |
| 11-15 | H | Br | H | H | H |
| 11-16 | H | H | Br | H | H |
| 11-17 | $CF_3$ | H | H | H | H |
| 11-18 | H | $CF_3$ | H | H | H |
| 11-19 | H | H | $CF_3$ | H | H |
| 11-20 | $OCF_3$ | H | H | H | H |
| 11-21 | H | $OCF_3$ | H | H | H |
| 11-22 | H | H | $OCF_3$ | H | H |
| 11-23 | Ph | H | H | H | H |
| 11-24 | H | Ph | H | H | H |
| 11-25 | H | H | Ph | H | H |
| 11-26 | Oph | H | H | H | H |
| 11-27 | H | OPh | H | H | H |
| 11-28 | H | H | OPh | H | H |
| 11-29 | Bn | H | H | H | H |
| 11-30 | H | Bn | H | H | H |
| 11-31 | H | H | Bn | H | H |
| 11-32 | $CO_2Me$ | H | H | H | H |
| 11-33 | H | $CO_2Me$ | H | H | H |
| 11-34 | H | H | $CO_2Me$ | H | H |
| 11-35 | CN | H | H | H | H |
| 11-36 | H | CN | H | H | H |
| 11-37 | H | H | CN | H | H |
| 11-38 | $NO_2$ | H | H | H | H. |

TABLE 11-continued

| | | | | | |
|---|---|---|---|---|---|
| 11-39 | H | NO₂ | H | H | H |
| 11-40 | H | H | NO₂ | H | H |
| 11-41 | Ome | H | H | H | H |
| 11-42 | H | OMe | H | H | H |
| 11-43 | H | H | OMe | H | H |
| 11-44 | Me | Cl | H | H | H |
| 11-45 | Me | H | Cl | H | H |
| 11-46 | Me | H | H | Cl | H |
| 11-47 | Me | H | H | H | Cl |
| 11-48 | Cl | Me | H | H | H |
| 11-49 | H | Me | Cl | H | H |
| 11-50 | H | Me | H | Cl | H |
| 11-51 | H | Me | H | H | Cl |
| 11-52 | Cl | H | Me | H | H |
| 11-53 | H | Cl | Me | H | H |
| 11-54 | Me | Me | H | H | H |
| 11-55 | Me | H | Me | H | H |
| 11-56 | Me | H | H | Me | H |
| 11-57 | Me | H | H | H | Me |
| 11-58 | H | Me | Me | H | H |
| 11-59 | H | Me | H | Me | H |
| 11-60 | Cl | Cl | H | H | H |
| 11-61 | Cl | H | Cl | H | H |
| 11-62 | Cl | H | H | Cl | H |
| 11-63 | Cl | H | H | H | Cl |
| 11-64 | H | Cl | Cl | H | H |
| 11-65 | H | Cl | H | Cl | H |

Next, methods for preparing the compound of the invention will be explained below. However, the present invention should not be construed as being limited thereto.

(Preparation Method 1)

The compound of the invention can be prepared by reacting a compound of the formula (2)

 (2)

wherein A has the same meaning as defined above, with a compound of the formula (3)

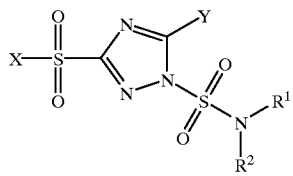

wherein $R^1$, $R^2$ and Y have the same meanings as defined above, and X is halogen.

(Preparation Method 2)

The compound of the invention can be prepared by reacting a compound of the formula (4)

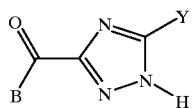

wherein B and Y have the same meanings as defined above, with a compound of the formula (5)

wherein $R^1$ and $R^2$ have the same meanings as defined above and X is halogen.

(Preparation Method 3)

The compound of the invention can be prepared by oxidizing a compound of the formula (6)

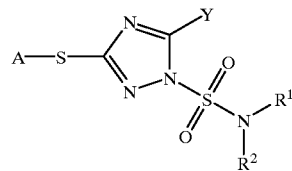

wherein $R^1$, $R^2$, A and Y have the same meanings as defined above, with an oxidizing agent.

In (Preparation Method 1), a sulfamoyl derivative (1) can be synthesized by reacting (2) with a halosulfonyltriazole (3) in the presence of a base.

The solvent may be any solvent so far as it is inert to the reaction. There may be employed, for example, ethers such as dioxane, dimethoxyethane and tetrahydrofuran, aromatic hydrocarbons such as toluene, xylene and chlorobenzene, halogenated hydrocarbons such as dichloroethane and chloroform, ketones such as acetone, methyl ethyl ketone and methyl isobutyl ketone, nitrites such as acetonitrile, tertiary amines such as pyridine, triethylamine and tributylamine, amides such as N,N-dimethylformamide, sulfur compounds such as dimethyl sulfoxide and sulfolane, nitro compounds such as nitroethane and nitrobenzene, esters such as methyl acetate, or mixtures thereof. The reaction can be performed at a reaction temperature from −78° C. to the boiling point of the solvent.

As for the base, there may be employed, for example, organic bases such as pyridine, 4-dimethylaminopyridine, triethylamine, diethylisopropylamine and N,N-diethylaniline, inorganic bases such as sodium hydroxide, potassium hydroxide, sodium carbonate, potassium carbonate, sodium hydrogen carbonate and potassium hydrogen carbonate, metal hydrides such as sodium hydride, metal alkoxides such as sodium methoxide and potassium t-butoxide, organic metal amides such as lithium diusopropylamide, organic metal compounds such as n-butyl lithium, and the like.

In the (Preparation Method 2), the sulfamoyl derivative (1) can be synthesized by reacting (4) with a dialkylsulfamoyl halide (5) in the presence of a base.

The solvent may be any solvent so far as it is inert to the reaction. There may be employed, for example, ethers such as dioxane, dimethoxyethane and tetrahydrofuran, aromatic hydrocarbons such as toluene, xylene and chlorobenzene, halogenated hydrocarbons such as dichloroethane and chloroform, ketones such as acetone, methyl ethyl ketone and methyl isobutyl ketone, nitrites such as acetonitrile, tertiary amines such as pyridine, triethylamine and tributylamine, amides such as N,N-dimethylformamide, sulfur compounds such as dimethyl sulfoxide and sulfolane, nitro compounds such as nitroethane and nitrobenzene, esters such as methyl acetate, or mixtures thereof. The reaction can be performed at a reaction temperature from −78° C. to the boiling point of the solvent.

As for the base, there may be employed, for example, organic bases such as pyridine, 4-dimethylaminopyridine, triethylamine, diethylisopropylamine and N,N-diethylaniline, inorganic bases such as sodium hydroxide, potassium hydroxide, sodium carbonate, potassium carbonate, sodium hydrogen carbonate and potassium hydrogen carbonate, metal hydrides such as sodium hydride, metal alkoxides such as sodium methoxide and potassium t-butoxide, organic metal amides such as lithium diisopropylamide, organic metal compounds such as n-butyl lithium, and the like.

In the (Preparation Method 3), the sulfamoyl derivative (1) can be synthesized by oxidizing (6) with an oxidizing agent.

The solvent may be any solvent so far as it is inert to the reaction. There may be employed, for example, ethers such as dioxane, dimethoxyethane and tetrahydrofuran, aromatic hydrocarbons such as toluene, xylene and chlorobenzene, halogenated hydrocarbons such as dichloroethane and chloroform, ketones such as acetone, methyl ethyl ketone and methyl isobutyl ketone, nitriles such as acetonitrile, amides such as N,N-dimethylformamide, esters such as ethyl acetate, carboxylic acids such as acetic acid, water, or mixtures thereof. The reaction can be performed at a reaction temperature from −78° C. to the boiling point of the solvent.

As for the oxidizing agent, there may be employed, for example, peroxides such as hydrogen peroxide, peracetic acid, 3-chloro perbenzoic acid, sodium percarbonate, and the like.

The starting compounds of the method, compounds (2), (3), (4) and (6) can be readily synthesized by known methods (see Dai Yuki Kagaku vol. 14, 299–514 for the compound (2), JP-A-5-43557 and/or JP-A-7-215971 for the compound (3), Chem. Pharm. Bull. 41(7) 1226–1231 (1993) for the compound (4), and JP-A-9-143181 for the compound (6).) or methods analogous thereto.

As for the plant diseases which are target for control by the compound of the invention, there may be mentioned: rice blast (*Pyricularia oryzae*), helminthosporium leaf spot (*Cochliobolus miyabeanus*), sheath blight (*Rhizoctonia solani*), barley and wheat: powdery mildew (*Erysiphe graminis* f. sp. hordei, f. sp. tritici), stripe (*Pyrenophora graminea*), net blotch (*Pyrenophora teres*), scab (*Gibberella zeae*), rust (*Puccinia striiformis, P. graminis, P. recondita, P. hordei*), snow blight (Tipula sp., *Micronectriella nivais*), loose smut (*Ustilago tritici, U. nuda*), eye spot (*Pseudocercosporella herpotrichoides*), scald (*Rhynchosporium secalis*), spekled leaf blotch (*Septoria tritici*), glume blotch (*Leptosphaeria nodorum*), citrus: melanose (*Diaporthe citri*), scab (*Elsinoe fawcetti*), green mold and blue mold (*Penicillium digitalum, P. italicum*), apple: blossom blight (*Sclerotinia mali*), canker (*Valsa mali*), powdery mildew (*Podosphaera lcucotricha*), alternaria leaf spot (*Alternaria mali*), scab (*Venturia inaequalis*), pear: scab (*Venturia nashicola*), black spot (*Alternaria kikuchiana*), rust (*Gymnosporangium haracanum*), peach: brown rot (*Sclerolinia cinerea*), scab (*Clcadosporium carpophilum*), phomopsis rot (Phomopsis sp.), grape: downy mildew (*Plasmopara viticola*), anthracnose (*Elsinoe ampelina*), ripe rot (*Glomerella cingulata*), powdery mildew (*Uncinula necator*), rust (*Phakopsora ampelopsidis*), kaki: anthracnose (*Gloeosporium kakj*), angular leaf spot and circular leaf spot (*Cercospora kakj, Mycosphaerella nawae*), melons: downy mildew (*Pseudoperenospora cubensis*), anthracnose (*Colletotrichum lagenarium*), powdery mildew (*Sphaerotheca fuliginea*), gummy stem blight (*Mycosphaerella melonis*), tomato: late blight (*Phytophthora infestans*), early blight (*Alternaria solani*), leaf mold (*Cladosporium fulvum*), egg plant: brown spot (*Phomopsis vexans*), powdery mildew (*Erysiphe cichoracoarum*), rape: black rot (*Alternaria japonica*), white rot (*Cercosporella brassicae*), oion: rust (*Puccinia allii*), soybean: purple stain of seed (*Cercospora kikuchil*), sphaceloma scab (*Elisinoe glycines*), black spot (*Diaporthe phaseololum*), kidney bean: anthracnose (*Colletotrichum lindemuthianum*), peanut: leaf spot (*Mycosphaerella personatum*), brown leaf spot (*Cercospora arachidicola*), pea: powdery mildew (*Erysiphe pisi*), potato: late blight (*Alternaria solani*), strawberry: powdery mildew (*Sphaerotheca humuli*), tea plant: net blister blast (*Exobasidium reticulatum*), white scab (*Elsinoe leucospila*), tobacco: brown spot (*Alternaria lingipes*), powdery mildew (*Erysiphe cichoracearum*), anthracnose (*Colletotrichum tabacum*), beet: cercospora leaf (*Cercospora beticola*), rose: black spot (*Diplocarpon rosae*), powdery mildew (*Sphaerotheca pannosa*), chrysanthemum: leaf spot (*Septoria chrysanthemuindici*), rust (*Puccinia horiana*), various crops: gray mold (*Botrytis cinerea*), various crops: sclerotinia rot (*Sclerotinia sclerotiorum*), and the like.

Upon use of the compound of the invention as agricultural and horticultural fungicides, they are generally mixed with a suitable carrier, for example, solid carriers such as clay, talc, bentonite and diatomaceous earth, or liquid carriers such as water, alcohols (methanol, ethanol, etc.), aromatic hydrocarbons (benzene, toluene, methylnaphthalene, etc.), chlorinated hydrocarbons, ethers, ketones, esters (ethyl acetate, etc.), acid amides (dimethylformamide, etc.), or the like to be applied. If desired, emulsifying agents, dispersants, suspension agents, penetrating agents, spreading agents, stabilizers and the like may be added so that the compounds can be subjected to practical application in any of formulation forms such as liquid formulation, emulsifiable concentrate, wettable powder, dust formulation, granule, or flowable powder.

The compound of the invention can be mixed or used in combination with various active compounds such as fungicides, bactericides, acaricides, nematicides and insecticides or other biologically active compounds. Common names of these active compounds will be listed below concretely. However, the invention should not be construed as being limited thereto.

Fungicidally active compounds: acibenzolar, ampropyfos, anilazine, azaconazole, azoxystrobin, benalaxyl, benodail, benomyl, benzamacril, binapacryl, biphenyl, bitertanol, bethoxazine, bordeaux mixture, blasticidin-S, bromoconazole, bupirimate, buthiobate, calcium polysulfide, captafol, captan, copper oxychloride, carpropamid, carbendazim, carboxin, chinomethionat, chlobenthiazone, chlorfenazol, chloroneb, chlorothalonil, chlozolinate, cufraneb, cymoxanil, cyproconazol, cyprodinil, cyprofuram, debacarb, dichlorophen, dichlobutrazol, dichlofluanid, dichlormedine, dichloran, diethofencarb, dichlocymet, difenoconazole, diflumetorim, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadone, fenarimol, febuconazole, fenfuram, fenpiclonil, fenpropidin, fenpropimorph, fentin, ferbam, ferimzone, fluazinam, fludioxonil, fluoroimide, fluquinconazole, flusilazole, flusulfamide, flutolanil, flutriafol, folpet, fosetyl-aluminium, fuberidazole, furalaxyl, fenamidone, fenhexamid, guazatine, hexachlorobenzene, hexaconazole, hymexazol, imazalil, imibenconazol, iminoctadine, ipconazole, iprobenfos, iprodione, isoprothiolane, iprovalicarb, kasugamycin, kresoxim-methyl, mancopper, mancozeb, maneb, mepanipyrim, mepronil, metalaxyl, metconazole, metiram, metominostrobin, myclobutanil, nabam, nickel bis (dimethyldithiocarbamate), nitrothal-isopropyl, nuarimol, octhilinone, ofurace, oxadixyl, oxycarboxin, oxpoconazole fumarate, pefurzoate, penconazole, pencycuron, phthalide, piperalin, polyoxins, probenazole, prochloraz, procymidone, propamocarb hydrochloride, propiconazole, propineb, pyrazophos, pyrifenox, pyrimethanil, pyroquilon, quinoxyfen, quintozene, sulfur, spiroxamine, tebuconazole, tecnazene, tetraconazole, thiabendazole, thifluzamide, thiophanate-methyl, thiram, toldlofos-methyl, tolylfluanid, triadimefon, toriadimenol, triazoxide, tricyclazole, tridemorph, triflumizole, triforine, triticonazole, validamycin, vinclozolin, zineb, ziram.

Bactericidally active compounds: streptomycin, oxyterracycline, oxolinic acid.

Nematicidally active compounds: aldoxycarb, fosthiazate, fosthietan, oxamyl, fenamiphos.

Acaricidally active compounds: amitraz, bromopropylate, chinomethionat, chlorobenzilate, clofentezine, cyhexatine, dicof ol, dienochlor, ethoxazole, fenazaquin, fenbutatin oxide, fenpropathrin, fenproximate, halfenprox, hexythiazox, milbemectin, propargite, pyridaben, pyrimidifen, tebufenpyrad, Insecticidally active compounds: abamectin, acephate, acetamipirid, azinphos-methyl, bendiocarb, benfuracarb, bensultap, bifenthrin, buprofezin, butocarboxim, carbaryl, carbofuran, carbosulfan, cartap, chlorfenapyr, chlorpyrifos, chlorfenvinphos, chlorf luazuron, clothianidin, chlromafenozide, chlorpyrifos-methyl, cyf luthrin, beta-cyf luthrin, cypermethrin, cyromazine, cyhalothrin, lambda-cyhalothrin, deltamethrin, diafenthiuron, diazinon, diacloden, diflubenzuron, dimethylvinphos, diofenolan, disulfoton, dimethoate, EPN, esfenvalerate, ethiofencarb, ethiprole, etofenprox, etrimfos, fenitrothion, fenobucarb, fenoxycarb, fenpropathrin, fenvalerate, fipronil, flucythrinate, flufenoxuron, flufenprox, tau-fluvalinate, fonophos, formetanate, formothion, furathiocarb, halofenozide, hexaflumuron, hydramethylnon, imidacloprid, isofenphos, indoxacarb, isoprocarb, isoxathion, lufenuron, malathion, metaldehyde, metahamidophos, methidathion, methacrifos, metalcarb, methomyl, methoprene, methoxychlor, methoxyfenozide, monocrotophos, muscalure, nitenpyram, omethoate, oxydemeton-methyl, oxamyl, parathion, parathionmethyl, permethrin, phenthoate, phoxim, phorate, phosalone, phosmet, phosphamidon, pirimicarb, pirimiphos-methyl, profenofos, pymetrozine, pyraclofos, pyriproxyfen, rotenone, sulprofos, silafluofen, spinosad, sulfotep, tebfenozide, teflubenzuron, tefluthorin, terbufos, tetrachlorovinphos, thiodicarb, thiamethoxam, thiofanox, thiometon, tolfenpyrad, tralomethrin, trichlorfon, triazuron, triflumuron, vamidothion.

When used as agricultural and horticultural fungicides, the compounds of the invention can be applied by foliage application, soil treatment, seed disinfection and the like. They are also effective in general methods usually utilized by those skilled in the art.

Further, if necessary, other herbicides, and various insecticides, fungicides, plant growth regulators, synergists and the like may be mixed at formulation or spraying and used together. An application rate of the compound of the invention varies due to an application field, an application period, an application method, a target disease, a cultured crop and the like, but generally it is suitable to apply about 0.005–50 kg of the active ingredient per hectare.

Next, formulation examples of fungicides containing the compound of the invention as active ingredients are shown as follows. However, the present invention should not be construed as being limited thereto. In the following formulation examples, all "parts" means are "parts by weight".

| Formulation Example 1 Emulsifiable Concentrate | |
|---|---|
| Compound of the invention | 20 parts |
| Methylnaphthalene | 55 parts |
| Cyclohexanone | 20 parts |
| Sorpol 2680 (mixture of nonionic surfactant and anionic surfactant: Toho Kagaku Kogyo K.K., trade name) | 5 parts |

The above components are mixed uniformly to make an emulsion. Upon use, the emulsion is diluted by 50–20,000 times to apply 0.005–50 kg of the active ingredient per hectare.

| Formulation Example 2 Wettable Powder | |
|---|---|
| Compound of the invention | 25 parts |
| Zeeklite PEP (mixture of kaolinite and celisite: Zeeklite Industry K.K., Ltd.) | 66 parts |
| Solpol 5039 (anionic surfactant: Toho Kagaku Kogyo K.K., trade name) | 4 parts |
| Carplex #80 (white carbon: Shionogi Seiyaku K.K., trade name) | 3 parts |
| Calcium ligninsulfonate | 2 parts |

The above components are mixed and grounded uniformly to make a wettable powder. Upon use, the wettable powder is diluted to 50 to 20,000 times to spray 0.005 to 50 kg of active ingredient per hectare.

| Formulation Example 3 Dust Formulation | |
|---|---|
| Compound of the invention | 3 parts |
| Carplex #80 (white carbon: Shionogi Seiyaku K.K.. trade name) | 0.5 part |
| Clay | 95 parts |
| Diisopropyl phosphate | 1.5 parts |

The above components are mixed and grounded uniformly to make a dust formulation. Upon use, the dust formulation is applied with 0.005 to 50 kg of active ingredient per hectare.

| Formulation Example 4 Granule | |
|---|---|
| Compound of the invention | 5 parts |
| Bentonite | 30 parts |
| Talc | 64 parts |
| Calcium ligninsulfonate | 1 part |

The above components are mixed and grounded uniformly, stirred to mix with addition of a small amount of water, granulated by an extrusion granulator and dried to make a granule. Upon use, the granule is applied with 0.005 to 50 kg of active ingredient per hectare.

| Formulation Example 5 Flowable Powder | |
|---|---|
| Compound of the invention | 25 parts |
| Solpol 3353 (nonionic surfactant: Toho Kagaku Kogyo K.K., trade name) | 5 parts |

-continued

Formulation Example 5 Flowable Powder

| | |
|---|---|
| Lunox 1000C (anionic surfactant: Toho Kagaku Kogyo K.K., trade name) | 0.5 part |
| Xanthan gum (natural polymer) | 0.2 part |
| Sodium benzoate | 0.4 part |
| Propylene glycol | 10 parts |
| Water | 58.9 parts |

The above components except for the active ingredient (the compound of the invention) are dissolved uniformly, to which the compound of the invention is added, stirred well, and thereafter water-grounded in a sand mill to obtain a flowable powder. Upon the flowable powder is diluted by 50–20,000 times to apply 0.005–50 kg of the active ingredient per hectare.

BEST MODE FOR CARRYING OUT THE INVENTION

Next, the present invention will be explained concretely by examples. However, the present invention should not be construed as being limited thereto.

Example 1

Preparation of 1-(N,N-dimethylsulfamoyl)-3-(2-methyl-3-chloroindol-1-yl)sulfonyl-1,2,4-triazole (1-33(a))

0.6 g of 2-methyl-3-chloroindole was dissolved in 20 ml of tetrahydrofuran, and 0.17 g of sodium hydride (55% or more) was added thereto with stirring under ice-cooling. After stirring at room temperature for 1 hour, the solution was ice-cooled again and 1.0 g of 1-N,N-dimethylsulfamoyl-3-chlorosulfonyl-1,2,4-triazole was added, and then the mixture was stirred at room temperature for 3 hours. After completion of the reaction, diluted hydrochloric acid was added and the reaction mixture was extracted with ethyl acetate. After distilling off the solvent, the residue was purified by column chromatography to obtain 0.73 g of the titled compound.

Example 2

Preparation of 1-(N,N-dimethylsulfamoyl)-3-(3-chloroindazol-1-yl)sulfonyl-1,2,4-triazole (7-5(a))

0.5 g of 3-chloroindazole was dissolved in 20 ml of tetrahydrofuran, and 0.4 g of triethylamine was added thereto with stirring under ice-cooling. Thereafter, 0.94 g of 1-N,N-dimethylsulfamoyl-3-chlorosulfonyl-1,2,4-triazole was added, and then the mixture was stirred at room temperature for 16 hours. After completion of the reaction, the reaction mixture was neutralized with diluted hydrochloric acid, and extracted with ethyl acetate. After distilling off the solvent, the residue was purified by column chromatography to obtain 0.94 g of the titled compound.

Example 3

Preparation of 1-(N,N-dimethylsulfamoyl)-3-(3-phenyl-4-chloro-5-methylpyrazol-1-yl)sulfonyl-1,2,4-triazole (8-11(a))

0.56 g of 3-phenyl-4-chloro-5-methylpyrazole was dissolved in 20 ml of tetrahydrofuran, and 0.47 g of triethylamine was added thereto with stirring under ice-cooling. Thereafter, 0.8 g of 1-N,N-dimethylsulfamoyl-3-chlorosulfonyl-1,2,4-triazole was added, and then the mixture was stirred at room temperature for 16 hours. After completion of the reaction, the reaction mixture was neutralized with diluted hydrochloric acid, and extracted with ethyl acetate. After distilling off the solvent, the residue was purified by column chromatography to obtain 1.04 g of the titled compound.

Example 4

Preparation of 1-dimethylsulfamoyl-3-(4-trifluoromethylbenzoyl)-1,2,4-triazole (11-19(a))

0.31 g of 3-(4-trifluoromethylbenzoyl)-1,2,4-triazole was dissolved in 3 ml of DMF, 0.21 g of potassium carbonate was added thereto, and then 0.22 g of dimethylsulfamoyl chloride was added at room temperature with stirring. After stirring the reaction mixture for 1.5 hours at room temperature, water was added to precipitate crystals, and the crystals were collected by filtration and washed with diethyl ether. Drying of the mixture under reducing pressure afforded 0.31 g of the titled compound.

Example 5

Preparation of 1-dimethylsulfamoyl-3-(2-methylimidazo[1,2-a]pyridin-3-ylsulfonyl)-1,2,4-triazole 10-2(a))

1.2 g of 1-dimethylsulfamoyl-3-(2-methylimidazo[1,2-a]pyridin-3-ylsulfenyl)-1,2,4-triazole was dissolved in a mixture of 20 ml of acetonitrile and 20 ml of water, and 3.0 g of sodium percarbonate was added thereto at room temperature. After stirring the mixture for 1 hour at room temperature, additional 3.0 g of sodium percarbonate was added. After completion of the reaction, the reaction mixture was neutralized with diluted hydrochloric acid and extracted with ethyl acetate. After distilling off the solvent, the residue was purified by column chromatography to obtain 0.3 g of the titled compound.

Next, the physical properties of the compounds of the formula (1) prepared according to these methods are shown in Table 12.

TABLE 12

| Compound No. | Property (m.p. ° C.) |
|---|---|
| 1-1(a) | 98–100 |
| 1-2(a) | 74–76 |
| 1-3(a) | 70–72 |
| 1-4(a) | 70–72 |
| 1-9(a) | 136–139 |
| 1-10(a) | 118–121 |
| 1-11(a) | 138–139 |
| 1-12(a) | 138–139 |
| 1-13(a) | 96–98 |
| 1-14(a) | Oil |
| 1-20(a) | 125–126 |
| 1-21(a) | 120–122 |
| 1-22(a) | 118–121 |
| 1-23(a) | 78–79 |
| 1-26(a) | 141–142.5 |
| 1-27(a) | 60–61 |
| 1-31(a) | 158–161 |
| 1-32(a) | 145.5–146.5 |
| 1-33(a) | 120–122 |
| 1-34(a) | 81–82 |
| 1-35(a) | 71–72 |
| 1-38(a) | 128–129 |
| 1-41(a) | 151–154 |
| 1-42(a) | 140–141 |
| 1-42(i) | Oil |
| 1-42(k) | 142–145 |
| 1-42(l) | 167.5–171 |
| 1-43(a) | 118.5–120 |
| 1-44(a) | 149–150 |
| 1-45(a) | Oil |

TABLE 12-continued

| Compound No. | Property (m.p. ° C.) |
|---|---|
| 1-50(a) | 124–126 |
| 1-51(a) | 181–182 |
| 1-56(a) | 94–95 |
| 1-57(a) | 61–63 |
| 1-62(a) | 147.5–149 |
| 1-63(a) | 134.5–136 |
| 1-71(a) | 159–159.5 |
| 1-72(a) | 104–107 |
| 1-81(a) | 163–165 |
| 1-105(a) | 135–137 |
| 1-118(a) | 137–140 |
| 1-119(a) | 139–140 |
| 1-125(a) | 129–131 |
| 1-126(a) | 119–121 |
| 1-130(a) | 142–145 |
| 1-131(a) | 128–129 |
| 1-133(a) | 113–115 |
| 1-135(a) | 80–81 |
| 1-136(c) | 134.5–135.5 |
| 1-148(a) | 112–113 |
| 1-152(a) | 120–122 |
| 1-161(a) | Oil |
| 1-163(a) | 134.5–136 |
| 1-168(a) | 138–139.5 |
| 1-187(a) | 172–174 |
| 1-188(a) | 166–168 |
| 1-211(a) | 94–95 |
| 1-222(a) | 126–127 |
| 1-232(a) | 172–174 |
| 1-233(a) | 164–165 |
| 1-243(a) | Oil |
| 1-258(a) | 125–128 |
| 1-265(a) | 142–143.5 |
| 1-266(a) | 114–117 |
| 1-276(a) | 177.5–179 |
| 1-276(j) | 87–89 |
| 1-277(a) | 132–133 |
| 1-283(a) | 112–113 |
| 1-289(a) | 138.5–139.5 |
| 1-290(a) | 142–143 |
| 1-298(a) | 90–92 |
| 1-311(a) | 142–143 |
| 1-316(a) | 65–66.5 |
| 1-316(j) | 91–92 |
| 1-326(a) | 82–84 |
| 1-343(a) | Oil |
| 1-353(a) | 160–163 |
| 1-370(a) | Oil |
| 1-378(a) | 93–94 |
| 1-396(a) | 149–151 |
| 1-403(a) | 129–131 |
| 1-414(a) | 151.5–153 |
| 1-421(a) | 107–108.5 |
| 1-435(a) | 184–186 |
| 1-440(a) | 194.5–195.5 |
| 1-445(a) | 50–53 |
| 1-470(a) | 120–122 |
| 1-497(a) | 119–121 |
| 1-508(a) | 148–150 |
| 1-518(a) | Oil |
| 1-537(a) | 153–155 |
| 1-548(a) | 204–206 (decomposition) |
| 1-557(a) | Oil |
| 1-568(a) | 51–53 |
| 2-2(a) | 134–135 |
| 2-2(b) | 160–161 |
| 2-2(n) | 184–186 |
| 2-2(o) | 180–181.5 |
| 2-3(b) | 140.5–142 |
| 2-3(n) | 151.5–152.5 |
| 2-3(o) | 162.5–163 |
| 2-4(b) | 176–180 |
| 2-5(a) | 143–144 |
| 2-5(b) | 174–176 |
| 2-6(a) | 104–105 |
| 2-6(d) | 141–143 |
| 2-6(e) | 168–169 |
| 2-6(n) | 173–175 |
| 2-7(a) | 117–118 |
| 2-7(b) | 142–145 |
| 2-7(n) | 143–144 |
| 2-8(b) | 177–179 |
| 2-8(x) | 123–124 |
| 2-10(a) | 112.5–114 |
| 2-10(b) | 143–145 |
| 2-10(n) | 163–164.5 |
| 2-10(v) | 138–141 |
| 2-11(e) | 149–150.5 |
| 2-14(a) | 85.5–87 |
| 2-14(b) | 150.5–153 |
| 2-17(a) | 145–147 |
| 2-17(b) | 181–183 |
| 2-18(a) | 86–87 |
| 2-18(b) | 134–136 |
| 2-19(a) | 82–83 |
| 2-19(b) | 136–138 |
| 2-20(a) | 109–110 |
| 2-20(b) | 148–149 |
| 2-24(a) | 61–63 |
| 2-24(b) | 81–83 |
| 2-26(a) | 126.5–127.5 |
| 2-30(a) | 177–179 |
| 2-30(b) | 174–176 |
| 2-34(a) | 156–157 |
| 2-34(b) | 181–183 |
| 2-39(e) | 126–128 |
| 2-44(b) | 162–163 |
| 3-1(a) | 160–162 |
| 5-1(a) | 115–118 |
| 5-22(a) | Oil |
| 5-23(a) | 39–42 |
| 5-34(a) | 55–58 (decomposition) |
| 5-58(a) | 44–47 |
| 5-82(a) | 121–123 |
| 5-146(a) | 182–184 |
| 5-146(h) | 145.5–147.5 |
| 5-153(a) | 139–140 |
| 5-165(a) | 128–129.5 |
| 5-227(a) | 42–45 |
| 5-234(a) | Oil |
| 5-247(a) | Oil |
| 5-254(a) | 68–70 |
| 5-254(h) | Oil |
| 5-261(a) | 151–154 |
| 5-274(a) | 173–176 |
| 5-490(a) | 126–129 |
| 5-495(a) | 149–150.5 |
| 5-506(a) | 145–147 |
| 6-6(a) | 163.5–164.5 |
| 6-30(a) | 54–56 |
| 7-1(a),(b) | 135–137 (mixture) |
| 7-2(e) | 135–136 |
| 7-5(a) | 164–165 |
| 8-1(a) | 154.5–155.5 |
| 8-10(a) | 110.5–111 |
| 8-11(a) | 125–128 |
| 10-2(a) | 179.5–181 |
| 11-1(a) | 81–82 |
| 11-17(a) | 89–91 |
| 11-18(a) | 62–63 |
| 11-19(a) | 121–122 |
| 11-24(a) | 133–135 |

Usefulness of the compound of the invention will be explained concretely by the following test examples. However, the present invention should not be construed as being limited thereto.

Test Example 1

Test on Cucumber Downy Mildew Controlling Effect

Cucumber (species: Sagami Hanjiro) grown in a pot having a diameter of 7 cm was applied at 1.5 leaf stage by means of a spray-gun with 20 ml per a pot of agent solution which was prepared by diluting the emulsifiable concentrate of the compound of the invention with water to 500 ppm.

A day after application, spore suspension of cucumber downy midlew pathogen (*Pseudoperonospora cubensis*) ($2 \times 10^5$/ml) was sprayed for inoculation. Inoculated cucumber was placed in an inoculation box at a temperature of 25° C. and a humidity of 95% or more for one day and night. Thereafter, the cucumber was placed in a greenhouse and determined a ratio of disease spot area formed after 7 days from inoculation to inoculated leaves to calculate a control value according to the following equation:

control value=[1−(disease spot area proportion in treated part/disease spot area proportion in non-treated part)]×100

As a result, the following compounds showed a controlling value of 100.

The compound of the invention No.: 1-1(a), 1-2(a), 1-3 (a), 1-4(a), 1-9 (a), 1-10(a), 1-11(a), 1-12(a), 1-13(a), 1-14 (a), 1-20(a), 1-21(a), 1-22(a), 1-23(a), 1-32(a), 1-33(a), 1-34(a), 1-35(a), 1-38(a), 1-41(a), 1-42(a), 1-43(a), 1-44(a), 1-45(a), 1-50(a), 1-51(a), 1-56(a), 1-62(a), 1-63(a), 1-71(a), 1-72(a), 1-81(a), 1-105(a), 1-118(a), 1-119(a), 1-125(a), 1-126(a), 1-130(a), 1-131(a), 1-133(a), 1-135(a), 1-136(c), 1-148(a), 1-152(a), 1-161(a), 1-163(a), 1-168(a), 1-187(a), 1-188(a), 1-211(a), 1-222(a), 1-232(a), 1-233(a), 1-243(a), 1-258(a), 1-265(a), 1-266(a), 1-276(a), 1-277(a), 1-283(a), 1-289(a), 1-290(a), 1-298(a), 1-311(a), 1-316(a), 1-326(a), 1-343(a), 1-353(a), 1-370(a), 1-378(a), 1-396(a), 1-403(a), 1-414(a), 1-421(a), 1-435(a), 1-440(a), 1-445(a), 1-470(a), 1-497(a), 1-508(a), 1-518(a), 1-537(a), 1-548(a), 1-568(a), 2-2(a), 2-2(b), 2-2(n), 2-2(o), 2-3(b), 2-3(n), 2-3(o), 2-4(b), 2-5(a), 2-5(b), 2-6(a), 2-6(d), 2-6(e), 2-6(n), 2-7(a), 2-7(b), 2-7(n), 2-8(b), 2-8(x), 2-10(a), 2-10(b), 2-10(n), 2-10(v), 2-11(e), 2-14(a), 2-14(b), 2-17(a), 2-17(b), 2-18(a), 2-18(b), 2-19(a), 2-19(b), 2-20(a), 2-20(b), 2-24(a), 2-24(b), 2-26(a), 2-34(a), 2-34(b), 2-39(e), 2-44(b), 3-1(a), 5-1(a), 5-22(a), 5-23(a), 5-34(a), 5-58(a), 5-82(a), 5-146(a), 5-153(a), 5-165 (a), 5-227(a), 5-234(a), 5-247(a), 5-254(a), 5-261(a), 5-274 (a), 5-490(a), 5-495(a), 5-506(a), 6-6(a), 6-30(a), 7-1(a), (b), 7-2(e), 7-5(a), 8-1(a), 8-10(a), 8-11(a), 10-2(a), 11-1(a), 11-17(a), 11-18(a), 11-19(a), 11-24(a).

Industrial Applicability

These compounds are novel, exhibit excellent agricultural and horticultural fungicidal effect and have no phytotoxicity on useful crops so that they are useful as agricultural and horticultural fungicides.

What is claimed is:

1. A compound of the general formula (1):

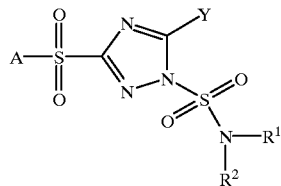

wherein $R^1$ and $R^2$ are each independently $C_{1-4}$ alkyl, or $R^1$ and $R^2$ together are $C_{4-6}$ alkylene or $C_{4-6}$ alkyleneoxy, Y is H, halogen, $C_{1-8}$ alkyl, $C_{1-4}$ alkoxy, $C_{1-8}$ alkylthio, $C_{1-8}$ haloalkyl, $C_{1-8}$ haloalkoxy or $C_{1-8}$ haloalkylthio, A is

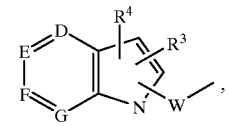
A-1

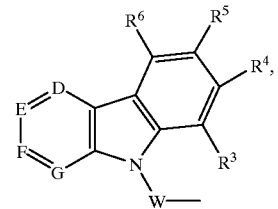
A-2

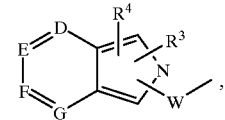
A-3

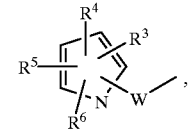
A-4

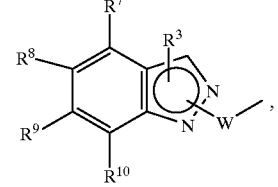
A-5

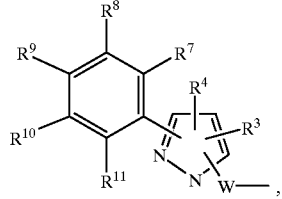
A-6

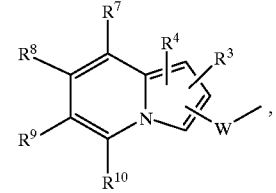
A-7

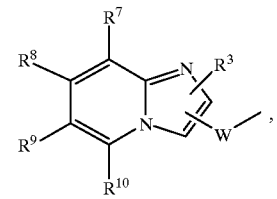
A-8

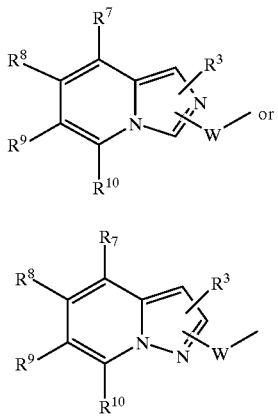

W is a chemical bond or O,
V is O or S,
D, E, F and G are each independently $CR^7$, $CR^8$, $CR^9$ or $CR^{10}$, and
$R^3$, $R^4$, $R^5$, $R^6$, $R^7$, $R^8$, $R^9$, $R^{10}$ and $R^{11}$ are each independently H, $C_{1-8}$ alkyl, $C_{1-8}$ alkoxy, $C_{1-8}$ alkylthio, $C_{1-8}$ haloalkyl, phenyl phenyl $C_{1-4}$ alkyl, phenoxy $C_{1-4}$ alkyl phenoxy benzoyl $C_{1-8}$ hydroxyalkyl, $C_{1-6}$ alkoxy $C_{1-4}$ alkyl, $C_{1-10}$ dialkoxy $C_{1-4}$ alkyl, $C_{1-3}$ alkylenedioxy $C_{1-4}$ alkyl, $C_{1-6}$ alkylthio $C_{1-4}$ alkyl, $C_{1-10}$ dialkylthio $C_{1-4}$ alkyl, $C_{1-6}$ alkoxycarbonyl, CHO, $C_{1-6}$ alkoxycarbonyl $C_{1-4}$ alkyl, $C_{1-6}$ dialkylamino, $C_{1-6}$ dialkylaminocarbonyl, $C_{1-6}$ dialkylaminocarbonyl $C_{1-4}$ alkyl, $C_{1-6}$ alkylcarbonyl, $C_{1-6}$ alkylcarbonyloxy, $C_{1-6}$ haloalkylcarbonyl, $C_{1-6}$ alkoxyimino $C_{1-4}$ alkyl, $C_{1-6}$ alkylsulfoxy, $C_{1-6}$ haloalkylsulfoxy $C_{1-4}$ alkyl, $C_{1-6}$ alkylsulfonyl, $C_{1-6}$ alkylsulfonyl $C_{1-4}$ alkyl, $C_{2-6}$ cyanoalkyl, CN, $NO_2$, halogen, phenylsulfoxy or phenylsulfonyl.

2. A compound according to claim 1, in which A is A-1.
3. A compound according to claim 1, in which A is A-2.
4. A compound according to claim 1, in which A is A-3.
5. A compound according to claim 1, in which A is A-4.
6. A compound according to claim 1, in which A is A-5 or A-6.
7. A compound according to claim 1, in which A is A-7 or A-8.
8. A compound according to claim 1, in which A is A-9 or A-10.
9. A compound according to claim 1, in which $R^1$ and $R^2$ are Me, Y is H, W is a chemical bond, A is A-1, and $R^3$ is $C_{1-8}$ alkylthio.
10. A compound according to claim 1, in which $R^1$ and $R^2$ are Me, Y is H, W is a chemical bond, A is A-1, and $R^3$ is $C_{1-8}$ haloalkyl.
11. A compound according to claim 1, in which $R^1$ and $R^2$ are Me, Y is H, W is a chemical bond, A is A-1, and $R^3$ is $C_{1-8}$ haloalkyl.
12. A compound according to claim 1, in which $R^1$ and $R^2$ are Me, Y is H, W is a chemical bond, A is A-1, and $R^3$ is halogen.
13. A compound according to claim 1, in which $R^1$ and $R^2$ are Me, Y is H, W is a chemical bond, A is A-1, and $R^3$ is H.
14. A compound according to claim 1, in which $R^1$ and $R^2$ are Me, Y is H, W is a chemical bond, A is A-1, and $R^3$ is CN.
15. A compound according to claim 1, in which $R^1$ and $R^2$ are Me, Y is H, W is a chemical bond, A is A-2, and any of $R^3$, $R^4$, $R^5$ and $R^6$ is H.
16. A compound according to claim 1, in which $R^1$ and $R^2$ are Me, Y is H, W is a chemical bond, A is A-4, and at least one of $R^3$, $R^4$, $R^5$ and $R^6$ is phenyl which may be substituted.
17. A compound according to claim 1, in which $R^1$ and $R^2$ are Me, Y is H, W is a chemical bond, and B is B-1.
18. A compound according to claim 1, in which $R^1$ and $R^2$ are Me, Y is H, W is a chemical bond, A is A-1, $R^3$ is $C_{1-8}$ alkyl, and $R^4$ is halogen.
19. A compound according to claim 1, in which $R^1$ and $R^2$ are Me, Y is H, W is a chemical bond, A is A-1, and any of $R^3$ and $R^4$ is halogen.
20. A compound according to claim 1, in which $R^1$ and $R^2$ are Me, Y is H, W is a chemical bond, A is A-1, $R^3$ is $C_{1-8}$, alkyl, and $R^3$ is H or $C_{1-8}$ alkyl.
21. A compound according to claim 1, in which $R^1$ and $R^2$ are Me, Y is H, W is a chemical bond, A is A-1, $R^3$ is $C_{1-8}$ haloalkyl, and $R^4$ is H, halogen or $C_{1-8}$ alkyl.
22. A compound according to claim 1, in which $R^1$ and $R^2$ are Me, Y is H, W is a chemical bond, A is A-1, $R^3$ is H or $C_{1-8}$ alkyl, and $R^4$ is $C_{1-6}$ alkoxycarbonyl.
23. A compound according to claim 1, in which $R^1$ and $R^2$ are Me, Y is H, W is a chemical bond, A is A-1, $R^3$ is H, and $R^4$ is halogen.
24. A compound according to claim 1, in which $R^1$ and $R^2$ are Me, Y is H, W is a chemical bond, A is A-1, $R^3$ is CN, and $R^4$ is H or $C_{1-8}$ alkyl.
25. A compound according to claim 1, in which $R^1$ and $R^2$ are Me, Y is H, W is a chemical bond, A is A-1, any of D, E, F and G is CH, $R^3$ is $C_{1-8}$ alkyl, and $R^4$ is halogen.
26. A compound according to claim 1, in which $R^1$ and $R^2$ are Me, Y is H, W is a chemical bond, A is A-1, any of D, E, F and G is CH, and any of $R^3$ and $R^4$ is halogen.
27. A compound according to claim 1, in which $R^1$ and $R^2$ are Me, Y is H, W is a chemical bond, A is A-1, any of D, E, F and G is CH, $R^3$ is $C_{1-8}$ haloalkyl, and $R^4$ is H or $C_{1-3}$ alkyl.
28. A compound according to claim 1, in which $R^1$ and $R^2$ are Me, Y is H, W is a chemical bond, A is A-1, any of D, E, F and G is CH, $R^3$ is Me or Et, and $R^4$ is Cl or Br.
29. A compound according to claim 1, in which $R^1$ and $R^2$ are Me, Y is H, W is a chemical bond, A is A-1, any of D, E, F and G is CH, $R^3$ is Cl or Br, and $R^4$ is Cl or Br.
30. An agricultural chemical containing as the active ingredient at least one sulfamoyl compound according to claim 1 and a carrier.
31. An agriculture chemical according to claim 30, in which the agriculture chemical is an agriculture and horticultural fungicide.

* * * * *

UNITED STATES PATENT AND TRADEMARK OFFICE
CERTIFICATE OF CORRECTION

PATENT NO. : 6,350,748 B1
DATED : February 26, 2002
INVENTOR(S) : Toshiaki Takeyama et al.

It is certified that error appears in the above-identified patent and that said Letters Patent is hereby corrected as shown below:

Column 69,
Line 25, after "$C_{1-8}$" delete "," (both occurrences);
Line 27, after "alkyl" insert -- , --; after "phenoxy" insert -- , --; after "benzoyl" insert -- , --;
Line 53, change "haloalkyl" to -- alkyl --.

Column 70,
Ine 23, change "$R^3$" to -- $R^4$ --.
Line 55, change "agriculture" to -- agricultural --;
Line 56, change "agriculture" to -- agricultural -- (both occurrences).

Signed and Sealed this

Eighth Day of October, 2002

Attest:

JAMES E. ROGAN
Attesting Officer  Director of the United States Patent and Trademark Office

UNITED STATES PATENT AND TRADEMARK OFFICE
CERTIFICATE OF CORRECTION

PATENT NO. : 6,350,748 B1
DATED : February 26, 2002
INVENTOR(S) : Toshiaki Takeyama et al.

It is certified that error appears in the above-identified patent and that said Letters Patent is hereby corrected as shown below:

Column 69,
Line 26, after "phenyl" (first occurrence) insert -- , --;
Line 37, after "$NO_2$" insert -- , --.

Signed and Sealed this

Twelfth Day of November, 2002

Attest:

Attesting Officer

JAMES E. ROGAN
Director of the United States Patent and Trademark Office